US007951825B2

(12) United States Patent
Harada et al.

(10) Patent No.: US 7,951,825 B2
(45) Date of Patent: May 31, 2011

(54) HETERO COMPOUND

(75) Inventors: Hironori Harada, Tokyo (JP); Kazuyuki Hattori, Tokyo (JP); Kazuya Fujita, Tokyo (JP); Masataka Morita, Tokyo (JP); Sunao Imada, Tokyo (JP); Yoshito Abe, Tokyo (JP); Hiromichi Itani, Tokyo (JP); Tatsuaki Morokata, Tokyo (JP); Hideo Tsutsumi, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/696,327

(22) Filed: Jan. 29, 2010

(65) Prior Publication Data

US 2010/0168159 A1 Jul. 1, 2010

Related U.S. Application Data

(60) Division of application No. 12/244,102, filed on Oct. 2, 2008, now Pat. No. 7,678,820, which is a continuation-in-part of application No. PCT/JP2007/057414, filed on Apr. 2, 2007.

(30) Foreign Application Priority Data

| Apr. 3, 2006 | (JP) | ............................... | P.2006-102544 |
| Oct. 10, 2006 | (JP) | ............................... | P.2006-276693 |
| Oct. 12, 2006 | (JP) | ............................... | P.2006-279227 |

(51) Int. Cl.
| C07D 413/02 | (2006.01) |
| C07D 413/14 | (2006.01) |
| C07D 401/02 | (2006.01) |
| C07D 401/14 | (2006.01) |
| A61K 31/443 | (2006.01) |

(52) U.S. Cl. ..................................... 514/340; 546/269.4
(58) Field of Classification Search ............... 546/269.4; 514/340
See application file for complete search history.

(56) References Cited

U.S. PATENT DOCUMENTS

| 7,074,809 | B2 | 7/2006 | Arora et al. |
| 7,220,734 | B2 | 5/2007 | Doherty et al. |
| 2005/0009815 | A1 | 1/2005 | DeVita et al. |
| 2007/0135461 | A1 | 6/2007 | Rodgers et al. |
| 2008/0249093 | A1 | 10/2008 | Colandrea et al. |

FOREIGN PATENT DOCUMENTS

| JP | 11-279176 | 10/1999 |
| WO | 01/12627 | 2/2001 |
| WO | 03/061567 | 7/2003 |
| WO | 03/105771 | 12/2003 |
| WO | 2004/058149 | 7/2004 |
| WO | 2004/103279 | 12/2004 |
| WO | 2004/113330 | 12/2004 |
| WO | 2005/032465 | 4/2005 |
| WO | 2005/058848 | 6/2005 |
| WO | 2006/001463 | 1/2006 |
| WO | 2006/047195 | 5/2006 |
| WO | 2006/064757 | 6/2006 |
| WO | 2006/100633 | 9/2006 |
| WO | 2007/002433 | 1/2007 |
| WO | 2007/070514 | 6/2007 |
| WO | 2008/074821 | 6/2008 |
| WO | 2008/128951 | 10/2008 |

OTHER PUBLICATIONS

Golub et al. Science (1999), vol. 286 531-537.*
Lala et al. Cancer and Metastasis Reviews (1998), 17(1), 91-106.*
"Rheumatoid arthritis." Aug. 18, 2008. http://www.webmd.com/rheumatoid-arthritis/tc/rheumatoid-arthritis-overview.*
Ishii, et al., "Lysophospholipid Receptors: Signaling and Biology", Annu. Rev. Biochem., vol. 73 (2004) 321-54.
Sugiyama, et al., "Effects of Sphingosine 1-Phosphate, a Naturally Occurring Biologically Active Lysophospholipid, on the Rat Cardiovascular System", Jpn. J. Pharmacol., vol. 82 (2000) 338-42.
Forrest, et al., "Immune Cell Regulation and Cardiovascular Effects of Sphingosine 1-Phosphate Receptor Agonist . . . ", J. Pharm. and Exp. Thera., vol. 309, No. 2 (2004) 758-68.
Matloubian, et al., "Lymphocyte egress from thymus and peripheral lymphoid organs is dependent on S1P receptor 1", Nature, vol. 427 (2004) 355-60.
Mandala, et al., "Alteration of Lymphocyte Trafficking by Sphingosine-1-Phosphate Receptor Agonists", Science, vol. 296 (2002) 346-49.
Rosen, et al., "Sphingosine 1-Phosphate and its receptors: an autocrine and paracrine network", Nature, vol. 5 (2005) 560-70.
Budde, et al., "First Human Trial of FTY720, a Novel Immunomodulator, in Stable Renal Transplant Patients", J. Am. Soc. Nephrol., vol. 13 (2002) 1073-83.
Buzard, et al., "Recent progress in the development of selective S1P1 receptor agonists for the treatment of inflammatory and autoimmune disorders", Exper Opin. Ther. Patents, vol. 18, No. 10 (2008) 1141-59.

* cited by examiner

*Primary Examiner* — Rebecca Anderson
*Assistant Examiner* — Samantha Shterengarts
(74) *Attorney, Agent, or Firm* — Fitzpatrick, Cella, Harper & Scinto

(57) ABSTRACT

To provide a useful compound as an active ingredient for a preventing and/or treating agent for rejection in the transplantation of an organ, bone marrow, or a tissue, an autoimmune disease, or the like, which has an excellent $S1P_1$ agonist activity.
Since the compound of the invention has an $S1P_1$ agonist activity, it is useful as an active ingredient for a treating or preventing agent for a disease caused by unfavorable lymphocytic infiltration, for example, an autoimmune disease such as graft rejection in the transplantation of an organ, bone marrow, or a tissue, a graft-versus-host disease, rheumatic arthritis, multiple sclerosis, systemic lupus erythematosus, a nephrotic syndrome, encephalomeningitis, myasthenia gravis, pancreatitis, hepatitis, nephritis, diabetes, pulmonary disorder, asthma, atopic dermatitis, inflammatory bowel disease, atherosclerosis, ischemia-reperfusion injury, or an inflammatory disease, and further, a disease caused by the abnormal growth or accumulation of cells such as cancer and leukemia.

3 Claims, No Drawings

HETERO COMPOUND

CROSS-REFERENCE TO RELATED APPLICATION

This application is a divisional of application Ser. No. 12/244,102 filed Oct. 2, 2008, now U.S. Pat. No. 7,678,820, which in turn is a Continuation-In-Part application of PCT patent application No. PCT/JP2007/057414 filed Apr. 2, 2007, the entire contents of which is herein incorporated by reference.

TECHNICAL FIELD

The present invention relates to a novel hetero compound and a medicine containing the same as an active ingredient, particularly an agent for treating immunological diseases.

BACKGROUND ART

Sphingosine-1-phosphate is a metabolite of sphingolipid which is a physiologically active substance secreted from an activated platelet (Non-Patent Document 1). The sphingosine-1-phosphate receptor is a G protein-binding type, and belongs to an Edg-family which is the endothelial differentiation gene. Up to now, five receptors of $S1P_1$(Edg1), $S1P_2$ (Edg5), $S1P_3$(Edg3), $S1P_4$(Edg6) and $S1P_5$(Edg8) have been found. All of these receptors are broadly distributed in cells and tissues throughout the body, but $S1P_1$, $S1P_3$ and $S1P_4$ are predominantly expressed in lymphocyte and endothelial cell, $S1P_2$ is predominantly expressed in vascular smooth muscle cell, and $S1P_5$ is predominantly expressed in brain and spleen, and amino acid sequences thereof are well-conserved in human and rodent (Non-Patent Document 1). Many receptors bind to G proteins by stimulation of sphingosine-1-phosphate. $S1P_1$ bind to $G_{i/o}$, $S1P_2$ and $S1P_3$ bind to $G_{i/o}$, $G_q$, $G_{12/13}$ and $G_5$, $S1P_4$ binds to $G_{i/o}$, $G_{12/13}$ and $G_5$, $S1P_5$ is coupled to $G_{i/o}$ and $G_{12/13}$, and cell growth caused by activation of MAPK, change of cytoskeletal system and cell infiltration caused by activation of Rac (and/or Rho), and generation of cytokine and mediator caused by activation of PLC and calcium influx into cell, and the like (Non-Patent Document 1) are induced. It has been known that by the stimulating action of $S1P_1$ of sphingosine-1-phosphate, migration of lymphocyte, inhibition of apoptosis, generation of cytokine, sequestering lymphocyte in thymus and other secondary lymphoid tissues are induced, and angioplasty in vascular endothelial cell is promoted (Non-Patent Document 2). On the other hand, expression of $S1P_3$ is also found on cardiomyocyte, and transiently-decrease in heart rate (infrequent pulse) or in blood pressure by stimulation of sphingosine-1-phosphate is observed (Non-Patent Document 3) while infrequent pulse is not observed by stimulation of sphingosine-1-phosphate in a knockout mouse wherein $S1P_3$ is genetically deleted (Non-Patent Document 4). It has been reported that FTY720 phosphate ester which is an active body of FTY720 currently in a clinical trial has non-selective agonist activity for $S1P_1$, $S1P_3$, $S1P_4$ and $S1P_5$ (Non-Patent Document 5), and especially infrequent pulse induced by the stimulation effect through $S1P_3$ is frequently expressed as an undesirable side effect in clinical trial (Non-Patent Document 6). Accordingly, it is considered that for sequestering lymphocyte through a sphingosine-1-phosphate receptor, the stimulation from $S1P_1$ is essential (Non-Patent Document 7), while the stimulation from $S1P_3$ is not essential which is rather considered to be related to the induction of undesirable side effect. Thus, for the development of immunosuppressive agent with few side effects, development of agonist having weak effect on $S1P_3$ and selectively effecting on $S1P_1$ is desired.

For example, as a compound having $S1P_1$ agonist activity, a carboxylic acid derivative represented by the following formula has been known (Patent Document 1).

[Chem. 1]

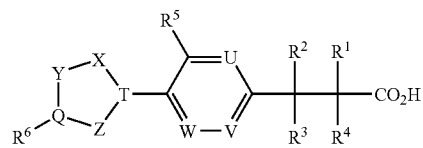

[For symbol in the formula, refer to the publication.]

As a compound having $S1P_1$ agonist activity, an indane derivative represented by the following formula has been known (Patent Document 2).

[Chem. 2]

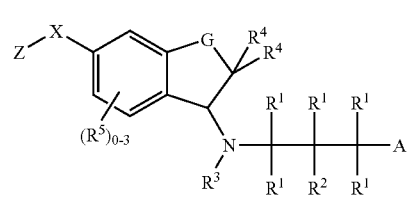

[For symbol in the formula, refer to the publication.]

As a compound having $S1P_1$ agonist activity, an oxadiazole derivative represented as follows has been known (following figure, Patent Documents 3, 4, 5, and 6).

[Chem. 3]

(Patent Document 3j)

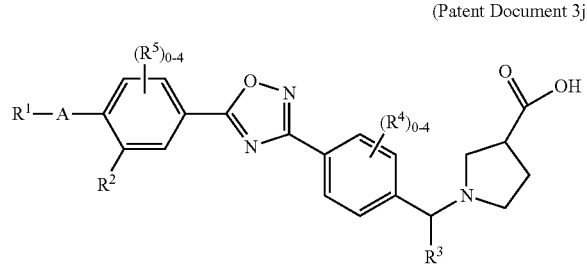

(Patent Document 4j)

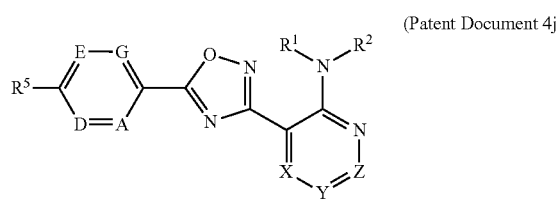

-continued

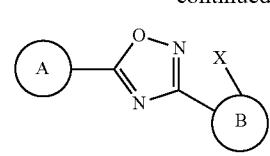

(Patent Document 5j)

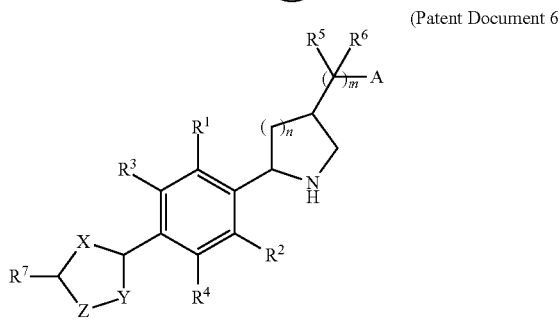

(Patent Document 6)

[For symbol in the formula, refer to the publication.]

As a compound having S1P$_1$ agonist activity, a derivative represented as follows has been known (following figure, Patent Document 7).

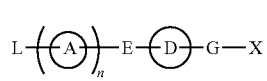

[Chem. 4]

[For symbol in the formula, refer to the publication.]

However, the compound of the present invention has not been disclosed in any document.

Non-Patent Document 1: Annual Review Biochemistry, 2004, 73, 321-354

Non-Patent Document 2: Nature Review Immunology, 2005, 5, 560-570

Non-Patent Document 3: Japanese Journal of Pharmacology, 2000, 82, 338-342

Non-Patent Document 4: Journal of Pharmacology and Experimental Therapeutics, 2004, 309, 758-768

Non-Patent Document 5: Science, 2002, 296, 346-349

Non-Patent Document 6: Journal of American Society of Nephrology, 2002, 13, 1073-1083

Non-Patent Document 7: Nature, 2004, 427, 355-360

Patent Document 1: International Publication WO 2005/058848 brochure

Patent Document 2: International Publication WO 2004/058149 brochure

Patent Document 3: International Publication WO 2003/105771 brochure

Patent Document 4: International Publication WO 2004/103279 brochure

Patent Document 5: International Publication WO 2005/032465 brochure

Patent Document 6: International Publication WO 2006/047195 brochure

Patent Document 7: International Publication WO 2006/001463 brochure

DISCLOSURE OF THE INVENTION

Problem that the Invention is to Solve

Inventors of the present inventors have carried out research in order to provide a compound useful for preventing and/or treating rejection in transplantation of organ/bone marrow/tissue or for autoimmune diseases, based on S1P$_1$ agonist activity, and furthermore to provide a medicine containing the same.

Means for Solving the Problem

Inventors of the present invention have made extensive studies about a compound having S1P$_1$ agonist activity, and as a result, they found that a novel hetero compound is useful as S1P$_1$ agonist, thus completing the present invention. In the other words, according to the present invention, a novel hetero compound represented by following the general formula (I) or a pharmaceutically acceptable salt thereof can be provided.

A compound represented by the formula (I):

[Chem. 5]

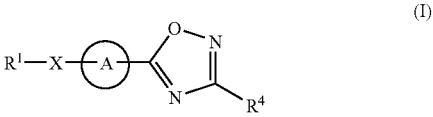

(I)

or a pharmaceutically acceptable salt thereof.

[In the formula, the symbols mean as follows;

the ring A is:

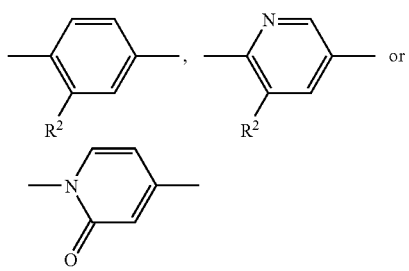

[Chem. 6]

X is a single bond, —CH$_2$—, —NR$^3$—, —O—, —S—, —S(=O)—, or —S(=O$_2$)—,

R$^1$ is —H; halogen; aryl; heteroaryl; (C$_3$-C$_8$)cycloalkyl; (C$_3$-C$_8$)cycloalkenyl; (C$_3$-C$_8$)heterocycloalkyl; or (C$_1$-C$_6$)alkyl or (C$_2$-C$_6$)alkenyl, each of which may contain halogen, —CONH$_2$, aryl, or (C$_3$-C$_8$)cycloalkyl, as a substituent, R$^2$ is —CN, —O—(C$_1$-C$_6$)alkyl, —C(=O)H, halogen; or (C$_1$-C$_6$)alkyl which may be substituted with halogen or —OH, R$^3$ is —H; wherein R$^3$ may form morpholino, 1-pyrrolidinyl or 3,4-dehydropipelidin-1-yl, together with R$^1$ and nitrogen, wherein, when —X— is a single bond, R$^1$ and R$^2$ may in combination form a 5-membered ring and further contain (C$_1$-C$_6$)alkyl, as a substituent, R$^4$ is a following ring:

wherein any one of a bond from the ring is bound to an oxadiazole ring,

[Chem. 7]

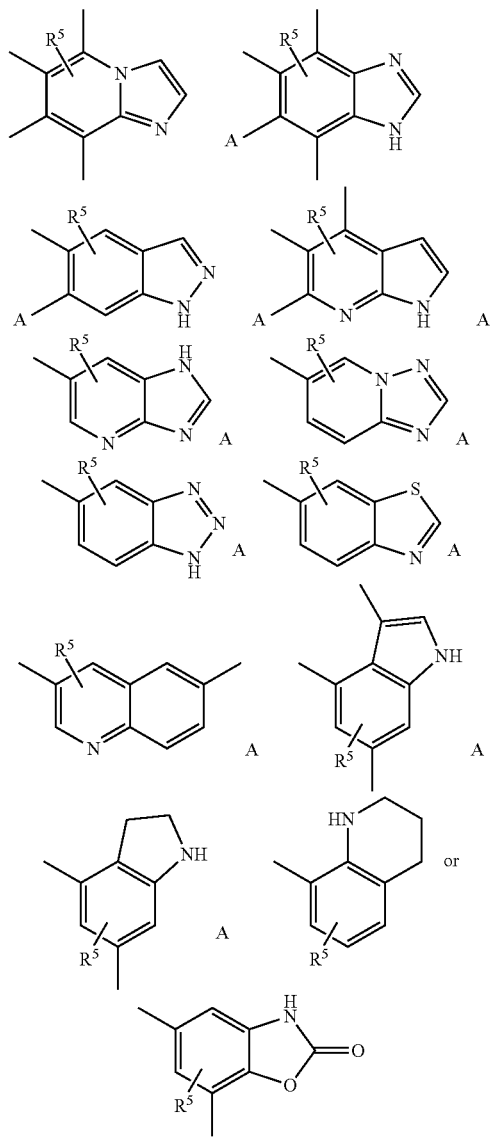

R⁵ is —H; (C₁-C₆)alkyl which may be substituted with at least one group selected from the group consisting of —CN, —C(=O)NR$^X$R$^Y$, —NHR$^X$, —SR$^X$, —S(=O)₂R$^X$, and —OR$^X$, (this is defined as R⁰—(C₁-C₆)alkyl); R⁰—(C₁-C₆)alkyl-O—; R⁰—(C₁-C₆)alkyl-C(=O)—; R⁰—(C₁-C₆)alkyl-S(=O)₂; R⁰—O—(C₁-C₆)alkyl-; R⁰—C(=O)—(C₁-C₆)alkyl-; R⁰—S(=O)₂—(C₁-C₆)alkyl-; (C₂-C₆)alkenyl-; —C(=O)H; —OR$^X$; —S(=O)₂R$^X$; halogen; =O; —NR$^X$R$^Y$; —C(=O)NR$^X$R$^Y$;

R$^X$ and R$^Y$ may be the same or different from each other, and may be —H; or (C₁-C₆)alkyl which may be substituted with —OH, —NH₂ which may be protected with a protecting group, or heteroaryl, wherein R$^X$ may form (C₃-C₈)heterocycloalkyl, together with R$^Y$ and nitrogen.

As —X— in the formula (I), preferred is a single bond or —O—, and more preferred is —O—. As R¹, preferred is (C₁-C₄)alkyl or (C₂-C₄)alkenyl, each of which may be substituted with halogen or (C₃-C₆)cycloalkyl, and further more preferred is (C₁-C₄)alkyl which may be substituted with F. As the ring A, preferred is:

[Chem. 8]

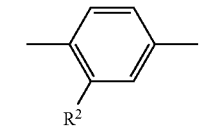

As R², preferred is halogen, —CN, (C₁-C₄)alkyl which may be substituted with halogen, and more preferred is —Cl, —CF₃. As R⁴, preferred is:

[Chem. 9]

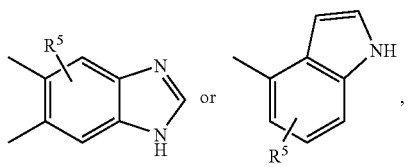

and more preferred is:

[Chem. 10]

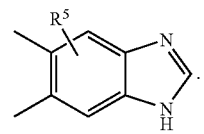

As R⁵, preferred is —H; (C₁-C₆)alkyl which may be substituted with —C(=O)NR$^X$R$^Y$. As R$^X$, preferred is —H; (C₁-C₆)alkyl which may be substituted with —OH. As R$^Y$, preferred is —H; (C₁-C₆)alkyl which may be substituted with —OH.

A compound of the present invention represented by the formula (I) is characterized in a chemical structure from the point that a bicyclic nitrogen-containing unsaturated hetero ring or a bicyclic nitrogen-containing partially unsaturated hetero ring is bound to 3-position of oxadiazole, and has pharmacological characteristics from the point that the compound has S1P₁ agonist activity.

Effects of the Invention

Since the compound of the invention has an S1P₁ agonist activity, it is useful as an active ingredient of an agent for treating or an agent for preventing a disease caused by unfavorable lymphocytic infiltration, for example, graft rejection in the transplantation of an organ, bone marrow, or tissue or graft-versus-host disease, an autoimmune disease or an inflammatory disease such as rheumatic arthritis, multiple sclerosis, systemic lupus erythematosus, nephrotic syndrome, encephalomeningitis, myasthenia gravis, pancreatitis, hepatitis, nephritis, diabetes, pulmonary disorder, asthma, atopic dermatitis, inflammatory bowel disease, atherosclerosis, or ischemia-reperfusion injury, and further, a disease caused by the abnormal growth or accumulation of cells such as cancer or leukemia.

BEST MODE FOR CARRYING OUT THE INVENTION

Hereinafter, the present invention will be described in more detail.

In the specification, "alkyl" means a linear or branched mono-valent group. "$C_1$-$C_6$ alkyl" means a $C_1$-$C_6$ linear or branched alkyl, and specific examples thereof include methyl, ethyl, n-propyl, isopropyl, n-butyl, isobutyl, t-butyl, n-propyl, and n-hexyl, preferably $C_1$-$C_4$ alkyl, and particularly preferably, methyl, ethyl, n-propyl, and isopropyl.

In the specification, "halogen" represents F, Cl, Br, and I, and preferable examples thereof include F or Cl.

In the specification, "$C_2$-$C_6$ alkenyl" means $C_2$-$C_6$ linear or branched alkenyl which has a double bond in a given site, and specific examples thereof include ethenyl (vinyl), 1-propenyl, 2-propenyl, 1-methylethen-1-yl, 1-buten-1-yl, 2-buten-1-yl, 3-buten-1-yl, 1-methyl-1-propen-1-yl, 2-methyl-1-propen-1-yl, 1-methyl-2-propen-1-yl, and 2-methyl-2-propen-1-yl, and preferably, 1-methyl-2-propen-1-yl or 1-pentenyl.

In the specification, "$C_3$-$C_8$ cycloalkyl" means a mono-valent group of a non-aromatic carbon ring having a reduction number of 3 to 8, which may have partially unsaturated bonds. Thus, specific examples thereof include cyclopropyl, cyclobutyl, cyclopentyl, and cyclohexyl.

In the specification, "$C_3$-$C_8$ heterocycloalkyl" means a mono-valent group of a non-aromatic carbon ring having a reduction number of 4 to 9, containing one or more heteroatoms that are the same as or different from each other, selected from the group consisting of nitrogen, oxygen, and optionally oxidized sulfur, which may have partial unsaturations. Specific examples thereof include aziridinyl, azetidinyl, pyrrolidinyl, piperidinyl, homopiperidinyl, morpholyl, thiomorpholyl, tetrahydropyranyl, and tetrahydrothiopyranyl.

In the specification, "aryl" means an aromatic hydrocarbon group, but preferred is an aryl group having 6 to 14 carbon atoms. Specific examples thereof include phenyl, naphthyl, and anthryl, and more preferred is phenyl.

In the specification, "heteroaryl" means a 5- or 6-membered ring aromatic heterocycle, containing one or more heteroatoms that are the same as or different from each other, selected from the group consisting of nitrogen, oxygen, and sulfur. Specific examples thereof include pyridyl, pyrazyl, pyrimidinyl, pyridazinyl, pyrrolyl, pyrazolyl, imidazolyl, oxazolyl, thiazolyl, thienyl, furyl, oxadiazolyl, and thiadiazolyl. Preferred is a 6-membered heteroaryl, and particularly preferred is pyridyl.

The compound of the present invention may exist in the form of a geometrical isomer or a tautomer in some cases depending on the kind of the substituents. Further the compound of the present invention may have asymmetric carbons. The present invention includes either of the isolated counterparts of these isomers, and a mixture thereof. Also, the labeled compounds, that is, the compounds having at least one element in the compounds of the present invention substituted with radioactive isotopes or non-radioactive isotopes are also included in the present invention.

Furthermore, the pharmaceutically acceptable, so-called prodrugs of the compounds of the present invention are also included in the present invention. The pharmaceutically acceptable prodrug is a compound having a group which can be converted into an amino group, a hydroxyl group, a carboxylic group, or the like of the compound of the present invention, by solvolysis or under a physiological condition. Examples of the group capable of forming a prodrug include the groups as described in "Prog. Med., vol. 5, 2157-2161 (1985), and "Iyakuhin no Kaihatsu (Development of Medicines) (Hirokawa Shoten, 1990), vol. 7, Bunshi Sekkei (Molecular Design)", 163-198.

The compound represented by the formula (I) may form salts with acids or bases. These salts can be any one that are pharmaceutically acceptable, and specific examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid, and salts with inorganic bases such as sodium, potassium, magnesium, calcium, and aluminum, and with organic bases such as methylamine, ethylamine, ethanolamine, lysine, and ornithine, and ammonium salts.

In addition, of the present invention also includes various hydrates and solvates, and polymorphic substances of the compound represented by the formula (I) and a salt thereof.

In the specification, the following abbreviations were used.

Pr: preparation method, AcOH: acetic acid, n-BuLi: normal butyl lithium, t-BuOH: tertiary butanol, n-BuOH: normal butanol, BrCN: cyanogen bromide, CDI: 1,1'-carbonyl bis-1H-imidazole, DBU: 1,8-diazabicyclo[5.4.0]undeca-7-ene, DMAP: 4-(N,N-dimethylamino)pyridine, DIC: N,N'-diisopropylcarbodimide, DMF: N,N'-dimethylformamide, DCC: dicyclohexylcarbodimide, DMA: N,N-dimethylacetamide, DMSO: dimethylsulfoxide, DPPA: diphenylphosphorylazide, Et: ethyl, EDCl/HCl: N-[3-(dimethylamino)propyl]-N'-ethylcarboxamide hydrochloride, EtOH: ethanol, $Et_3N$: triethylamine, EtOAc: ethyl acetate, HOBt: 1-hydroxy-1H-benzotriazole, HPLC: high performance liquid chromatography, IPE: diisopropyl ether, i-PrOH: 2-propanol, $K_2CO_3$: potassium carbonate, KCN: potassium cyanide, $KHCO_3$: potassium hydrogen carbonate, KO$^t$Bu: potassium tertiary butoxide, LC-MS: liquid chromatography-mass spectroscopy, LiH: lithium hydride, MeOH: methanol, NaH: sodium hydride, NaOH: sodium hydroxide, $NaBH_4$: sodium borohydride, NaCN: sodium cyanide, $NaHCO_3$: sodium hydrogen carbonate, $Na_2CO_3$: sodium carbonate, NaOMe: sodium methoxide, NaOEt: sodium ethoxide, NCS: N-chlorosuccinimide, $NH_4Cl$: ammonium chloride, NMP: N-methylpyrrolidone, $POCl_3$: phosphorous oxychloride, $P_2O_5$: phorphorous pentaoxide, THF: tetrahydrofuran, TLC: thin layer chromatography, TMEDA: N,N,N'N'-tetramethylethylenediamine, $Zn(CN)_2$: zinc cyanide (Preparation Method)

The compound (I) of the present invention and a pharmaceutically acceptable salt thereof may be prepared by applying various known synthetic methods, taking advantages of the characteristics based on their basic backbones or the kind of the substituents. Here, depending on the kind of the functional groups, it is in some cases effective from the viewpoint of the preparation techniques to protect the functional group with an appropriate protecting group, or to replace it by a group which may be easily converted into the functional group, during the steps of from starting materials to intermediates. Examples of such a functional group include an amino group, a hydroxyl group, and a carboxyl group, and examples of a protecting group thereof include the protecting groups as described in "Protective Groups in Organic Synthesis", edited by T. W. Greene and P. G. M. Wuts, (USA) ($3^{rd}$ edition, 1999), which may be optionally selected and used in response to the reaction conditions. By such a method, the desired compound can be obtained by introducing a protecting group to carry out the reaction, and then, if desired, removing the protecting group or converting it into a desired group.

In addition, a prodrug of the compound (I) of the present invention can be prepared by introducing a specific group during the steps of from starting materials to intermediates, similar to the aforementioned protecting groups, or by carrying out the reaction using the obtained compound (I) of the present invention. The reaction may be carried out by employing common esterification, amidation, dehydration, or a method conventionally known to a person skilled in the art.

<First Intermediate Preparation Method>

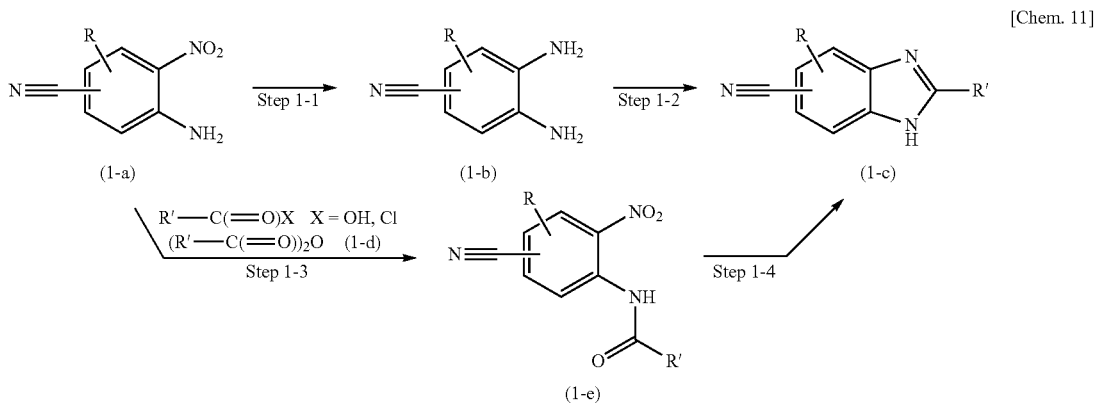

[Chem. 11]

[wherein R or R' means lower alkyl which may be substituted with at least one substituent selected from the group consisting of —CN, —C(=O)OH, —C(=O)OR$^X$, —C(=O)NR$^X$R$^Y$, —C(=O)NHSO$_2$R$^X$, —C(=O)—(C$_1$-C$_8$ heterocycloalkyl), —NHR$^X$, —OH, —SR$^X$, —S(=O$_2$)R$^X$, halogen, and —OR$^X$ (which is defined as R$^Z$-lower alkyl); R$^O$—(C$_1$-C$_6$)alkyl-O—; R$^O$—(C$_1$-C$_6$)alkyl-C(=O)—; R$^O$—(C$_1$-C$_6$)alkyl-S(=O)$_2$—; R$^O$—O—(C$_1$-C$_6$)alkyl-; R$^O$—C(=O)—(C$_1$-C$_6$)alkyl-; R$^O$—S(=O)$_2$—(C$_1$-C$_6$)alkyl-; (C$_2$-C$_6$)alkenyl-; —C(=O)H; —OR$^x$; —S(=O)$_2$R$^x$; halogen; =O; —NR$^X$R$^Y$; or —C(=O)NR$^X$R$^Y$;

R$^X$ and R$^Y$ are the same as or different from each other, and each mean —H; (C$_1$-C$_6$)alkyl that may be substituted with —OH or pyridyl. Also, R$^X$ may be bonded with R$^Y$ and a nitrogen atom to form (C$_3$-C$_8$)heterocycloalkyl.

This preparation method is a method for preparing a benzimidazole compound represented by the formula (1-c) by allowing an aldehyde compound to undergo the reaction with a 1,2-diaminobenzene compound represented by the formula (1-b) that can be obtained by reduction of a compound represented by the formula (1-a).

The step represented by Step 1-1 is a step for reducing a nitro group of the compound represented by the formula (1-a) to an amino group, that can be carried out at normal pressure or under elevated pressure, in a solvent inert to the reaction.

In the step represented by Step 1-2 wherein R' is H, an imidazole ring can be constructed, for example, by allowing an orthoformic ester such as ethyl orthoformate to undergo the reaction with the compound represented by the formula (1-b) in the presence of an acid catalyst.

Furthermore, in the step represented by Step 1-2 wherein R' is not H, for example, a method in which an amino group of the compound represented by the formula (1-a) is preliminarily acylated using a carboxylic acid, an acid chloride, a carboxylic acid anhydride, or the like, and cyclized under heating or in the presence of an acid, a method in which tetraalkyl orthocarbonate, CDI, or BrCN is used instead of an orthoformic ester, or other methods can be exemplified.

Furthermore, as other methods, a method in which a nitrobenzene compound of the formula (1-a) is subject to carbamoylation of its amine moiety, induced into an acylamine compound (1-e), subject to reduction of its nitro group, and cyclized with heat can also be exemplified (Step 1-3, Step 1-4).

All of these reactions can be carried out in a solvent inert to the reaction, or without a solvent, from at room temperature to under heating, or from under heating or under reflux.

<Second Intermediate Preparation Method>

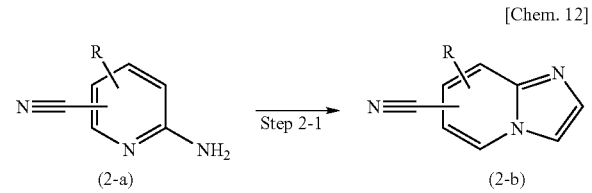

[Chem. 12]

[wherein R has the same meanings as defined above].

This preparation method is a method for preparing an imidazo[1,2-a]pyridine substituted with a nitrile group represented by the formula (2-b), by using a 2-aminopyridine compound represented by the formula (2-a) as a starting material.

The step represented by Step 2-1 is a reaction for constructing an imidazo[1,2-a]pyridine ring by allowing a chloroacetaldehyde or α-chloroketone to undergo the reaction with the compound represented by the formula (2-a).

It is preferably carried out in the presence of a base, and specific examples of the base include alkali carbonates such as Na$_2$CO$_3$ and K$_2$CO$_3$; alkali hydrogen carbonates such as NaHCO$_3$ and KHCO$_3$; alkoxides such as NaOMe, NaOEt, and KO$^t$Bu; tertiary amines such as Et$_3$N and DIPEA; and organic amines such as DBU, pyridine, and lutidine.

All of these reactions can be carried out in a solvent inert to the reaction, or without a solvent, from at room temperature to under heating, or under heating with reflux.

<Third Intermediate Preparation Method>

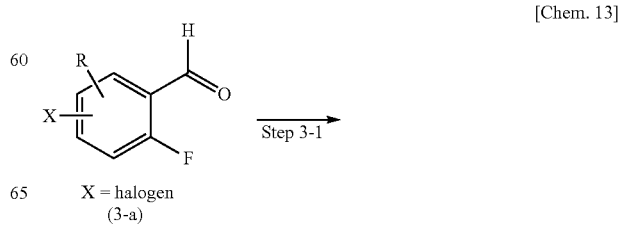

[Chem. 13]

X = halogen
(3-a)

-continued

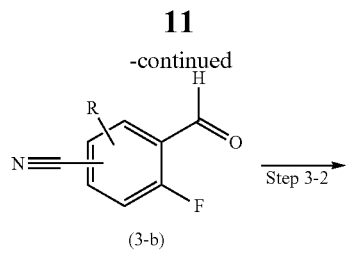

(3-b)

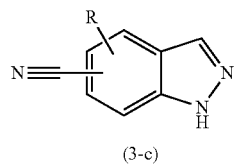

(3-c)

[wherein R has the same meanings as defined above.]

This preparation method is a method for preparing an indazole compound represented by the formula (3-c) by allowing a hydrazine hydrate with a nitrile group to undergo the reaction with a cyanobenzene compound represented by the formula (3-b) obtained by substituting a halogen group of a compound represented by the formula (3-a).

The step represented by Step 3-1 is a reaction for substituting a halogen bonding with an aromatic ring with a nitrile group. It is exemplified by a method for reaction of $Zn(CN)_2$ in the presence of tetrakistriphenylphosphine palladium (0), a method for allowing TMEDA and Pd catalysts to undergo the reaction in the presence of $Na_2CO_3$ in DMA, and a method for allowing KCN, NaCN, or the like to undergo the reaction instead of $Zn(CN)_2$. Usually, the compound represented by the formula (3-b) can be obtained by reacting the compound represented by the formula (3-a) with tris(dibenzylideneacetone)dipalladium (0), 1'-bis(diphenylphosphino)ferrocene, and $Zn(CN)_2$.

Here, examples of the leaving group include halogen such as Br and Cl; methanesulfonyloxy, ethanesulfonyloxy, benzenesulfonyloxy, p-toluenesulfonyloxy, and trifluoromethanesulfonyloxy.

The step represented by Step 3-2 is a reaction for constructing an indazole ring from a cyanobenzaldehyde compound represented by the formula (3-b). Usually, a hydrazine hydrate is used in this reaction, which can be carried out without a solvent, or in a solvent inert to the reaction such as MeOH and toluene, from at room temperature to under heating, or under heating with reflux. In addition, a method using copper cyanide can also be exemplified, and a base such as pyridine may be added. Also, this reaction is preferably carried out under a nitrogen atmosphere.

<Fourth Intermediate Preparation Method>

[Chem. 14]

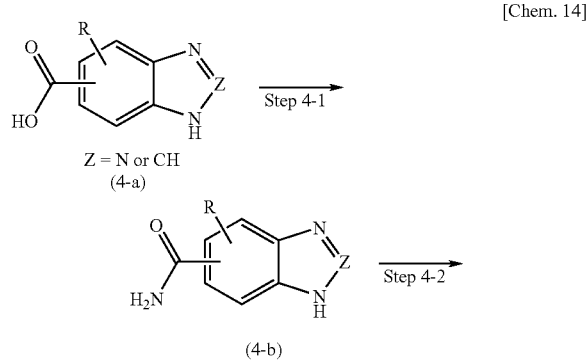

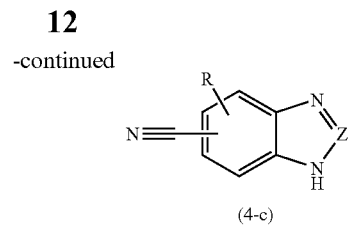

(4-c)

[wherein R has the same meanings as defined above. Z represents —CH= or —N=].

This preparation method is a method for preparing a benzotriazole or benzimidazole compound represented by the formula (4-c) by dehydrating an acid amide compound represented by the formula (4-b), obtained using a carboxylic acid compound represented by the formula (4-a) as a starting material.

The step represented by Step 4-1 is a reaction for condensing a carboxylic acid compound with ammonia represented by the formula (4-a), and constructing an acid amide group represented by the formula (4-b). The compound represented by the formula (4-a) can be used in the reaction as free acid, but a reactive derivative thereof may also be used in the reaction. Examples of the reactive derivative induced from the compound represented by the formula (4-b) include acid halides such as acid chloride and acid bromide; common esters such as methyl ester, ethyl ester, and benzyl ester; acid azides; active esters such as HOBt, p-nitrophenol, and N-hydroxysuccinimide; symmetrical acid anhydrates; a mixed acid anhydrate of a halocarboxylic acid alkyl ester such as an alkyl carbonic acid halide, a pivaloyl halide, and p-toluene sulfonic acid chloride; and a mixed acid anhydrate such as a mixed phosphoric mixed acid anhydrate, such as those obtained by the reaction of diphenylphosphoryl chloride with N-methyl morpholine.

In a case where the compound represented by the formula (4-a) is reacted as a free acid, or without isolation to an active ester, or the like, a condensing agent such as DCC, CDI, DPPA, diethylphosphoryl cyanide, and EDCl/HCl is preferably used.

The reaction solvent varies depending on a reactive derivative or a condensing agent to be used, but the reaction is carried out in an organic solvent inert to the reaction such as hydrocarbon halides, aromatic hydrocarbons, ethers, esters such as EtOAc, acetonitrile, DMF, and DMSO, or a mixed solvent thereof. Also, the reaction is carried out under cooling, from under cooling to at room temperature, or from at room temperature to under heating.

Furthermore, in the reaction, it is in some cases advantageous in advancing the reaction smoothly to carry out the reaction with an excessive amount of ammonia or in the presence of a base such as N-methylmorpholine, trimethylamine, $Et_3N$, DIPEA, N,N-dimethylaniline, pyridine, DMAP, picoline, and lutidine. Pyridine may be used in combination with the solvent.

The step represented by Step 4-2 is dehydration, for which a base may or may not exist, and a dehydrating agent such as trifluoroacetic anhydrate, $POCl_3$, and $P_2O_5$ may be used.

Furthermore, in a case for synthesizing a condensed, intermediate heterocycle other than those described in the above-described intermediate preparation methods, the methods described in Reference Examples or Examples in the present specification, or equivalent methods may be employed, or additionally, well-known methods or methods apparent to a person skilled in the art can also be used for the preparation.

<First Preparation Method>

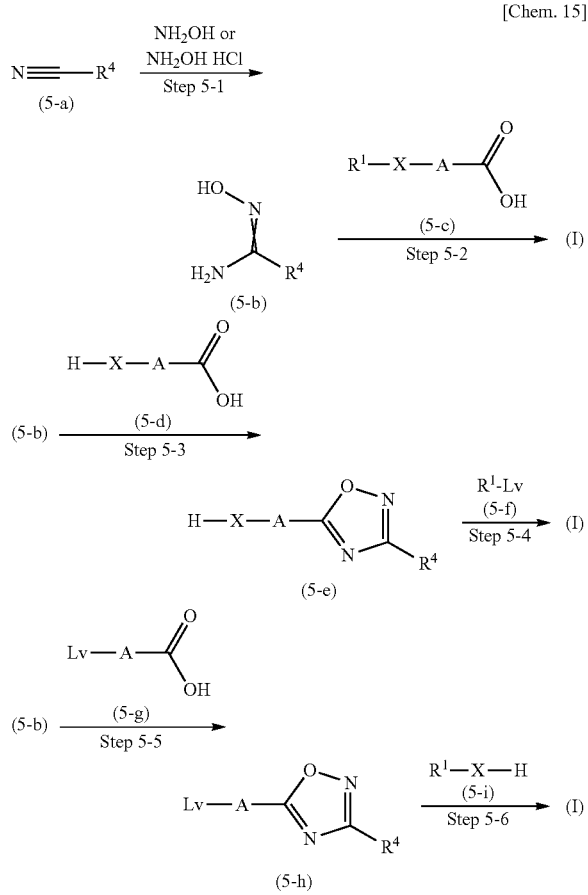

[Chem. 15]

[wherein A, X, $R^1$, and $R^4$ are as described above. Lv represents a leaving group. A carboxylic acid represented by the formula (5-c), (5-d), and (5-g) can be purchased as a commercially available product, or prepared to a commercially available product].

This preparation method is a method for preparing the compound of the present invention represented by the formula (I) by reacting a hydroxyamidine represented by the formula (5-b) obtained by allowing hydroxylamine to undergo the reaction with an aromatic nitrile compound represented by the formula (5-a), with a carboxylic acid represented by the formula (5-c).

In a step represented by Step 5-1, the hydroxyamidine represented by the formula (5-b) can be prepared by allowing a free hydroxylamine or hydroxylamine hydrochloride to undergo the reaction in the presence of a base.

This reaction can be carried out in a solvent inert to the reaction. Specific examples of the solvent include alcohols such as MeOH, EtOH, and i-PrOH; aromatic hydrocarbons such as toluene and xylene; ethers such as ether, THF, dioxane, and diethoxyethane; halogenated hydrocarbons such as dichloromethane, 1,2-dichloroethane, chloroform, and carbon tetrachloride; acetonitriles; aprotic polar solvents such as DMF, 1,3-dimethyl-2-imidazolidinone, and DMSO; water; or a mixed solvent thereof. Usually, alcohols are used in the reaction. As described above, in a case where hydroxylamine hydrochloride is used in this reaction, the reaction is preferably used in the presence of a base, and specific examples of the base include alkali carbonates such as $Na_2CO_3$ and $K_2CO_3$; alkali hydrogen carbonates such as $NaHCO_3$ and $KHCO_3$; alkoxides such as NaOMe, NaOEt, and KO$^t$Bu; tertiary amines such as $Et_3N$ and DIPEA; and organic amines such as DBU, pyridine, and lutidine. The reaction temperature varies depending on the kinds of the starting material compounds, the reaction conditions, or the like, but the reaction can be carried out usually from at room temperature to at about a reflux temperature of the solvent. Typically, in the presence of a base such as $Na_2CO_3$, the reaction can be carried out in an organic solvent inert to the reaction, such as MeOH, from at room temperature to under heating.

The step represented by Step 5-2 consists of two steps, i.e., a step of acylation of a hydroxyamidine product, and a step of a cyclization reaction in this order. The acylation step can be carried out in the following manner. The compound represented by the formula (5-c) can be used in the reaction as a free acid, but a reactive derivative thereof may also be used in the reaction. Examples of the reactive derivative include acid halides such as acid chloride and acid bromide; common esters such as methyl ester, ethyl ester, and benzyl ester; acid azides; active esters such as HOBt, p-nitrophenol, and N-hydroxysuccinimide; symmetrical acid anhydrides; a mixed acid anhydride of a halocarboxylic acid alkyl ester such as an alkyl carbonic acid halide, a pivaloyl halide, and p-toluene sulfonic acid chloride; and a mixed acid anhydride such as a mixed phosphoric mixed acid anhydride, such as those obtained by the reaction of diphenylphosphoryl chloride with N-methyl morpholine.

In a case where the compound represented by the formula (5-c) is reacted as a free acid, or without isolation to an active ester, or the like, a condensing agent such as DCC, CDI, DPPA, diethylphosphoryl cyanide, and EDCl/HCl is preferably used.

The reaction solvent varies depending on a reactive derivative or a condensing agent to be used, but the reaction is carried out in an organic solvent inert to the reaction such as hydrocarbon halides, aromatic hydrocarbons, ethers, esters such as EtOAc, acetonitrile, DMF, and DMSO, or a mixed solvent thereof, under cooling, from under cooling to at room temperature, or from at room temperature to under heating.

In the reaction, the reaction may be smoothly advanced in some cases to carry out the reaction in the presence of a base such as N-methylmorpholine, trimethylamine, $Et_3N$, DIPEA, N,N-dimethylaniline, pyridine, DMAP, picoline, and lutidine. Also, pyridine may be used in combination with the solvent. An acylated product as an intermediate can be purified by isolation, and heated in an organic solvent inert to the reaction, such as EtOH, dioxane, toluene, and water. Usually, this two-step reaction can be carried out in one operation, by heating or microwave-radiating the product as it is or as a reaction mixture, after acylation.

Specific examples of the solvent include aromatics such as toluene, xylene, and pyridine; ethers such as diethyl ether, THF, dioxane, and diethoxyethane; halogenated hydrocarbons such as dichloromethane, 1,2-dichloroethane, chloroform, and carbon tetrachloride; acetonitriles; aprotic polar solvents such as DMF, DMA, 1,3-dimethyl-2-imidazolidinone, NMP, and DMSO; water; or a mixed solvent thereof. The reaction temperature varies depending on the kinds of the starting material compounds, the reaction conditions, or the like, but the reaction can be carried out usually from at room temperature to under heating.

In a case where X represents —O— or —NH—, synthesis can be made by the following preparation method.

The steps represented by Step 5-3 and Step 5-5 can be carried out in the same manner as the step represented by Step 5-2.

The steps represented by Step 5-4 and Step 5-6 are steps for preparing the compound of the present invention represented by the formula (I) by allowing phenol, aniline, alcohol, or amine represented by the formula (5-e) or the formula (5-i) to undergo the reaction with a compound having a leaving group, represented by the formula (5-f) or the formula (5-h). Here, examples of the leaving group include halogens such as chlorine and bromine; and sulfonyloxy such as methanesulfonyloxy, ethanesulfonyloxy, benzenesulfonyloxy, p-toluenesulfonyloxy, p-nitrobenzenesulfonyloxy, and trifluoromethanesulfonyloxy.

The reaction is carried out at normal pressure or under elevated pressure, without a solvent or in an appropriate solvent.

Specific examples of the solvent include aromatic hydrocarbons such as toluene and xylene; ketones such as acetone and methylethylketone; ethers such as ether, THF, dioxane, and diethoxyethane; alcohols such as MeOH, EtOH, i-PrOH, and n-BuOH; halogenated hydrocarbons such as dichloromethane, 1,2-dichloroethane, chloroform, and carbon tetrachloride; acetonitriles; aprotic polar solvents such as DMF, 1,3-dimethyl-2-imidazolidinone, NMP, and DMSO; water; or a mixed solvent thereof. This reaction is preferably used in the presence of a base, and specific examples of the base include NaH; alkali carbonates such as $Na_2CO_3$ and $K_2CO_3$; alkali hydrogen carbonates such as $NaHCO_3$ and $KHCO_3$; alkoxides such as NaOMe, NaOEt, and KO$^t$Bu; tertiary amines such as $Et_3N$, tributylamine, and DIPEA; and organic amines such as DBU, pyridine, and lutidine, but an excessive amount can be combined in an amine represented by the formula (5-e) or the formula (5-i). The reaction temperature varies depending on the kinds of the starting material compounds, the reaction conditions, or the like, but the reaction can be carried out usually from at room temperature to at about a reflux temperature of the solvent. Usually, the reaction can be carried out in the presence of a base such as NaH and $Na_2CO_3$, in an organic solvent inert to the reaction, such as DMF and DMA, from at $-10°$ C. to under heating. Also, the amine represented by the formula (5-e) or the formula (5-i) can be provided for the reaction as a salt thereof. In addition, a microwave may be radiated under heating for the preparation.

Moreover, several compounds represented by the formula (I) can be prepared by any combination of well-known processes that can be usually employed by a person skilled in the art, such as well-known alkylation, acylation, substitution reaction, oxidation, reduction, hydrolysis, deprotection, and halogenation from the compound of the present invention as prepared in the above-described manner.

For example, for alkylation, the alkylation reaction that can be usually used by a person skilled in the art can be employed, which can be carried out in an organic solvent inert to the reaction, such as ethers; aromatic hydrocarbons; halogenated hydrocarbons such as dichloroethane, dichloroethane, and chloroform; DMF, acetonitriles; and aprotic polar solvents, under cooling, from under cooling to at room temperature, or from at room temperature to under heating, in the presence of a base such as NaH; alkali carbonates; alkali hydrogen carbonates; alkoxides; tertiary amines; and organic bases.

Furthermore, for example, for acylation, the acylation reaction that can be usually used by a person skilled in the art can be employed, which can be particularly carried out in the presence of HOBt, in a solvent varying depending on a condensing agent such as EDCl/HCl or CDI, and diphenylphosphorylcyanide, in a solvent varying depending on the reaction condition, but usually in an organic, inert solvent such as ethers; aromatic hydrocarbons; halogenated hydrogen such as dichloromethane, dichloroethane, and chloroform; esters such as EtOAc; acetonitriles; and aprotic solvents, under cooling, from under cooling to at room temperature, or from at room temperature to under heating.

Thus prepared compound is purified by isolation, as it is, or as a salt thereof after a salt-forming treatment by a conventional method. The purification by isolation is carried out by applying common chemical operations such as extraction, concentration, removal by distillation, crystallization, filtration, recrystallization, and various types of chromatography.

Various types of the isomers can be isolated by a conventional method, taking advantage of the difference in the physiochemical properties among the isomers. For example, a racemic mixture can be induced into optically pure isomers, for example, by a general resolution method for racemic products, such as an optical resolution method for inducing diastereomer salts with general, optically active acids such as tartaric acid. Also, the diastereomer mixture can be separated, for example, by fractional crystallization, or various types of chromatography. Furthermore, the optically active compounds can also be prepared by using the corresponding, optically active starting materials.

The actions of the compounds of the present invention were confirmed by the following pharmacological tests.

Experimental Example 1

Test for Confirming an $S1P_1$ Agonist Activity

1) Evaluation of a Receptor Agonist Activity by a GTP [$\gamma$-$^{35}$S] Bond Assay Using the Membrane of a Human $S1P_1$ Expressing Cell The in vitro $S1P_1$ agonist activity of the compound of the present invention was evaluated by the increase in the functional bonding activity into the G-Protein of a GTP[$\gamma$-$^{35}$S] using the membrane of a human $S1P_1$ expressing cell. A cDNA encoding a human $S1P_1$ was cloned from a human colorectal cDNA library, and introduced to an expression vector pcDNA3.1 to construct a $S1P_1$-pcDNA3.1. Then, by Lipofectamine 2000 (GIBCO), the $S1P_1$-pcDNA3.1 was transfected into a CHO cell, and cultured in a Ham's F-12 culture medium containing 10% fetal bovine serum, 100 U/mL Penicillin, 100 μg/mL Streptomycin, and 1 mg/mL G418 disulfate, to obtain a stable, G418-resistant strain. The cultured human $S1P_1$ expressing cells were isolated in a 1 mM EDTA/2Na-containing PBS, and disrupted under ice-cooling by a homogenizer made of glass in a 1 mM Tris HCl (pH 7.4) buffer solution containing 0.1 mM EDTA and a protein inhibitor. It was centrifuged at 1,400×10 min, and a supernatant was further centrifuged at 4° C. for 60 min at 100,000×g, and suspended in a 10 mM Tris HCl (pH 7.4) buffer solution containing 1 mM EDTA. The obtained membrane (0.13 mg/mL) and 50 pM GTP[$\gamma$-$^{35}$S] (NEN; inactive 1250 Ci/mmol) were reacted in a 20 mM HEPES (pH 7.0) buffer solution (total amount: 150 μL) containing 100 mM NaCl, 10 mM $MgCl_2$, 0.1% fatty acid-free BSA, and 5 μM GDP for 1 hour together with the compound of the present invention ($10^{-12}$ to $10^{-5}$ M), and then a membrane was recovered on a GF-C plate with a Cell Harvester (Packard, FilterMate). The FilterMate was dried at 50° C. for 60 min, and Microscinti-o (Packard) was added thereto for measurement by a liquids scintillation counter for a microplate (Packard, TOP count). For evaluation of the human $S1P_1$ agonist activity of the compound of the present invention and the comparative compound, the percentages with the rate of a maximum reaction to make the GTP[$\gamma$-$^{35}$S] bonds saturated in the presence of the compound being set at 100%, and the rate of the reaction of the GTP[$\gamma$-$^{35}$S] bonds in the absence of the compound being set at 0% was used, a non-linear regression curve was plotted, and a concentration to cause an agonist activity operating 50% of the maximum reaction was defined as an $EC_{50}$ value (nM).

TABLE 1

| Ex | $S1P_1$ $EC_{50}$ |
|---|---|
| 2 | 13 |
| 5 | 5.5 |
| 6 | 1.2 |
| 8 | 5.4 |
| 12 | 4.7 |
| 15 | 2.1 |
| 23 | 6.8 |
| 26 | 4.7 |
| 37 | 5.4 |
| 48 | 6.5 |
| 51 | 13 |
| 53 | 5.8 |
| 54 | 2.3 |
| 59 | 3.8 |
| 60 | 2.1 |
| 64 | 5.7 |
| 65 | 4.0 |
| 67 | 3.7 |
| 81 | 5.9 |
| 87 | 3.7 |
| 106 | 8.7 |
| 110 | 6.2 |
| 119 | 4.3 |
| 120 | 4.6 |
| 121 | 12 |
| 143 | 5.4 |
| 147 | 3.2 |
| 151 | 11 |
| 152 | 7.6 |
| 158 | 1.8 |
| 163 | 1.9 |
| 164 | 2.8 |
| 173 | 4.3 |
| 181 | 4.7 |
| 182 | 4.2 |

TABLE 1-continued

| Ex | $S1P_1$ $EC_{50}$ |
|---|---|
| 193 | 6.8 |
| 194 | 2.0 |
| 196 | 5.3 |
| 197 | 3.3 |
| 199 | 5.0 |
| 200 | 3.6 |

As a result, it can be confirmed that the compound of the present invention has an $S1P_1$ agonist activity.

2) Evaluation of Peripheral Blood Lymphopenia in Rat

The peripheral blood lymphopenia in rat was measured at 24 hours after oral administration in the following manner. Six- to ten-week-old male Lewis rats (Japan Charles river laboratories) were randomly divided into the groups (n=3), and the compound of the present invention was suspended in 0.5% methyl cellulose-containing distilled water, and orally administered with a sonde. At 24 hours after administration, under ether anesthesia, 0.2 ml of blood was collected from ocular fundus. To the blood sample were immediately added EDTA/4K and heparin to prevent clotting, and the number of the lymphocytes in blood was measured with an automatic haematology analyzer (Sysmex Corp.; XT-2000i). For the reduction of the number of the lymphocytes in peripheral blood by the compound of the present invention, the percentage with the number of the lymphocytes in groups administered with 0.5% methyl cellulose-containing distilled water being set at 100%, as performed at the same time was used, and the dose to cause 50% reduction of the number of the lymphocytes in peripheral blood by administration of the compound of the present invention was defined an $ED_{50}$ value (mg/kg).

For the comparative compounds 1 and 2 as described in the pamphlet of International Publication No. WO2004/103279, the comparative compound 3 as thought to be encompassed in the claim of the pamphlet of International Publication No. WO2005/032465, and the compound of Example 119, the $ED_{50}$ values at 24 hours after administration were compared for the reduction of the number of the lymphocytes in peripheral blood in rat.

TABLE 2

| Compound | Structure | $ED_{50}$ value after 24 hours |
|---|---|---|
| Ex 119 | 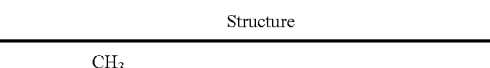 | 0.071 mg/kg |
| Comparative Compound 1 | 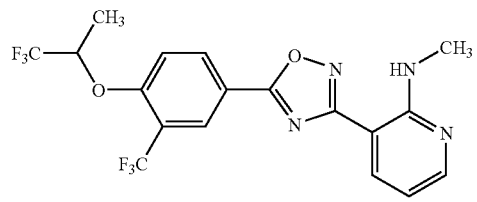 | 1.4 mg/kg |

TABLE 2-continued

| Compound | Structure | ED$_{50}$ value after 24 hours |
|---|---|---|
| Comparative Compound 2 | [structure: F$_3$C-CH(CH$_3$)-O-phenyl(3-CF$_3$)-oxadiazole-pyridine-NH$_2$] | 8.8 mg/kg |
| Comparative Compound 3 | [structure: F$_3$C-CH(CH$_3$)-O-phenyl(3-CF$_3$)-oxadiazole-phenyl(CH$_3$, Cl)] | 3.7 mg/kg |

Moreover, for the comparative compound 4 as thought to be encompassed in the claim of the pamphlet of International Publication No. WO2004/103279, the comparative compounds 5 as described in the pamphlet of International Publication No. WO2004/103279, and the compound of Example 199, the ED$_{50}$ values at 24 hours after administration were compared for the reduction of the number of the lymphocytes in peripheral blood in rat.

As a result, it was demonstrated that the compounds of Example 119 and Example 199 show a high ED$_{50}$ value even after 24 hours, indicating persistence.

Since the compound of the present invention has an S1P$_1$ agonist effect, it is useful as an active ingredient of an agent for treating or an agent for preventing a disease caused by unfavorable lymphocytic infiltration, for example, an autoimmune disease such as graft rejection in the transplantation of an organ, bone marrow, or a tissue or a graft-versus-host

TABLE 3

| Compound | Structure | ED$_{50}$ value after 24 hours |
|---|---|---|
| Ex 199 | [structure: F$_3$C-CH(CH$_3$)-O-phenyl(Cl)-oxadiazole-benzimidazole; HCl] | 0.26 mg/kg |
| Comparative Compound 4 | [structure: F$_3$C-CH(CH$_3$)-O-phenyl(Cl)-oxadiazole-pyridine-NHCH$_3$; HCl] | >10 mg/kg |
| Comparative Compound 5 | [structure: F$_3$C-CH(CH$_3$)-O-phenyl(Cl)-oxadiazole-pyridine-NHCH$_3$; HCl] | >10 mg/kg | disease, rheumatic arthritis, multiple sclerosis, systemic lupus erythematosus, nephrotic syndrome, encephalomeningitis, myasthenia gravis, pancreatitis, hepatitis, nephritis, diabetes, pulmonary disorder, asthma, atopic dermatitis, inflammatory bowel disease, atherosclerosis, or ischemia-reperfusion injury or an inflammatory disease, and further, a disease caused by the abnormal growth or accumulation of cells, such as cancer and leukemia.

Furthermore, the compound of the present invention is useful to treat and/or prevent the following diseases, based on the agonist activity against an $S1P_1$.

It is useful to treat and/or prevent inflammatory or hyperplastic skin diseases such as psoriasis, contact dermiatitis, eczematoid dermatitis, seborrheic dermatitis, lichen planus, pemphigus, pemphigoid, epidermolysis bullosa, hives, vascular edema, obliterans, erythema, eosinophilia of skin, lupus erythematosus, acne, and alopecia areata, or expression of skin diseases through an immune system; autoimmune diseases or allergic diseases of eyes, such as keratoconjunctivitis, vernal conjunctivitis, allergic conjunctivitis, uveitis associated with Behcet disease, keratitis, Herpesviral keratitis, Keratoconus keratitis, corneal epithelial dystrophies, corneal leukoma, ocular pemphigus, Mooren's ulcer, scleritis, Graves' ophthalmopathy, Vogt-Koyanagi-Harada disease, leratoconjunctivitis sicca (dry eye), vesicle, iridocyclitis, sarcoidosis, and ophthalmic diseases inendocrine glands; reversible obstructive lung diseases (asthma (for example, bronchial asthma, allergic asthma, intrinsic asthma, extrinsic asthma, and dirt asthma), in particular, chronic or difficult asthma (for example, late-onset asthma, and airway diseases); mucous or angiitis (for example, gastric ulcers, ischemic or thrombotic Vascular Injuries, age-related maculopath, diabetic maculopath, ischemic bowel disease, bowel disease, necrotizing enteritis, intestinal tract lesion by heat burn, and diseases by a transmitter of a Leukotriene B4); inflammatory intestine or allergic diseases of intestine, including, for example, proctitis, eosinophilic enteritis, mastocytosis, celiac disease, Crohn's disease, and ulcerative colitis; food-related allergic diseases expressing the conditions on a site that is remote from the gastro-intestinal tract including, for example, migraine, rhinitis, and eczema; autoimmune diseases or inflammatory diseases including, for example, primary mucous edema, autoimmune atrophic gastritis, precocious climacteric period, juvenile diabetes, pemphigus vulgaris, pemphigoid, sympathetic ophtalmolima, lens-induced uveitis, paroxysmal Leukopenia, chronic active hepatitis, paroxysmal liver cirrhosis, discoid lupus erythematosus, Sjoegren syndrome, autoimmune orchitis, arthritis (for example, modified arthritis), and polychondritis; renal diseases including, for example, membranous nephrophathy, membranoproliferative nephritis, focal global glomerulosclerosis, crescent nephritis, glomerular nephritis, IgA nephropathy, tubulopathy interstitial nephritis, and diabetic nephropathy. Furthermore, the compound of the present invention is also useful to treat and/or prevent liver diseases (for example, immunogenic diseases (for example, autoimmune lever diseases, chronic autoimmune lever diseases such as primary biliary cirrhosis., sclerosing cholangitis, and the like), partial hepatic dissection, acute hepatic necrosis (for example, necrosis caused by toxin, viral hepatitis, shock, anoxia, or the like), Type B hepatitis, non-Type A hepatitis, cirrhosis, heptatic failure (for example, fulminant hepatitis, late-onset hepatitis, hepatic failure (acute hepatic failure or chronic hepatic disease)), and the like.

In addition, compound of the present invention can be administered as an $S1P_1$ agonist alone, or in combination with at least one agent, in the same dose or different doses, through the same or different administration routes. Examples of the agent that can be combined include, but not limited thereto, cyclosporin A, tacrolimus, sirolimus, everolimus, mycophenolate, azathioprine, brequinar, Leflunomide, fingolimod, an anti-IL-2 receptor antibody (for example, daclizumab), an anti-CD3 antibody (for example, OKT3), anti-T cell immunoglobulin (for example, AtGam), belatacept, abatacept, cyclophosphamide, β-interferone, aspirine, acetaminophen, ibuprofen, naproxen, piroxicam, and anti-inflammatory steroid (for example, prednisolone, and dexamethasone).

A preparation containing the compound represented by the formula (I), or one, or two or more kinds of the salts thereof as effective ingredients are prepared by using a carrier, an excipient or other additives that are usually used in the preparation of medicines.

Administration may be made in any one form for either oral administration by tablets, pills, capsules, granules, powders, and solutions, or for parenteral administration by injections for intravenous injection, and intramuscular injection, suppositories, percutaneous preparations, transnasal preparations, inhalations or the like. The dose is appropriately decided in response to an individual case by taking the symptoms, age and sex of the subject and the like into consideration, but is usually from about 0.001 mg/kg to about 100 mg/kg per day per adult in the case of oral administration, and this is administered in one portion or dividing it into 2 to 4 portions. Also, in the case of intravenous administration according to the symptoms, it is administered usually within the range of from 0.0001 mg/kg to 10 mg/kg per day per adult, once a day or two or more times a day. In addition, in the case of inhalation, it is administered generally within the range of from 0.0001 mg/kg to 1 mg/kg per adult, once a day or two or more times a day.

Regarding the solid composition of the present invention for oral administration, tablets, powders, granules, or the like are used. In such a solid composition, one or more active substances are mixed with at least one inactive excipient such as lactose, mannitol, glucose, hydroxypropylcellulose, microcrystalline cellulose, starch, polyvinyl pyrrolidone, and aluminum magnesium silicate. In a conventional method, the composition may contain inactive additives, for example, a lubricant such as magnesium stearate, a disintegrator such as carboxymethylstarch sodium, or a solubilizing agent. As occasion demands, tablets or pills may be coated with a sugar coating, or a gastric or enteric coating agent.

The liquid composition for oral administration include pharmaceutically acceptable emulsions, solutions, suspensions, syrups, elixirs, and the like, and contains generally used inert solvents such as purified water and ethanol. In addition to the inert solvent, this composition may contain an auxiliary agent such as a solubilizing agent, a moistening agent, and a suspending agent, a sweetener, a corrective, an aromatic, and an antiseptic.

Injections for parenteral administration include sterile aqueous or non-aqueous solutions, suspensions and emulsions. Examples of the aqueous solvent include distilled water for injection and physiological saline. Examples of the non-aqueous solvent include propylene glycol, polyethylene glycol, plant oils such as olive oil, alcohols such as ethanol, and Polysorbate 80 (Pharmacopeia). Such a composition may further contain a tonicity agent, an antiseptic, a moistening agent, an emulsifying agent, a dispersing agent, a stabilizing agent, and a solubilizing agent. These are sterilized, for example, by filtration through bacteria retaining filter, blending of bactericides, or irradiation. In addition, these can also be used by producing a sterile solid composition, and dissolving or suspending it in sterile water or a sterile solvent for injection prior to its use.

Regarding a transmucosal agent such as an inhalations and a transnasal agent, those in a solid, liquid or semi-solid state are used, and may be produced in accordance with a conventionally known method. For example, an excipient such as lactose and starch, and also a pH adjusting agent, an antiseptic, a surfactant, a lubricant, a stabilizer, a thickener, and the like may be optionally added thereto. For their administration, an appropriate device for inhalation or blowing may be used. For example, a compound may be administered alone or as a powder of formulated mixture, or as a solution or suspension by combining it with a pharmaceutically acceptable carrier, using a conventionally known device or sprayer, such as a measured administration inhalation device. The dry powder inhaler or the like may be for single or multiple administration use, and a dry powder or a powder-containing capsule may be used. Alternatively, this may be in a form such as a high pressure aerosol spray which uses an appropriate propellant, for example, a suitable gas such as chlorofluoroalkane, hydrofluoroalkane, and carbon dioxide.

The external agent includes ointments, plasters, creams, jellies, paps, sprays, lotions, eye drops, eye ointments, and the like. The external agent contains ointment bases, lotion bases, aqueous and non-aqueous liquids, suspensions, emulsions, and the like, for general use. Examples of the ointment or lotion bases include polyethylene glycol, propylene glycol, white Vaseline, white beeswax, polyoxyethylene hardened castor oil, glycerin monostearate, stearyl alcohol, cetyl alcohol, lauromacrogol, and sorbitan sesquioleate.

EXAMPLE

Hereinafter, the compounds of the present invention will be described in more detail with reference to Examples. The present invention is not limited to the inventions as described in the following Examples. The preparation methods of the starting material compounds are shown in Preparation Examples.

[In the following tables, Pr represents Preparation Example No., and Structure represents a structural formula. As the abbreviation symbols in the structural formulae, Me represents a methyl group, and Et represents an ethyl group. Crisscross double bond represents a cis/trans mixture, and if the section of Data describes only the numbers, it shows MS data. MS represents mass spectrometry data. In the tables, RT refers to a retention time in high performance liquid chromatography (HPLC), and M represents minutes. The condition for HPLC is as follows: column: Intertsil ODS-3 4.6×150 mm, eluent 0.01M $KH_2PO_4$ aq./MeCN(3:7), flow rate: 1.0 ml/min, detection wavelength: 254 nm. If $^1$H-NMR data are described in the tables, tetramethylsilane is used as an internal standard, and unless otherwise specifically mentioned, δ (ppm) (integrated values, variation patterns) of the signals in $^1$H-NMR using DMSO-$d_6$ as a measurement solvent is shown. Abbreviation symbols have the same meanings as follows. S: singlet, d: doublet, t: triplet q: quartet dd: double doublet, ddd: double double doublet, dt: double triplet, dm: double multiplet, br: broad, brs: broad singlet, Hz: Hertz, CDCl$_3$: deuterated chloroform, DMSO-$d_6$: dimethylsulfoxide-$d_6$, and in the present specification, NMR represents $^1$H-NMR: proton nuclear magnetic resonance. The same shall apply hereinafter].

Preparation Example 1

Imidazo[1,2-a]pyridine-7-carbonitrile hydrochloride (1.50 g), hydroxylamine hydrochloride (301 mg), and Na$_2$CO$_3$ (3.50 g) were stirred at 60° C. for 6 hours in CH$_3$OH (57 ml). The reaction solution was cooled and concentrated, and completion of the reaction was confirmed by LC-MS. To the residue was added water, followed by extraction twice with EtOAc. The organic layer was washed with water and saturated brine, dried over anhydrous MgSO$_4$, and then filtered, and the filtrate was concentrated to obtain N'-hydroxyimidazo[1,2-a]pyridine-7-carboxamide (850 mg) as a white solid.

The compounds shown in Pr 1-1 through Pr 1-17 were prepared in the same manner as in Preparation Example 1.

TABLE 4

| Pr | Structure | MS |
|---|---|---|
| 1 | 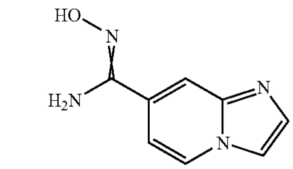 | 177 |
| 1-1 | 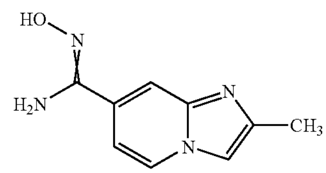 | 191 |
| 1-2 | 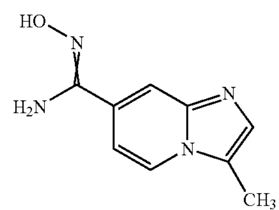 | 191 |
| 1-3 | 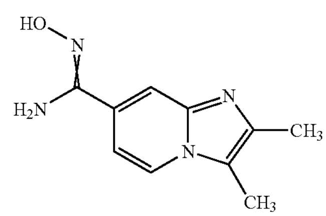 | 205 |
| 1-4 | 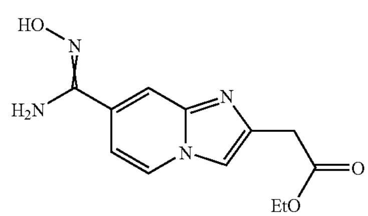 | 263 |
| 1-5 | 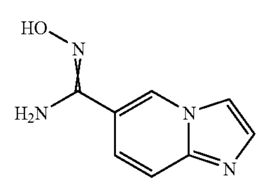 | 177 |

TABLE 4-continued

| Pr | Structure | MS |
|---|---|---|
| 1-6 | 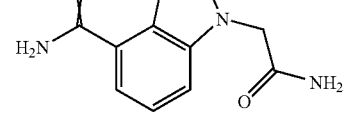 | 191 |
| 1-7 | 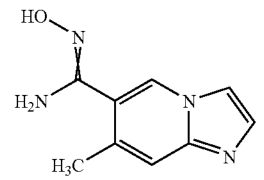 | RT: 1.79 M |
| 1-8 | 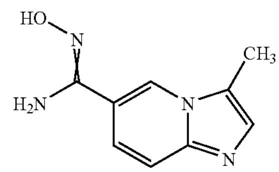 | 191 |
| 1-9 | 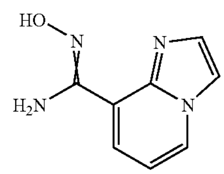 | 177 |
| 1-10 | 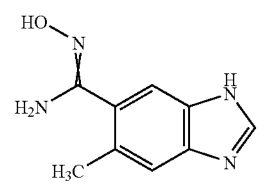 | 191 |
| 1-11 | 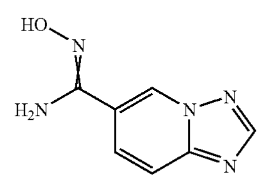 | RT: 1.64 M |
| 1-12 | 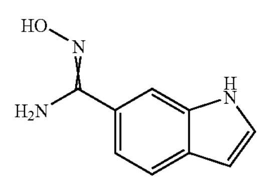 | RT: 1.60 M |
| 1-13 | 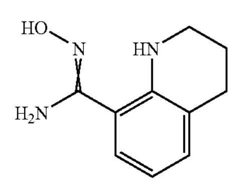 | 192 |

TABLE 4-continued

| Pr | Structure | MS |
|---|---|---|
| 1-14 | 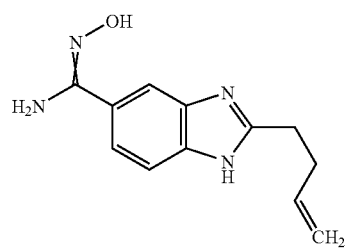 | 233 |
| 1-15 | | 231 |
| 1-16 | | 391 |
| 1-17 | | |

Preparation Example 2

In a 50 ml reaction vessel, to a solution of 1H-indole-4-carbonitrile (5.00 g) in CH$_3$OH (100 ml) was added hydroxylamine (50% aqueous solution) at room temperature, followed by refluxing for 15 hours (completion of the reaction was confirmed by TLC). The reaction solution was concentrated under reduced pressure, and azeotroped with toluene three times. The obtained solid was washed with IPE. N'-Hydroxy-1H-indole-4-carboximidamide (6.12 g) was obtained as a white solid.

The compounds shown in Pr 2-1 through Pr 2-26 were prepared in the same manner as in Preparation Example 2.

TABLE 5

| Pr | Structure | MS |
|---|---|---|
| 2 | 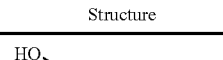 | 176 |

TABLE 5-continued

| Pr | Structure | MS |
|---|---|---|
| 2-1 | N-hydroxy-8-methylimidazo[1,2-a]pyridine-7-carboxamidine | 191 |
| 2-2 | N-hydroxy-2,3-dimethylimidazo[1,2-a]pyridine-6-carboxamidine | 205 |
| 2-3 | ethyl 2-(6-(N-hydroxycarbamimidoyl)imidazo[1,2-a]pyridin-2-yl)acetate | 263 |
| 2-4 | N-hydroxy-1H-benzimidazole-6-carboxamidine | 177 |
| 2-5 | N-hydroxy-7-methyl-1H-benzimidazole-6-carboxamidine | 191 |
| 2-6 | N-hydroxy-2-methyl-1H-benzimidazole-6-carboxamidine | 191 |
| 2-7 | 2-ethoxy-N-hydroxy-1H-benzimidazole-6-carboxamidine | 221 |
| 2-8 | 2-amino-N-hydroxy-1H-benzimidazole-5-carboxamidine | 192 |
| 2-9 | N-hydroxy-2-oxo-2,3-dihydro-1H-benzimidazole-5-carboxamidine | 193 |
| 2-10 | N-hydroxy-7-methyl-1H-benzimidazole-5-carboxamidine | 191 |
| 2-11 | N-hydroxyquinoline-6-carboxamidine | 188 |

TABLE 6

| Pr | Structure | MS |
|---|---|---|
| 2-12 | N-hydroxy-4-methylquinoline-3-carboxamidine | 202 |
| 2-13 | N-hydroxy-1H-indazole-5-carboxamidine | — |
| 2-14 | N-hydroxy-1H-indazole-6-carboxamidine | RT: 1.68 M |
| 2-15 | N-hydroxy-1H-pyrrolo[2,3-b]pyridine-5-carboxamidine | 177 |

TABLE 6-continued

| Pr | Structure | MS |
|---|---|---|
| 2-16 | (HO-N=C(NH2)- pyrazolo[3,4-b]pyridine) | NMR below |
| 2-17 | (HO-N=C(NH2)- 3-amino-1H-indazole) | |
| 2-18 | (HO-N=C(NH2)- 1H-benzotriazole) | RT: 1.62 M |
| 2-19 | (HO-N=C(NH2)- imidazo[4,5-b]pyridine) | 200 |
| 2-20 | (HO-N=C(NH2)- benzothiazole) | RT: 1.69 M |
| 2-21 | (HO-N=C(NH2)- 1H-benzotriazole isomer) | RT: 1.62 M |
| 2-22 | (HO-N=C(NH2)- 2-oxindole) | RT: 1.62 M |
| 2-23 | (HO-N=C(NH2)- 7-azaindole) | 177 |
| 2-24 | (HO-N=C(NH2)- 4-chloro-2-methylbenzimidazole) | 225 |
| 2-25 | (HO-N=C(NH2)- imidazo[1,2-a]pyridine) | 177 |
| 2-26 | (HO-N=C(NH2)- 1H-benzimidazole) | 177 |

TABLE 7

| Pr | NMR |
|---|---|
| 2-16 | 5.71(2H, s), 6.47(1H, d), 7.50(1H, d), 7.61(1H, d), 7.93(1H, d), 9.78(1H, s), 11.70(1H, s) |

Preparation Example 3

A suspension of $N^2$-hydroxy-1H-indole-4-carboxamide (1.00 g), 4-fluoro-3-(trifluoromethyl)benzoic acid (1.19 g), and EDCl/HCl (1.32 g) in dioxane (30 ml) was stirred at room temperature for 1 hour, and further heated under reflux for 18 hours. The reaction mixture was concentrated under reduced pressure, chloroform and water were added thereto, followed by stirring. The insolubles were collected by filtration. The organic layer of the mother liquor was washed with water, dried over anhydrous MgSO$_4$, and then filtered, and the filtrate was concentrated under reduced pressure. The insolubles collected by filtration, together with the mother liquor, was purified by silica gel chromatography (n-hexane: EtOAc=80:20). To the objective substance was added acetone, followed by dissolving under heating, and addition with n-hexane, and the precipitated solid was collected by filtration to obtain 4-{5-[4-fluoro-3-(trifluoromethyl)phenyl]-1,2,4-oxadiazol-3-yl}-1H-indole (391 mg) as a white solid.

TABLE 8

| Pr | Structure | MS |
|---|---|---|
| 3 | (4-fluoro-3-(trifluoromethyl)phenyl-1,2,4-oxadiazol-3-yl-1H-indole) | 346 |

Preparation Example 4

N²-{[(5,6-Dichloropyridin-3-yl)carbonyl]oxy}-1H-indole-4-carboxamidine (1.91 g) was added to dioxane (40 ml), followed by heating under reflux for 5 hours. It was concentrated under reduced pressure, and then purified by silica gel column chromatography (EtOAc). To the obtained solid was added acetone, followed by suspension under heating. After being left to be cooled, the insolubles was collected by filtration to obtain 4-[5-(5,6-dichloropyridin-3-yl)-1,2,4-oxadiazol-3-yl]-1H-indole (1.44 g) as pale yellow powders.

TABLE 9

| Pr | Structure | MS |
|---|---|---|
| 4 | (structure) | 331, 329 |

Preparation Example 5

A solution of N²-hydroxy-1H-indole-4-carboxamide (3.42 g) and 4-fluoro-3-(trifluoromethyl)benzoic acid (4.07 g) in THF (70 ml) was cooled to −10° C. or lower, and added with DIC (3.7 ml). After stirring at −15 to −5° C. for 3 hours, the reaction mixture was concentrated under reduced pressure. The residue was suspended in chloroform, and then the insolubles were collected by filtration. The obtained powders were purified by silica gel chromatography (n-hexane:EtOAc=50:50) to obtain N²-{[4-fluoro-3-(trifluoromethyl)benzoyl]oxy}-1H-indole-4-carboxamide (8.40 g) as a white solid.

The compound shown in Pr 5-1 was prepared in the same manner as in Preparation Example 5.

TABLE 10

| Pr | Structure | MS |
|---|---|---|
| 5 | (structure) | 388, 366 |
| 5-1 | (structure) | — |

Preparation Example 6

To a solution of 6-amino-2-methylnicotinonitrile (960 mg) in ethanol (34 ml) was added a 40% aqueous chloroacetaldehyde solution (2.36 ml) at 60° C. The reaction mixture was refluxed for 8 hours. The resulting precipitates were collected by filtration to obtain 5-methylimidazo[1,2-a]pyridine-6-carbonitrile hydrochloride (580 mg) as a white solid.

The compounds shown in Pr 6-1 through Pr 6-11 were prepared in the same manner as in Preparation Example 6.

TABLE 11

| Pr | Structure | MS |
|---|---|---|
| 6 | (structure) HCl | 158 |
| 6-1 | (structure) | 158 |
| 6-2 | (structure) | 158 |
| 6-3 | (structure) | 252 |
| 6-4 | (structure) HCl | 144 |
| 6-5 | (structure) | 172 |
| 6-6 | (structure) | NMR below |
| 6-7 | (structure) | 252 |
| 6-8 | (structure) | 172 |

TABLE 11-continued

| Pr | Structure | MS |
|---|---|---|
| 6-9 | [structure: imidazo[1,2-a]pyridine with CN] | NMR below |
| 6-10 | [structure: methyl-imidazo[1,2-a]pyridine with CN, HCl] | 158 |
| 6-11 | [structure: 3-methyl-imidazo[1,2-a]pyridine with CN] | 158 |

TABLE 12

| Pr | NMR |
|---|---|
| 6-6 | 2.39(3H, s), 7.14(2H, m), 7.92(1H, s), 8.18(1H, s), 8.62(1H, d) |
| 6-9 | 7.48(1H, dd, J = 1.6, 9.3 Hz), 7.74(1H, d, J = 9.3 Hz), 7.76(1H, d, J = 1.6 Hz), 8.06(1H, s), 9.37(1H, s) |

Preparation Example 7

To a solution of 3,4-diaminobenzonitrile (500 mg) in AcOH (10 ml) was added $Ac_2O$ (372 μl) at room temperature. The reaction mixture was refluxed for 15 hours (oil bath at 150° C.). It was cooled to room temperature, and concentrated until the amount of AcOH was reduced to a half. It was neutralized with an aqueous $Na_2CO_3$ solution, and extracted with EtOAc. The organic layer was washed with a saturated aqueous $NaHCO_3$ solution and saturated brine, dried over anhydrous $MgSO_4$, and then filtered, and the filtrate was concentrated. The residue was purified by silica gel column chromatography to obtain 2-methyl-1H-benzimidazole-5-carbonitrile (390 mg) as a pale red one.

TABLE 13

| Pr | Structure | MS |
|---|---|---|
| 7 | [structure: 2-methyl-1H-benzimidazole-5-carbonitrile] | 158 |

Preparation Example 8

A reaction mixture of 4,5-diamino-2-methylbenzonitrile (20 mg) and formic acid (6 ml) was refluxed for 3 hours. The reaction solution was cooled and concentrated. To the residue was added a 1M aqueous NaOH solution, and extracted with EtOAc. The organic layer was dried over anhydrous $MgSO_4$, and then filtered, and the filtrate was concentrated to obtain 5-methyl-1H-benzimidazole-6-carbonitrile as colorless powders.

The compound shown in Pr 8-1 was prepared in the same manner as in Preparation Example 8.

TABLE 14

| Pr | Structure | MS |
|---|---|---|
| 8 | [structure: 5-methyl-1H-benzimidazole-6-carbonitrile] | 158 |
| 8-1 | [structure: 5-bromo-4-methyl-1H-benzimidazole] | 211, 213 |

Preparation Example 9

A solution of 3,4-diaminobenzonitrile (400 mg) in ethyl orthoformate (6.48 ml) was added AcOH (238 mg), followed by stirring at 80° C. for 2 hours. The reaction solution was cooled to room temperature, and partitioned between EtOAc and a 1M aqueous NaOH solution. The organic layer was washed with saturated brine, dried over anhydrous $Na_2SO_3$, and then collected by filtration, and the filtrate was concentrated, and purified by silica gel chromatography to obtain 2-ethoxy-1H-benzimidazole-6-carbonitrile (164 mg) as colorless powders.

TABLE 15

| Pr | Structure | MS |
|---|---|---|
| 9 | [structure: 2-ethoxy-1H-benzimidazole-6-carbonitrile] | 210 |

Preparation Example 10

To a suspension of 3,4-diaminobenzonitrile (400 mg) in $CH_3OH$ (4 ml) was added BrCN (477 mg), followed by stirring at 20° C. for 14 hours. To the reaction mixture was added a 1M aqueous NaOH solution (0.117 ml), followed by concentration. To the residue was added chloroform:$CH_3OH$=10:1 (10 ml), and the resulting insolubles were removed by filtration. The filtrate was concentrated, and the obtained residue was purified by silica gel column chromatography to obtain 2-amino-1H-benzimidazole-6-carbonitrile (311 mg) as pale orange color powders.

TABLE 16

| Pr | Structure | MS |
|---|---|---|
| 10 | [structure: 2-amino-1H-benzimidazole-6-carbonitrile] | 159 |

Preparation Example 11

To a solution of 3,4-diaminobenzonitrile (350 mg) in toluene (5.5 ml) was added CDI (554 mg), followed by stirring at 125° C. for 2 hours. To the reaction mixture was added a 1M aqueous NaOH solution (0.117 ml), followed by extraction with EtOAc. The organic layer was dried over anhydrous MgSO$_4$, and then filtered, and the filtrate was concentrated. It was powdered/washed with IPE/IPA to obtain 2-oxo-2,3-dihydro-1H-benzimidazole-5-carbonitrile (423 mg) as colorless powders.

TABLE 17

| Pr | Structure | NMR |
|---|---|---|
| 11 | [2-oxo-2,3-dihydro-1H-benzimidazole-5-carbonitrile] | 7.07 (1H, d, J = 8.2 Hz), 7.31 (1H, d, J = 1.6 Hz), 7.39 (1H, dd, J = 1.6, 8.2 Hz), 11.12 (2H, br) |

Preparation Example 12

To a mixed solution of N-(4-cyano-2-nitrophenyl)penta-4-enamide (1.0 g) in AcOH/ethanol (1:1, 20 ml) was added iron powders (710 mg). The reaction solution was heated at 110° C. for 3 hours, and then concentrated. To the residue was added chloroform, followed by neutralization with a saturated aqueous NaHCO$_3$ solution. The organic layer was dried over anhydrous MgSO$_4$, and then filtered to remove a desiccant, and the solvent was concentrated under reduced pressure. The residue was purified by silica gel column chromatography to obtain 3-butenyl-1H-benzimidazole-5-carbonitrile (405 mg) as a colorless liquid.

The compounds shown in Pr 12-1 through Pr 12-2 were prepared in the same manner as in Preparation Example 12.

TABLE 18

| Pr | Structure | MS |
|---|---|---|
| 12 | [3-butenyl-1H-benzimidazole-5-carbonitrile] | 220 |
| 12-1 | [benzimidazole ethyl ester] | 266 |
| 12-2 | [benzimidazole ethyl SMe] | 218 |

Preparation Example 13

To a solution of 2-fluoroterephthalonitrile (500 mg) and Et$_3$N (572 μl) in EtOH (20 ml) was added hydrazine (monohydrate), followed by reaction at 60° C. for 16 hours, and concentrated. The residue was washed with diethyl ether to obtain 3-amino-1H-indazole-6-carbonitrile (488 mg) as a yellow solid.

The compound shown in Pr 13-1 was prepared in the same manner as in Preparation Example 13.

TABLE 19

| Pr | Structure | MS |
|---|---|---|
| 13 | [3-amino-1H-indazole-6-carbonitrile] | 157 |
| 13-1 | [indazole carbonitrile] | |

Preparation Example 14

To a suspension of 3-amino-1H-indazole-6-carbonitrile (345 mg) in AcOH was slowly added an aqueous NaNO$_2$ solution (301 mg) at 0° C. It was stirred at room temperature for 2.5 days, and the residue was collected by filtration, and washed with cool water. To the residue were added 0.1M HCl and DME, followed by stirring at 80° C. for 2 hours. The reaction mixture was neutralized with a saturated aqueous NaHCO$_3$ solution, and extracted with EtOAc. The organic layer was dried over anhydrous MgSO$_4$, and concentrated. The residue was purified by silica gel column chromatography (n-hexane:EtOAc=80:20 to 50:50) to obtain 1H-indazole-6-carbonitrile (175 mg) as a yellow solid.

TABLE 20

| Pr | Structure | MS |
|---|---|---|
| 14 | [1H-indazole-6-carbonitrile] | 142 |

Preparation Example 15

Methyl (4-cyano-2-nitrophenyl)acetate (128 mg) was dissolved in AcOH (3.0 ml), followed by addition of iron powders (129 mg), and the reaction solution was stirred in an oil bath at 100° C. for 1.5 hours. It was concentrated to remove AcOH, followed by addition of EtOAc. The brown solid was separated by filtration, and the organic layer was washed with a 1M HCl solution and saturated brine, dried over anhydrous MgSO$_4$, and concentrated. The residue was purified by silica gel column chromatography (chloroform:CH$_3$OH=99:1 to 95:5) to obtain to obtain 2-oxoindoline-6-carbonitrile (52.0 mg) as a pale yellow solid.

TABLE 21

| Pr | Structure | MS |
|---|---|---|
| 15 | (6-cyanoindolin-2-one) | 157 |

Preparation Example 16

To a solution of 6-bromo-2,2-dimethylindanemethylindan-1-one (124 mg) in TFA (4.44 g, 3.0 ml) was added triethylsilane (150 mg, 207 μl) at room temperature. After stirring at room temperature for 2.5 days, to the reaction solution was added water to stop the reaction, followed by washing with water and a saturated aqueous NaHCO₃ solution. The reaction mixture was extracted with EtOAc. The organic layer was dried over anhydrous MgSO₄, and then filtered, and the filtrate was concentrated. The residue was purified by silica gel column chromatography (n-hexane only) to obtain 5-bromo-2,2-dimethylindane (114 mg) as a colorless oil.

TABLE 22

| Rf | Struture | NMR |
|---|---|---|
| 16 | H₃C,H₃C-dimethylindane-Br | 1.09(6H, s), 2.63(2H, s), 2.68(2H, s), 7.13(1H, d), 7.27(1H, dm), 7.36 (1H, m) |

Preparation Example 17

In THF (30 ml), to a mixture of 6-bromo-1-indanone (300 mg) and diazomethane (504 mg, 221 μl) was added 60% NaH (125 mg) at 0° C. It was stirred at room temperature for 3.5 hours, and washed with a saturated NH₄Cl solution. The mixture was extracted with EtOAc, and the organic layer was dried over anhydrous MgSO₄, and then filtered, and the filtrate was concentrated. The residue was purified by silica gel column chromatography (n-hexane:EtOAc=100:0 to 80:20) to obtain 6-bromo-2,2-dimethyl-1-indanone (158 mg) as a pale yellow oil.

TABLE 23

| Pr | Structure | MS |
|---|---|---|
| 17 | H₃C,H₃C-2,2-dimethyl-6-bromoindan-1-one | 261, 263 |

Preparation Example 18

To a solution of 3-amino-4-hydroxybenzonitrile (730 mg) in DMF (10 ml) was added CDI (1.06 g) at 0° C., followed by stirring at room temperature for 3.5 hours. The reaction solution was diluted with water (10 ml), and extracted with EtOAc (200 ml). The organic layer was dried over anhydrous MgSO₄, and then filtered, and the filtrate was concentrated under reduced pressure. The residue was purified by silica gel column chromatography (chloroform:CH₃OH=98:2 to 93:7) to obtain 2-oxo-2,3-dihydro-1,3-benzoxazole-5-carbonitrile (647 mg) as a pale yellow solid.

The compound shown in Pr 18-1 was prepared in the same manner as in Preparation Example 18.

TABLE 24

| Pr | Structure | MS |
|---|---|---|
| 18 | 5-cyano-benzoxazol-2(3H)-one | 159 |
| 18-1 | 7-cyano-benzoxazol-2(3H)-one | 183 |

Preparation Example 19

To a solution of 60% NaH (12.38 g) in DMF (480 ml) was added a solution of 1H-indole-4-carbonitrile (40.0 g) in DMF (80 ml) at 0° C. After stirring at 0° C. for 30 min, it was stirred at room temperature for 0.5 hour. Thereafter, a solution of 2-bromoacetamide (40.76 g) in DMF (80 ml) was added dropwise thereto at 0° C. The solution was warmed from 0° C. to room temperature, and stirred for 12 hours. To the reaction solution was added water (1200 ml), and the precipitated white solid was collected by filtration. The solution was washed with hot water (300 ml) and diisopropyl ether (200 ml) to obtain 2-(4-cyano-1H-indol-1-yl)acetamide (52.1 g) as a white solid.

TABLE 25

| Pr | Structure | MS |
|---|---|---|
| 19 | 2-(4-cyano-1H-indol-1-yl)acetamide | 222 |

Preparation Example 20

To a solution of 3-chloro-4-(2,2,2-trifluoro-1-methylethoxy)benzonitrile (430 mg) in IPA (3 ml) was added a 5M aqueous NaOH solution (1.37 ml), followed by stirring at 80° C. for 24 hours, and a 5M aqueous NaOH solution (1.37 ml) was further added thereto, followed by stirring at 95° C. for 24 hours. The reaction solution was concentrated until the amount was reduced to a half. To the residue was added 12M HCl, and the resulting precipitate was collected by filtration, and then dried to obtain 3-chloro-4-(2,2,2-trifluoro-1-methylethoxy)benzoic acid as a yellow solid.

The compounds shown in Pr 20-1 through Pr 20-3 were prepared in the same manner as in Preparation Example 20.

TABLE 26

| Pr | Structure | MS |
|---|---|---|
| 20 | 4-(2,2,2-trifluoro-1-methylethoxy)-3-chlorobenzoic acid | 267 |
| 20-1 | 4-(2,2,2-trifluoro-1-methylethoxy)-3-fluorobenzoic acid | 251 |
| 20-2 | 4-(2,2,2-trifluoro-1-methylethoxy)-3-methylbenzoic acid | 247 |
| 20-3 | 4-(2,2,2-trifluoro-1-methylethoxy)-3-methoxybenzoic acid | 263 |

Preparation Example 21

To 3-(difluoromethyl)-4-(2,2,2-trifluoro-1-methylethoxy)benzonitrile (234 mg) were added water (2 ml) and sulfuric acid (2 ml), followed by reflux for 24 hours. After cooling to room temperature, the reaction solution was alkalified with a 5M aqueous NaOH solution, and extracted with diethyl ether (30 ml). The aqueous layer was acidified by 1M HCl, and extracted with EtOAc. The organic layer was dried over anhydrous MgSO$_4$, and then filtered, and the filtrate was concentrated under reduced pressure. The residue was purified by silica gel column chromatography (chloroform:CH$_3$OH=97:3 to 90:10) to obtain 3-formyl-4-(2,2,2-trifluoro-1-methylethoxy)benzoic acid (151 mg) as a white solid.

The compounds shown in Pr 21-1 through Pr 21-8 were prepared in the same manner as in Preparation Example 21.

TABLE 27

| Pr | Structure | MS |
|---|---|---|
| 21 | 3-formyl-4-(2,2,2-trifluoro-1-methylethoxy)benzoic acid | 261 |

TABLE 27-continued

| Pr | Structure | MS |
|---|---|---|
| 21-1 | 4-(1,1-dimethyl-2,2,2-trifluoroethoxy)-3-trifluoromethylbenzoic acid | 315 |
| 21-2 | 4-isobutyl-3-trifluoromethylbenzoic acid | 245 |
| 21-3 | 4-cyclopentyl-3-trifluoromethylbenzoic acid | 257 |
| 21-4 | (R)-4-(2,2,2-trifluoro-1-methylethoxy)-3-trifluoromethylbenzoic acid | 301 |
| 21-5 | 3-formyl-4-(2,2,2-trifluoro-1-methylethoxy)benzoic acid | 261 |
| 21-6 | 3-bromo-4-(2,2,2-trifluoro-1-methylethoxy)benzoic acid | 311, 313 |

Preparation Example 22

To 5-bromo-2-(2,2,2-trifluoro-1-methylethoxy)benzonitrile in a mixed solvent of toluene/THF (4:1) was added a solution of n-BuLi in n-hexane at −78° C. With passing a CO$_2$ gas therethrough, the solution was stirred for 0.5 hour. To the reaction solution was added a 1M aqueous NaOH solution to complete the reaction, and followed by extraction with diethyl ether. The organic layer was acidified by adding 1M HCl, extracted with EtOAc, dried over anhydrous MgSO$_4$, and concentrated. The residue was purified by silica gel chromatography (chloroform:CH$_3$OH=97:3 to 90:10) to obtain 3-cyano-4-(2,2,2-trifluoro-1-methylethoxy)benzoic acid as a white solid.

The compound shown in Pr 22-1 was prepared in the same manner as in Preparation Example 22.

TABLE 28

| Pr | Structure | MS |
|---|---|---|
| 22 | (structure: 3-cyano-4-(1,1,1-trifluoropropan-2-yloxy)benzoic acid) | 258 |
| 22-1 | (structure: 2,2-dimethyl-2,3-dihydro-1H-indene-5-carboxylic acid) | 189 |

Preparation Example 23

To a mixed solution was added a 1M aqueous NaOH solution (4.1 ml) of methyl 1-isobutyl-2-oxo-1,2-dihydropyridine-4-carboxylate (430 mg) in CH₃OH-THF (4 ml-3 ml). The solution was stirred at room temperature for 10 hours, and then concentrated under reduced pressure, and water (10 ml) was added, and subsequently 1M HCl was added thereto until pH becomes 3. The resulting solid was collected by filtration, washed with water, and dried under reduced pressure to obtain 1-isobutyl-2-oxo-1,2-dihydropyridine-4-carboxylic acid (325 mg) as white powders.

TABLE 29

| Pr | Structure | MS |
|---|---|---|
| 23 | (structure: 1-isobutyl-2-oxo-1,2-dihydropyridine-4-carboxylic acid) | 194 |

Preparation Example 24

A solution of 1H-benzimidazole-5-carboxylic acid (75.0 g) in dichloromethane (750 ml) was allowed to be reacted with oxalyl chloride (76.3 g, 52.4 ml) at room temperature for 1 hour, and then the reaction solution was concentrated. To a solution of the residue in THF (750 ml) was added a 28% aqueous NH₃ solution (5 ml) under ice-cooling. This reaction mixture was stirred at the same temperature, and the reaction solution was concentrated. The purple residue was powdered/washed with IPE/IPA, and then collected by filtration to obtain 1H-benzimidazole-6-carboxamide (129 g) (including inorganic salts).

The compound shown in Pr 24-1 was prepared in the same manner as in Preparation Example 24.

TABLE 30

| Pr | Structure | MS |
|---|---|---|
| 24 | (structure: 1H-benzimidazole-5-carboxamide) | 162 |
| 24-1 | (structure: 1H-benzimidazole-7-carboxamide) | 184 |

Preparation Example 25

Preparation Example 25-1

To a solution of 1H-1,2,3-benzotriazole-5-carboxylic acid (2 g), EDCl/HCl (2.82 g), and HOBt in DMF (70 ml) was added an aqueous NH₃ solution (5.1 ml), followed by reaction at room temperature for 2 hours. It was concentrated, and the residue was washed with a saturated NaHCO₃ solution, collected by filtration, and dried to obtain 1H-1,2,3-benzotriazole-5-carboxamide (1.98 g) as a black solid.

Preparation Example 25-3

In a 50 ml reaction vessel, to a solution of methyl 4-chloro-2-methyl-1H-benzimidazole-6-carboxylate ester (300 mg) in formamide (2.65 ml) was added NaOCH₃ (288 mg) at room temperature. The solution was stirred at 80° C. for 3 hours. Completion of the reaction was confirmed by TLC and LC, and then the reaction solution was concentrated, and added with water to complete the reaction. It was extracted with EtOAc. The organic layer was washed with saturated brine, dried over anhydrous MgSO₄, and then filtered, and the filtrate was concentrated. It was purified by silica gel column chromatography (automatic purifier, chloroform: CH₃OH=100:0 to 90:10) to obtain 4-chloro-2-methyl-1H-benzimidazole-6-carboxamide (257 mg) as a white solid.

The compound shown in Pr 25-2 was prepared in the same manner as in Preparation Example 25-1.

TABLE 31

| Pr | Structure | MS |
|---|---|---|
| 25-1 | (structure: 1H-benzotriazole-5-carboxamide) | 185 |
| 25-2 | (structure: 1,3-benzothiazole-6-carboxamide) | 201 |

TABLE 31-continued

| Pr | Structure | MS |
|---|---|---|
| 25-3 | H₂N-C(=O)-benzimidazole-2-CH₃ with Cl | 232, 234 |

Preparation Example 26

To a solution of 3-formyl-4-(2,2,2-trifluoro-1-methylethoxy)benzoic acid (490 mg) and K$_2$CO$_3$ (387 mg) in acetone (10 ml) was added iodomethane (350 μl) at room temperature, followed by stirring for 2 hours. The reaction mixture was diluted with water (15 ml), and extracted with EtOAc (30 ml). The organic layer was dried over anhydrous MgSO$_4$, and filtered to remove the desiccant, and the solvent was concentrated. The residue was purified by silica gel column chromatography (n-hexane:EtOAc=95:5 to 80:20) to obtain methyl 3-formyl-4-(2,2,2-trifluoro-1-methylethoxy)benzoate (122 mg) as a white solid.

TABLE 32

| Pr | Structure | MS |
|---|---|---|
| 26 | F$_3$C-CH(CH$_3$)-O-aryl-CHO with CO$_2$CH$_3$ | 275 |

Preparation Example 27

Under ice-cooling, to DMF (30 ml) was slowly added dropwise POCl$_3$ (6.68 g, 4.06 ml), followed by reaction at room temperature for 2 hours, and then a solution of 1H-benzimidazole-6-carboxamide (2.38 g) in DMF (47.6 ml) was added thereto, followed by stirring at room temperature for 2 hours. To the solution was added a 1M aqueous NaOH solution (pH 6 to 7), followed by stirring at room temperature for 0.5 hour. The solution was extracted with EtOAc, and the organic layer was combined, washed with saturated brine, dried over anhydrous MgSO$_4$, and then filtered, and the filtrate was concentrated. The residue was purified by silica gel chromatography, and powdered/washed with IPE to obtain 1H-benzimidazole-6-carbonitrile (0.58 g) as a pale red crystal.

The compounds shown in Pr 27-1 through Pr 27-2 were prepared in the same manner as in Preparation Example 27.

TABLE 33

| Pr | Structure | MS |
|---|---|---|
| 27 | NC-benzotriazole | 144 |
| 27-1 | NC-benzimidazole-2-CH₃ with Cl | 192 |
| 27-2 | NC-benzimidazole | 144 |

Preparation Example 28

A solution of 1,3-benzothiazole-6-carboxamide (1.96 g) in POCl$_3$ (10 ml) was refluxed for 4 hours. The reaction solution was concentrated, and water was slowly added thereto at 0° C. It was extracted with EtOAc, and the organic layer was dried over anhydrous MgSO$_4$, and then filtered, and the filtrate was concentrated. The residue was purified by silica gel column chromatography (n-hexane:EtOAc=80:20 to 60:40) to obtain 1,3-benzothiazole-6-carbonitrile as a pale yellow solid.

The following Pr 28-1 was prepared in the same manner as in Preparation Example 28.

TABLE 34

| Pr | Structure | MS |
|---|---|---|
| 28 | NC-benzothiazole | 183 |
| 28-1 | NC-benzotriazole | 143 |

Preparation Example 29

To a solution of 6-bromo[1,2,4]triazolo[1,5-a]pyridine (400 mg) in DMF were added tris(dibenzylideneacetone)dipalladium (0), 1'-bis(diphenylphosphino)ferrocene, and Zn(CN)$_2$ under a nitrogen atmosphere, followed by stirring at 110° C. for 23 hours. It was cooled to room temperature, and saturated NH$_4$Cl (12 ml), a saturated NH$_3$ solution (6 ml), and H$_2$O (12 ml) were added thereto. The reaction mixture was extracted three times with EtOAc. The organic layer was washed with saturated brine, dried over anhydrous MgSO$_4$, and then filtered, and the filtrate was concentrated. The residue was purified by silica gel column chromatography (0 to 5% CH$_3$OH/chloroform)[1,2,4]triazolo[1,5-a]pyridine-6-carbonitrile as a dark red solid.

Preparation Example 30

In a 100 ml reaction vessel, to a solution of 6-bromo-7-methyl-1H-benzimidazole (500 mg) in DMF were added Zn(CN)$_2$ (834 mg) and Pd (PPh)$_4$ (547 mg) at room temperature, followed by stirring at 150° C. for 5 hours. The reaction solution was poured into a 1:1 mixed solvent of a saturated NaHCO$_3$ solution and EtOAc, followed by stirring for 1 hour. The organic layer was washed with saturated brine, dried over anhydrous MgSO$_4$, and then filtered, and the filtrate was concentrated. It was purified by silica gel column chromatography (automatic purifier, chloroform:CH$_3$OH=98:2 to 90:10) to obtain 7-methyl-1H-benzimidazole-6-carbonitrile (161.8 mg) as a brown solid.

The following Pr 30-1 through Pr 30-7 were prepared in the same manner as in Preparation Example 30. They were also prepared by the method as in Preparation Example 29.

TABLE 35

| Pr | Structure | Data |
|---|---|---|
| 29 | 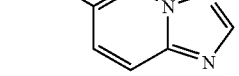 | NMR: 7.98 (1H, d), 8.04 (1H, d), 8.74 (1H, s), 9.90-9.87(1H, m) |
| 30 | 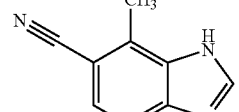 | MS: 158 |
| 30-1 | 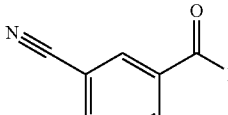 | NMR: 7.67 (1H, dd), 8.25 (1H, ddd), 8.34(1H, dd), 10.17(1H, s) |
| 30-2 | 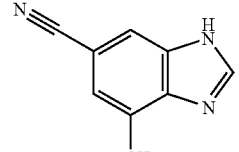 | MS: 158 |
| 30-3 | 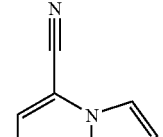 | MS: 144 |
| 30-4 | 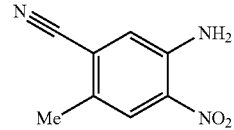 | MS: 176 |

TABLE 35-continued

| Pr | Structure | Data |
|---|---|---|
| 30-5 | 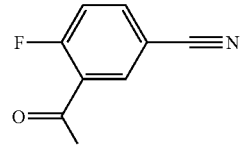 | NMR: 10.17 (1H, s), 8.34 (1H, dd), 8.25 (1H, ddd), 7.67(1H, dd) |
| 30-6 | 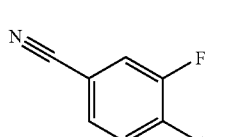 | NMR: 7.95(1H, dd), 8.19 (1H, dd), 8.23(1H, dd) |
| 30-7 | 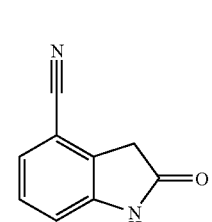 | MS: 157 |

Preparation Example 31

To a mixed solution of 4-hydroxy-3-nitrobenzonitrile (1 g) and NH$_4$Cl (163 mg) in ethanol (20 ml), THF (10 ml), and water (10 ml) were added Celite (5 g) and reduced iron (1.7 g), followed by heating under reflux at 70° C. for 30 min. The reaction solution was cooled to room temperature, diluted with EtOAc (200 ml), and then filtered through celite. The solution was washed with saturated brine, the organic layer was dried over anhydrous MgSO$_4$, and filtered, and the filtrate was concentrated under reduced pressure to obtain 3-amino-4-hydroxybenzonitrile (740 mg) as a pale brown solid.

The following Pr 31-1 through Pr 31-3 were prepared in the same manner as in Preparation Example 31.

TABLE 36

| Pr | Structure | MS |
|---|---|---|
| 31 | 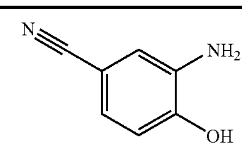 | 133 |
| 31-1 | 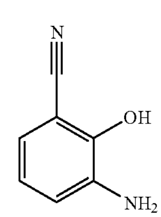 | 157 |

TABLE 36-continued

| Pr | Structure | MS |
|----|-----------|-----|
| 31-2 | 3-bromo-2-methyl-benzene-1,2-diamine (Br, CH₃, NH₂, NH₂) | 225, 227 |
| 31-3 | 4-amino-5-methyl-benzonitrile with NH₂ groups (N≡C, NH₂, H₃C, NH₂) | 170 |

Preparation Example 32

To a mixed solution of 4-amino-3-nitrobenzonitrile (8 g) in EtOH/THF (40 ml/40 ml) was added Pd—C(50% wet) (0.8 g), followed by stirring under an $H_2$ atmosphere for 12 hours. The reaction solution was filtered through celite, and concentrated. The residue was powdered/washed with a mixed solvent of IPE and IPA, and collected by filtration to obtain 3,4-diaminobenzonitrile (6.3 g) as orange powders.

TABLE 37

| Pr | Structure | MS |
|----|-----------|-----|
| 32 | 3,4-diaminobenzonitrile (N≡C, NH₂, NH₂) | 156 |

Preparation Example 33

To a solution of 2-amino-3-nitrobenzonitrile (2 g) in THF (30 ml) were added 4-pentenoyl chloride (2.90 g) and diisopropylethylamine (4.27 ml), followed by stirring at 80° C. for 12 hours. The reaction solution was poured into water, and extracted with EtOAc. The organic layer was dried over anhydrous $MgSO_4$, and then filtered, and the filtrate was concentrated under reduced pressure. The residue was purified by silica gel column chromatography (chloroform:$CH_3OH$) to obtain N-(4-cyano-2-nitrophenyl)pent-4-enamide (174 mg) as a colorless liquid.

The following Pr 33-1 through Pr 33-2 were prepared in the same manner as in Preparation Example 33.

TABLE 38

| Pr | Structure | MS |
|----|-----------|-----|
| 33 | N-(4-cyano-2-nitrophenyl)pent-4-enamide | 244 |

TABLE 38-continued

| Pr | Structure | MS |
|----|-----------|-----|
| 33-1 | 4-cyano-2-nitrophenyl with NH-C(O)-CH₂CH₂-C(O)-OEt | 290 |
| 33-2 | 4-cyano-2-nitrophenyl with NH-C(O)-CH₂CH₂-SMe | 264 |

Preparation Example 34

To a solution of 3-chloro-4-fluorobenzonitrile (300 mg) and 1,1,1-trifluoro-2-propanol (263 mg) in THF (15 ml) was added 60% NaH (92.5 mg) at 5° C., followed by stirring at room temperature for 2 hours, addition of a saturated $NH_4Cl$ solution to complete the reaction, and extraction with EtOAc. The obtained organic layer was dried over anhydrous $MgSO_4$, and concentrated. The residue was purified by silica gel chromatography (n-hexane:EtOAc=97:3 to 85:15) to obtain 3-chloro-4-(2,2,2-trifluoro-1-methylethoxy)benzonitrile (435 mg) as a colorless oily substance.

The following Pr 34-1 through Pr 34-6 were prepared in the same manner as in Preparation Example 34.

TABLE 39

| Pr | Structure | Data |
|----|-----------|------|
| 34 | 3-chloro-4-(2,2,2-trifluoro-1-methylethoxy)benzonitrile (F₃C, CH₃, O, Cl, C≡N) | NMR below |
| 34-1 | 3-fluoro-4-(2,2,2-trifluoro-1-methylethoxy)benzonitrile (F₃C, CH₃, O, F, C≡N) | NMR below |
| 34-2 | 3-methyl-4-(2,2,2-trifluoro-1-methylethoxy)benzonitrile (F₃C, CH₃, O, H₃C, C≡N) | MS: 252 |

TABLE 39-continued

| Pr | Structure | Data |
|---|---|---|
| 34-3 | 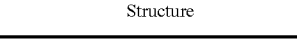 | MS: 268 |
| 34-4 | 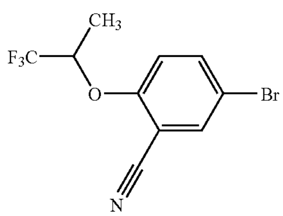 | NMR below |
| 34-5 | 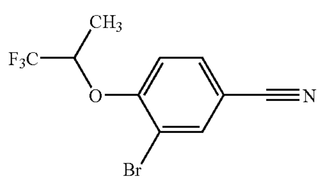 | MS: 316, 318 |

TABLE 40

| Pr | NMR |
|---|---|
| 34 | 1.48(3H, d), 5.53(1H, m), 7.57(1H, d), 7.87(1H, dd), 8.09(1H, d) |
| 34-1 | 1.47(3H, d), 5.50(1H, m), 7.59(1H, t), 7.74(1H, dm), 7.95(1H, dd) |
| 34-4 | 1.47(3H, d), 5.48(1H, m), 7.46(1H, d), 7.90(1H, dd), 8.08(1H, d) |

Preparation Example 35

In a 50 ml reaction vessel, to a solution of 4-{5-[3-(trifluoromethyl)-4-(2,2,2-trifluoro-1-methylethoxy)phenyl]-1,2,4-oxadiazol-3-yl}-1H-indole (100 mg) in DMF (1 ml) was added 60% NaH (10.9 mg) at 0° C. The solution was warmed to room temperature, followed by stirring for 0.5 hour. Further, tertiary-butyl (2-iodoethoxy)dimethylsilane was added thereto at 0° C., followed by stirring at room temperature for 15 hours. Completion of the reaction was confirmed by LC-MS, and then the reaction solution was added with water (30 ml). It was extracted three times with EtOAc (20 ml). The organic layer was washed with saturated brine, dried over anhydrous MgSO$_4$, and concentrated under reduced pressure. It was purified by silica gel column chromatography (automatic purifier, n-hexane:EtOAc=100:0 to 90:10) to obtain 1-(2-{[tertiary-butyl(dimethyl)silyl]oxy}ethyl)-4-{5-[3-(trifluoromethyl)-4-2,2,2-trifluoro-1-methylethoxy)phenyl]-1,2,4-oxadiazol-3-yl}-1H-indole (86.4 mg) as a white solid.

TABLE 41

| Pr | Structure | MS |
|---|---|---|
| 35 | 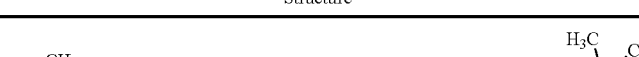 | 622 |

TABLE 39-continued

| Pr | Structure | Data |
|---|---|---|
| 34-6 | 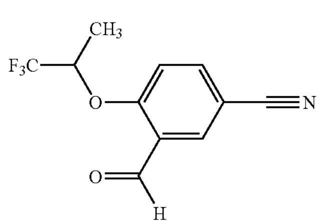 | MS: 242 |

Preparation Example 36

LiH (78 mg) was suspended in DMF (5 ml), and a suspension of methyl-2-oxo-1,2-dihydropyridine-4-carboxylate (500 mg) in DMF (5 ml) was added dropwise thereto at room temperature. The suspension was stirred as it was, and a solution of 1-iodo-2-methylpropane (506 μl) in DMF (5 ml) was added dropwise thereto over 10 min, followed by stirring at 50° C. for 15 hours. To the reaction solution was added 1M HCl at 0° C., followed by extraction with EtOAc, and the organic layer was washed with saturated brine, dried over anhydrous MgSO$_4$, and filtered, and the solvent was evaporated under reduced pressure. The residue was purified by silica gel chromatography (n-hexane:EtOAc=90:10 to 50:50) to obtain methyl-1-isobutyl-2-oxo-1,2-dihydropyridine-4-carboxylate (440 mg) as white powders.

TABLE 42

| Pr | Structure | MS |
|---|---|---|
| 36 | [Structure: 1-isobutyl-2-oxo-1,2-dihydropyridine-4-carboxylic acid methyl ester] | 210 |

Preparation Example 37

To a solution of 4-fluoro-3-nitrobenzonitrile (300 mg) and dimethyl malonate (286 mg) in DMF was added 60% NaH at 0° C., followed by reaction at room temperature to obtain dimethyl (4-cyano-2-nitrophenyl)malonate (198 mg).

TABLE 43

| Pr | Structure | MS |
|---|---|---|
| 37 | [Structure: dimethyl (4-cyano-2-nitrophenyl)malonate] | 301 |

Preparation Example 38

To a solution of dimethyl (4-cyano-2-nitrophenyl) malonate (198 mg) in DMSO (5 ml) were added LiCl (60.3 mg) and H$_2$O (12 μl), followed by stirring at 100° C. for 3 hours. The reaction solution was cooled to room temperature, and poured into EtOAc and saturated brine for partition. The organic layer was washed with saturated brine, dried over anhydrous MgSO$_4$, and then filtered, and the filtrate was concentrated. The residue was purified by silica gel column chromatography (n-hexane:EtOAc=90:10 to 75:25) to obtain methyl (4-cyano-2-nitrophenyl)acetate (128 mg) as a yellow oil.

TABLE 44

| Pr | Structure | MS |
|---|---|---|
| 38 | [Structure: methyl (4-cyano-2-nitrophenyl)acetate] | 219 |

Preparation Example 39

To a solution of 4-chloro-3-(trifluoromethyl)benzonitrile (1 g) and iron(3+) tris[(2Z)-4-oxopent-2-ene-2-oleate] (86 mg), and 1-methylpyrrolidin-2-one (2.8 ml) in THF (30 ml) was added a solution of 2M bromo(isobutyl)magnesium in diethyl ether (2.9 ml) under ice-cooling. The solution was stirred at room temperature for 30 minutes, and diluted with diethyl ether (30 ml), and then 1M HCl was carefully added thereto to complete the reaction. The reaction solution was extracted with EtOAc (100 ml), and the organic layer was dried over anhydrous MgSO$_4$, and then filtered, and the filtrate was concentrated under reduced pressure. The residue was purified by silica gel column chromatography (n-hexane: EtOAc=100:0 to 95:5) to obtain 4-isobutyl-3-(trifluoromethyl)benzonitrile (320 mg) as a pale yellow liquid.

The following Pr 39-1 was prepared in the same manner as in Preparation Example 39.

TABLE 45

| Pr | Structure | Data |
|---|---|---|
| 39 | [Structure: 4-isobutyl-3-(trifluoromethyl)benzonitrile] | NMR: 0.89 (6H, d), 1.91-2.03 (1H, m), 2.70 (2H, dm), 7.70 (1H, d), 8.09 (1H, dd), 8.21 (1H, d) |
| 39-1 | [Structure: 4-cyclopentyl-3-(trifluoromethyl)benzonitrile] | MS: 262 |

Preparation Example 40

To a solution of 4-fluoro-3-formylbenzonitrile (300 mg) in dichloromethane (7 ml) was added 2-methoxy-N-(2-methoxyethyl)-N-(trifluoro-X$^4$-sulfanyl)ethanamine (757 mg) at room temperature, followed by stirring for 6 hours, and addition of a saturated aqueous NaHCO$_3$ solution (15 ml). After extraction with chloroform (30 ml), the organic layer was dried over anhydrous MgSO$_4$, filtered, and concentrated. The residue was purified by silica gel column chromatography (n-hexane:EtOAc=95:5 to 80:20) to obtain 3-(difluoromethyl)-4-fluorobenzonitrile (174 mg) as a colorless liquid.

The following Pr 40-1 was prepared in the same manner as in Preparation Example 40.

TABLE 46

| Pr | Structure | Data |
|---|---|---|
| 40 | [Structure: 3-(difluoromethyl)-4-fluorobenzonitrile] | NMR: 7.25 (1H, t), 7.66 (1H, dd), 8.14-8.20 (1H, m), 8.22 (1H, dm) |
| 40-1 | [Structure: methyl 3-(difluoromethyl)-4-(1,1,1-trifluoropropan-2-yloxy)benzoate] | MS: 321 |

Preparation Example 41

The following Pr 41-1 through Pr 41-10 were prepared in the same manner as in Example 2.

TABLE 47

| Pr | Structure | MS |
|---|---|---|
| 41-1 | 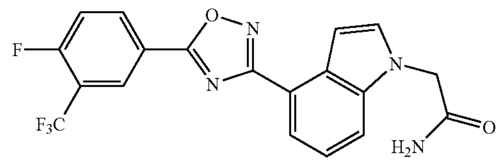 | 427 |
| 41-2 | 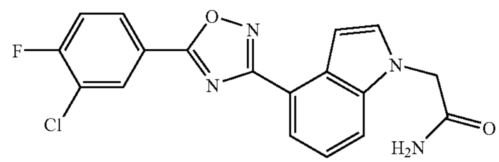 | 393 |
| 41-3 | 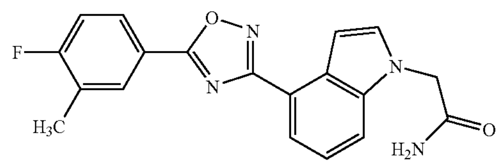 | 373 |
| 41-4 | 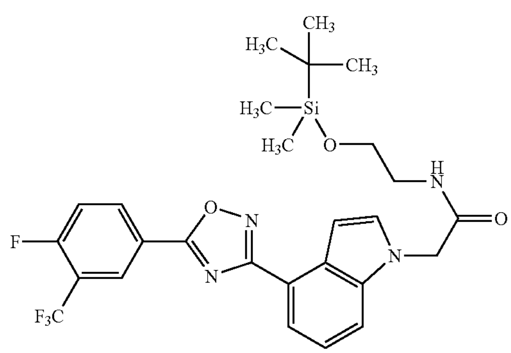 | 585 |
| 41-5 | 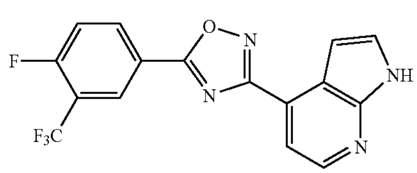 | 349 |
| 41-6 | 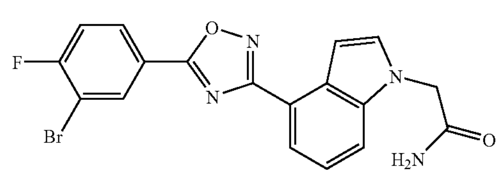 | 437 |
| 41-7 | 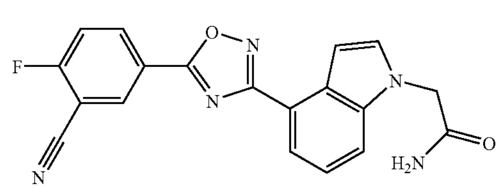 | 362 |

TABLE 47-continued

| Pr | Structure | MS |
|---|---|---|
| 41-8 | (3-chloro-4-fluorophenyl)-oxadiazole-indole-N-CH2-C(O)-NH-CH2CH2-O-Si(CH3)2-C(CH3)3 | 551 |
| 41-9 | (4-fluoro-3-trifluoromethylphenyl)-oxadiazole-indole-N-CH2-C(O)-NH2 | 405 |
| 41-10 | (5,6-dichloropyridin-3-yl)-oxadiazole-indole-N-CH2-C(O)-NH2 | 410 |

Preparation Example 42

The following Pr 42-1 through Pr 42-3 were prepared in the same manner as in Example 5.

TABLE 48

| Pr | Structure | Data |
|---|---|---|
| 42-1 | (CH3)2C(CF3)-O-C6H3(CF3)-CN | NMR: 1.67 (6H, s), 7.71 (1H, d), 8.12 (1H, dd), 8.26 (1H, d) |
| 42-2 | CH3-CH(CF3)-O-C6H3(CF3)-CN | MS: 282 |
| 42-3 | CH3-CH(CF3)-O-C6H3(CHF2)-CN | NMR: 1.67 (6H, s), 7.71 (1H, d), 8.12 (1H, dd), 8.26 (1H, d) MS: 288 |

Preparation Example 43

The following Pr 43 was prepared in the same manner as in Example 6.

TABLE 49

| Pr | Structure | MS |
|---|---|---|
| 43 | (1,3-difluoropropan-2-yloxy)-(3-chloro)phenyl-oxadiazole-indole-N-CH2-C(O)-NH-CH2CH2-O-Si(CH3)2-C(CH3)3 | 627 |

Preparation Example 44

The following Pr 44-1 and Pr 44-2 were prepared in the same manner as in Example 12.

TABLE 50

| Pr | Structure | MS |
|---|---|---|
| 44-1 | (chiral structure with F₃C-CH(CH₃)-O-phenyl(CF₃)-oxadiazole-indole-N-CH₂-C(O)-O-CH₃) Chiral | 536 |
| 44-2 | (4-cyanoindole with N-CH₂-C(O)-NH₂) | 222 |

Preparation Example 45

The following Pr 45 was prepared in the same manner as in Preparation Example 47.

TABLE 51

| Pr | Structure | NMR |
|---|---|---|
| 45 | (F₃C-CH(CH₃)-O-phenyl(CHF₂)-C(O)OH) | 1.47 (3H, d), 5.49-5.60 (1H, m), 7.09 (1H, t), 7.50 (1H, d), 8.07-8.13 (2H, m) |

Preparation Example 46

The following Pr 46-1 through Pr 46-5 were prepared in the same manner as in Example 19.

TABLE 52

| Ex | Structure | MS |
|---|---|---|
| 46-1 | (F₃C-CH(CH₃)-O-phenyl(CH₃)-oxadiazole-indole-N-CH₂-C(O)-NH-CH₂CH₂-O-Si(CH₃)₂-C(CH₃)₃) Chiral | 625 |
| 46-2 | (FCH₂-CH(CH₂F)-O-phenyl(CF₃)-oxadiazole-indole-N-CH₂-C(O)-NH-CH₂CH₂-O-Si(CH₃)₂-C(CH₃)₃) Chiral | 661 |

TABLE 52-continued

| Ex | Structure | MS |
|---|---|---|
| 46-3 | [Chiral structure: 2-(trifluoromethyl)-1-methylethoxy-phenyl-oxadiazole-indole-acetamide-ethoxy-tert-butyldimethylsilyl] | 657 |
| 46-4 | [Chiral structure: 2-(trifluoromethyl)-1-methylethoxy-phenyl-oxadiazole-indole-acetamide-serine ethyl ester with TBDMS protection] | 751 |
| 46-5 | [4-cyanoindole-N-acetamide-ethoxy-tert-butyldimethylsilyl] | 380 |

Preparation Example 47

To a solution of ethyl (7-{5-[3-(trifluoromethyl)-4-(2,2,2-trifluoro-1-methylethoxy)phenyl]-1,2,4-oxadiazol-3-yl}imidazo[1,2-a]pyridin-2-yl)acetate (230 mg) in THF (2.0 ml) was added a 1M aqueous NaOH solution (1.0 ml), followed by stirring at 80° C. for 2 hours. After cooling to room temperature, a 1 M HCl aqueous solution (1.0 ml) was added thereto, followed by extraction with chloroform. The organic layer was dried over anhydrous MgSO₄, and then filtered, and the filtrate was concentrated. The residue was purified by silica gel column chromatography (chloroform:CH₃OH=10:1 to 5:1) to obtain colorless powders. To a solution of this colorless powder in EtOAc was added a 4M HCl/EtOAc solution, followed by concentration. The resulting colorless powder was powdered/washed with IPE to obtain (7-{5-[3-(trifluoromethyl)-4-(2,2,2-trifluoro-1-methylethoxy)phenyl]-1,2,4-oxadiazol-3-yl}imidazo[1,2-a]pyridin-2-yl)acetic acid hydrochloride (180.4 mg) as colorless powders.

The following Pr 47-1 through Pr 47-13 were prepared in the same manner as in Preparation Example 47.

TABLE 53

| Pr | Structure |
|---|---|
| 47 | [trifluoromethyl-methylethoxy-phenyl-oxadiazole-imidazopyridine-acetic acid · HCl] |
| 47-1 | [trifluoromethyl-methylethoxy-phenyl-oxadiazole-benzimidazole-propionic acid] |
| 47-2 | [trifluoromethyl-methylethoxy-phenyl-oxadiazole-imidazopyridine-acetic acid · HCl] |
| 47-3 | [trifluoromethyl-methylethoxy-phenyl-oxadiazole-benzimidazole-N-acetic acid] |

TABLE 53-continued

| Pr | Structure |
|---|---|
| 47-4 | (structure) |
| 47-5 | (structure) |
| 47-6 | (structure) |
| 47-7 | (structure) |
| 47-8 | (structure) |
| 47-9 | (structure, Chiral) |
| 47-10 | (structure) |
| 47-11 | (structure) |
| 47-12 | (structure, Chiral) |
| 47-13 | (structure, Chiral) |

TABLE 54

| Pr | MS | Pr | MS | Pr | MS | Pr | MS |
|---|---|---|---|---|---|---|---|
| 47 | 501 | 47-1 | 515 | 47-2 | 501 | 47-3 | 499 |
| 47-4 | 522 | 47-5 | 514 | 47-6 | 499 | 47-7 | 530 |
| 47-8 | 500 | 47-9 | 468 | 47-10 | 504 | 47-11 | 555 |
| 47-12 | 498 | 47-13 | 585 | | | | |

Example 1

A solution of 3-(trifluoromethyl)-4-(2,2,2-trifluoro-1-methylethoxy)benzoic acid (810 mg), EDCl/HCl (616 mg), and N'-hydroxy-7-methylimidazo[1,2-a]pyridine-6-carboxamide (510 mg) in dioxane was stirred at 115° C. for 60 hours. The reaction solution was concentrated, and the residue was partitioned between water and chloroform. The organic layer was dried over anhydrous $MgSO_4$, and then filtered, and the filtrate was concentrated. The residue was purified by silica gel column chromatography ($CH_3OH$/chloroform=0 to 5%), and recrystallized with EtOH to obtain 7-methyl-6-{5-[3-(trifluoromethyl)-4-(2,2,2-trifluoro-1-methylethoxy)phenyl]-1,2,4-oxadiazol-3-yl}imidazo[1,2-a]pyridine (60 mg) as a white solid.

Example 2

To a solution of 3-(trifluoromethyl)-4-(2,2,2-trifluoro-1-methylethoxy)benzoic acid (349 mg) in dichloromethane (6 ml) were added oxalyl chloride (333 mg) and a catalytic amount of DMF under ice-cooling, followed by stirring at room temperature for 1 hour. The reaction solution was concentrated, and azeotroped with toluene. To a solution of the residue in THF were added N'-hydroxy-2-methyl-1H-benzimidazole-6-carboxyimidamide (200 mg) and N-ethyl-N-isopropyl-2-propaneamine (543 mg). The reaction mixture was stirred at room temperature for 2 hours. To the reaction solution was added water, followed by three times extractions with EtOAc. The organic layer was combined, dried over anhydrous $MgSO_4$, and then filtered, and the filtrate was concentrated. The residue was dissolved in dioxane, followed by stirring at 100° C. for 3 hours. After cooling to room temperature, it was concentrated under reduced pressure to remove the solvent, and purified by silica gel column chromatography to obtain a colorless oily substance. To a solution of this oily substance in EtOAc was added a 4M HCl/EtOAc solution, followed by stirring for a few minutes, and then the reaction mixture was concentrated to obtain 2-methyl-5-{5-[3-(trifluoromethyl)-4-(2,2,2-trifluoro-1-methylethoxy)phenyl]-1,2,4-oxadiazol-3-yl}-1H-benzimidazole hydrochloride (239 mg) as a colorless crystal.

Example 3

To a solution of 4-(2,2,2-trifluoro-1,1-dimethylethoxy)-3-(trifluoromethyl)benzoic acid (118 mg) and 2-{4-[amino(hydroxyimino)methyl]-1H-indol-1-yl}acetamide (104 mg) in dioxane (5 ml) was added DIC (69 µl), followed by stirring at room temperature for 3 hours, and then heating under reflux for 20 hours. The reaction solution was concentrated, and then to the residue was added water (15 ml), followed by extraction with chloroform (15 ml). The organic layer was washed with a saturated aqueous $NaHCO_3$ solution and saturated brine, dried over anhydrous $MgSO_4$, filtered, and the filtrate was concentrated under reduced pressure. The residue was purified by preparative HPLC (column: CAPCEL PAK, C18, MG, S-5, 30×50 mm; solvent: 50-90% acetonitrile/10 mM ammonium carbonate-ammonia (pH 9.2); 40 ml/min), and crystallized with diisopropyl ether to obtain 2-(4{5-[4-(2,2,2-trifluoro-1,1-dimethylethoxy)-3-(trifluoromethyl)phenyl]-1,2,4-oxadiazol-3-yl}-1H-indol-1-yl)acetamide (40 mg) as a white solid.

Example 4

To a suspension of 60% NaH (68.0 mg) in DMF was added cyclopropylmethanol (99 mg) at 0° C., followed by stirring at the same temperature for 15 min, and then 5-{5-[4-fluoro-3-(trifluoromethyl)phenyl]-1,2,4-oxadiazol-3-yl}-1H-benzimidazole (120 mg) was added thereto. The reaction mixture was stirred at room temperature for 2 hours, and then added with water. It was extracted with EtOAc, and the organic layer was concentrated. The residue was purified by silica gel column chromatography ($CH_3OH$/chloroform=0 to 5%) to obtain an oily substance. A solution of the oily substance in chloroform-$CH_3OH$ was added with a 4M HCl/dioxane solution (0.5 ml), and concentrated to obtain 5-{5-[4-(cyclopropylmethoxy)-3-(trifluoromethyl)phenyl]-1,2,4-oxadiazol-3-yl}-1H-benzimidazole hydrochloride (20 mg) as a white solid.

HPLC analysis: Condition (TSK-GEL (TOSOH) ODS-80TM 4.6×150 mm, MeCN: 0.01M $KH_2PO_4$ (7:3), 1.0 ml/min, 254 nm)[RT: 7.90 min]

Example 5

To a solution of 2-(4-{5-[4-fluoro-3-(trifluoromethyl)phenyl]-1,2,4-oxadiazol-3-yl}-1H-indol-1-yl)acetamide (100 mg) and 2-propanol (35 µl) in DMF (3 ml) was added 60% NaH (12 mg) at 0° C., followed by stirring at room temperature for 9 hours. The reaction solution was added with water (5 ml) to complete the reaction, and extracted with as a mixed solvent of chloroform:$CH_3OH$ (8:2). The organic layer was washed with saturated brine, dried over anhydrous $MgSO_4$, and then filtered, and the filtrate was concentrated under reduced pressure. The residue was purified by silica gel column chromatography (chloroform:$CH_3OH$=98:2 to 93:7), and crystallized with diethyl ether to obtain 2-(4-{5-[4-isopropoxy-3-(trifluoromethyl)phenyl]-1,2,4-oxadiazol-3-yl}-1H-indol-1-yl)acetamide (25 mg) as a pale yellow solid.

Example 6

To a solution of 1,3-difluoropropanol (62 mg) in DMF (2.4 ml) was added 60% NaH (19 mg) at −10° C., followed by stirring at −10° C. for 0.5 hour. To this reaction mixture was added 2-{4-[5-(3-chloro-4-fluorophenyl)-1,2,4-oxadiazol-3-yl]-1H-indol-1-yl}acetamide (120 mg) at −10° C., followed by stirring at −10° C. for 3 hours. After adding water to the reaction solution, the reaction mixture was extracted with EtOAc, the organic layer was washed with saturated brine, dried over anhydrous $MgSO_4$, and then filtered, and the filtrate was concentrated under reduced pressure. The residue was purified by silica gel column chromatography (chloroform:$CH_3OH$=100:0 to 95:5) to obtain 2-[4-(5-{3-chloro-4-[2-fluoro-1-(fluoromethyl)ethoxy]phenyl}-1,2,4-oxadiazol-3-yl)-1H-indol-1-yl]acetamide (76.9 mg) as a white solid.

Example 7

To a solution of 2-{4-[5-(4-fluoro-3-methylphenyl)-1,2,4-oxadiazol-3-yl]-1H-indol-1-yl}acetamide (100 mg) and (2R)-1,1,1-trifluoropropane-2-ol (109 mg) in DMF (3 ml) was added 60% NaH (17 mg) at 0° C., followed by stirring at 80° C. for 4 hours. The reaction solution was added with water (15 ml) to complete the reaction, filtered, and then dried. The obtained powder was purified by silica gel column chromatography (chloroform:$CH_3OH$=100:0 to 95:5), and crystallized with diisopropyl ether to obtain 2-[4-(5-{3-methyl-4-[(1R)-2,2,2-trifluoro-1-methylethoxy]phenyl}-1,2,4-oxadiazol-3-yl)-1H-indol-1-yl]acetamide (70 mg) as a pale yellow solid.

Example 8

To a suspension of 60% NaH (43 mg) in DMF (4 ml) was added 2-propanol (65 mg) at 0° C., followed by stirring at room temperature for 20 min. After cooling to 0° C. again, 2-{4-[5-(3-chloro-4-fluorophenyl)-1,2,4-oxadiazol-3-yl]-1H-indol-1-yl-acetamide (200 mg) was added thereto. The reaction mixture was radiated with a microwave at 60° C. for 50 min. The reaction solution was added to an aqueous $NH_4Cl$ solution, followed by stirring, and then the solvent was evaporated. After adding a mixed solvent (4:1) of chloroform-$CH_3OH$, and suspending, the solid was removed, silica gel was added thereto, and the solvent was evaporated. The residue was purified by silica gel column chromatography (chloroform:$CH_3OH$=100:0 to 98:2; n-hexane:EtOAc=0:100) to obtain 2-{4-[5-(3-chloro-4-isopropylphenyl)-1,2,4-oxadiazol-3-yl]-1H-indol-1-yl}acetamide (17.5 mg) as a white solid.

Example 9

To a solution of 4-{5-[4-fluoro-3-(trifluoromethyl)phenyl]-1,2,4-oxadiazol-3-yl}-1H-indole (300 mg) in THF (1.5 ml) was added, propane-2-amine (0.75 ml), and after sealing the tube, the solution was stirred at 50 to 55° C. for 40 hours.

It was concentrated under reduced pressure, and then purified by silica gel chromatography (n-hexane:EtOAc). The obtained solid was dissolved in acetone under heating, and added with n-hexane, and the precipitate was filtered to obtain 4-[3-(1H-indol-4-yl)-1,2,4-oxadiazol-5-yl]-N-isopropyl-2-(trifluoromethyl)aniline (295 mg).

Example 10

To a mixed solution of 2-{4-[5-(5,6-dichloropyridin-3-yl)-1,2,4-oxadiazol-3-yl]-1H-indol-1-yl}acetamide (100 mg) in dioxane (2 ml) and NMP (2 ml) was added isopropylamine (2200, followed by stirring at 150° C. for 1 hour in a microwave reaction vessel. The reaction mixture was concentrated under reduced pressure, and then the residue was purified by silica gel chromatography (n-hexane:EtOAc=40:60 to 0:100), and the obtained residue was suspended in diisopropyl ether under heating, and collected by filtration to obtain 2-(4-{5-[5-chloro-6-(isopropylamino)pyridin-3-yl]-1,2,4-oxadiazol-3-yl}-1H-indol-1-yl)acetamide (62 mg) as white powders.

Example 11 (11-1 and 11-2)

To a solution of 5-{5-[3-(trifluoromethyl)-4-(2,2,2-trifluoro-1-methylethoxy)phenyl]-1,2,4-oxadiazol-3-yl}-1H-benzimidazole (105 mg) in DMF (3.15 ml) was added 60% NaH (31 mg) under ice-cooling, followed by stirring at the same temperature for 15 min, and methyl iodide (0.22 ml) was added thereto, followed by stirring at room temperature for 5 hours. To the reaction was added water, followed by extraction with EtOAc, the organic layer was washed with saturated brine, dried over anhydrous $MgSO_4$, and then filtered, and the filtrate was concentrated. The residue was purified by silica gel column chromatography (automatic producer, chloroform:$CH_3OH$=10:1). The objective substance was dissolved in EtOAc (5 ml), added with a 4M HCl/EtOAc solution (5 ml), and concentrated to produce about 1:1 two regioisomers. The mixture was crystallized with acetonitrile to obtain 1-methyl-5-{5-[3-(trifluoromethyl)-4-(2,2,2-trifluoro-1-methylethoxy)phenyl]-1,2,4-oxadiazol-3-yl}-1H-benzimidazole hydrochloride (12.1 mg). The mother liquor was concentrated to obtain 1-methyl-5-{5-[3-(trifluoromethyl)-4-(2,2,2-trifluoro-1-methylethoxy)phenyl]-1,2,4-oxadiazol-3-yl}-1H-benzimidazole hydrochloride and 1-methyl-6-{5-[3-(trifluoromethyl)-4-(2,2,2-trifluoro-1-methylethoxy)phenyl]-1,2,4-oxadiazol-3-yl}-1H-benzimidazole hydrochloride (70.2 mg) as colorless powders.

Example 12

To a solution 4-(5-{3-(trifluoromethyl)-4-[(1S)-2,2,2-trifluoro-1-methylethoxy]phenyl}-1,2,4-oxadiazol-3-yl)-1H-indole (150 mg) in DMF (1.5 ml) was added 60% NaH (16 mg) at 0° C., followed by stirring at room temperature for 0.5 hour. Then, to the reaction mixture was added 2-bromoacetamide (70 mg) again at 0° C., followed by stirring at room temperature for 3 hours. To the reaction was added with water, followed by extraction with EtOAc, the organic layer was washed with saturated brine, dried over anhydrous $MgSO_4$, and then filtered, and the filtrate was concentrated under reduced pressure. The residue was purified by silica gel column chromatography (chloroform:$CH_3OH$=100:0 to 90:10) to obtain 2-[4-(5-{3-(trifluoromethyl)-4-[(1S)-2,2,2-trifluoro-1-methylethoxy]phenyl}-oxadiazol-3-yl)-1H-indol-1-yl]acetamide (145 mg) as a white solid.

Example 13

To a solution of 4-{5-[3-(trifluoromethyl)-4-(2,2,2-trifluoro-1-methylethoxy)phenyl]-1,2,4-oxadiazol-3-yl)indoline (100 mg) in acetonitrile (2.5 ml) was added $K_2CO_3$ (46 mg) and 3-iodopropanamide (124 mg) at room temperature, followed by stirring at 80° C. for 15 hours. To the reaction solution was added an $NaHCO_3$ aqueous saturated solution, followed by extraction with EtOAc. The organic layer was washed with saturated brine, dried over anhydrous $MgSO_4$, and then filtered, and the filtrate was concentrated under reduced pressure. The residue was purified by silica gel column chromatography (chloroform:$CH_3OH$=100:0 to 90:10) to obtain 3-(4-{5-[3-(trifluoromethyl)-4-(2,2,2-trifluoro-1-methylethoxy)phenyl]-1,2,4-oxadiazol-3-yl}-2,3-dihydro-1H-indol-1-yl)propanamide (23.6 mg) as a white solid.

Example 14

To a solution of 4-{5-[3-(trifluoromethyl)-4-(2,2,2-trifluoro-1-methylethoxy)phenyl]-1,2,4-oxadiazol-3-yl}-1H-indole-3-carboaldehyde (150.0 mg) in $CH_3OH$ (1.5 ml) was added a 40% $CH_3OH$ solution of $CH_3NH_2$ (74.5 mg) at 0° C. After warming to room temperature, the solution was stirred at room temperature for 3 hours. After confirming the production of an iminium salt, the organic solvent was evaporated under reduced pressure. The residue was dissolved in EtOH (1.5 ml). To this was added $NaBH_4$ (12.09 mg) at 0° C. After warming to room temperature, the solution was stirred at room temperature for 15 hours. To the reaction solution was added water (30 ml), followed by extraction three times with EtOAc (20 ml). The organic layer was combined, washed with saturated brine, dried over anhydrous $MgSO_4$, and then filtered, and the filtrate was concentrated. The residue was purified by silica gel column chromatography (automatic purifier, chloroform:$CH_3OH$=100:0 to 90:10) to obtain N-methyl-1-(4-{5-[3-(trifluoromethyl)-4-(2,2,2-trifluoro-1-methylethoxy)phenyl]-1,2,4-oxadiazol-3-yl}-1H-indol-3-yl)methanamine (87.4 mg) as a white solid.

Example 15

To a solution of 4-{5-[3-(trifluoromethyl)-4-(2,2,2-trifluoro-1-methylethoxy)phenyl]-1,2,4-oxadiazol-3-yl}indoline (100 mg) in DMF (1.0 ml) was added 60% NaH (10.9 mg) at 0° C., followed by stirring at room temperature for 0.5 hour. Acetyl chloride (24.1 µl) was added thereto at 0° C., followed by stirring at room temperature for 3 hours. To the reaction solution was added water (30 ml), followed by extraction three times with EtOAc (20 ml). The organic layer was washed with saturated brine, dried over anhydrous $MgSO_4$, and then filtered, and the filtrate was concentrated. The residue was purified by silica gel column chromatography (automatic purifier, n-hexane:EtOAc=90:10 to 60:40) to obtain 1-acetyl-4-{5-[3-(trifluoromethyl)-4-(2,2,2-trifluoro-1-methylethoxy)phenyl]-1,2,4-oxadiazol-3-yl}indoline (56.8 mg) as a white crystal.

Example 16

To a solution of 4-{5-[3-(trifluoromethyl)-4-(2,2,2-trifluoro-1-methylethoxy)phenyl]-1,2,4-oxadiazol-3-yl}-1H-indole (80 mg) in DMF (0.80 ml) was added 60% NaH (8.7 mg) at 0° C., followed by stirring at room temperature for 0.5 hour. Methanesulfonyl chloride (21.1 μl) was added thereto at 0° C., followed by stirring at room temperature for 3 hours. To the reaction solution was added water (30 ml), followed by extraction three times with EtOAc (20 ml). The organic layer was combined, washed with saturated brine, dried over anhydrous $MgSO_4$, and then filtered, and the filtrate was concentrated. The filtrate was purified by silica gel column chromatography (automatic purifier, chloroform:$CH_3OH$=100:0 to 98:2) to obtain 1-(methylsulfonyl)-4-{5-[3-(trifluoromethyl)-4-(2,2,2-trifluoro-1-methylethoxy)phenyl]-1,2,4-oxadiazol-3-yl}-1H-indole (15.6 mg) as a white solid.

Example 17

4-{5-[3-(Trifluoromethyl)-4-(2,2,2-trifluoro-1-methylethoxy)phenyl]-1,2,4-oxadiazol-3-yl}-1H-indole (100 mg) was dissolved in DMF (1.0 ml), followed by addition of 60% NaH (10.9 mg) at 0° C., and stirring at room temperature for 0.5 hour. Methyl chloride carbonate (26.3 μl) was added thereto at 0° C., followed by stirring at room temperature for 3 hours. To the reaction solution was added water (30 ml), followed by extraction three times with EtOAc (20 ml), the organic layer was combined, washed with saturated brine, dried over anhydrous $MgSO_4$, and then filtered, and the filtrate was concentrated. The residue was purified by silica gel column chromatography (automatic purifier, chloroform: $CH_3OH$=100:0 to 98:2) to obtain methyl 4-{5-[3-(trifluoromethyl)-4-(2,2,2-trifluoro-1-methylethoxy)phenyl]-1,2,4-oxadiazol-3-yl}-1H-indole-1-carboxylate (98.6 mg) as a white solid.

Example 18

To a solution of 3-(5-{5-[3-(trifluoromethyl)-4-(2,2,2-trifluoro-1-methylethoxy)phenyl]-1,2,4-oxadiazol-3-yl}-1H-benzimidazol-2-yl)propanoic acid (23.5 mg) in dichloromethane (0.7 ml) were added oxalyl chloride (0.01 ml) and a few drops of DMF, followed by stirring at room temperature for 1 hour. The reaction mixture was concentrated to remove the solvent and the reagent. To a solution of the residue in THF was added $NH_4OH$, followed by further stirring for 1 hour. To the reaction solution was added a saturated aqueous $NH_4Cl$ solution, followed by extraction with EtOAc. The organic layer was dried over anhydrous $MgSO_4$, and the filtrate was concentrated. The residue was purified by silica gel column chromatography (chloroform:$CH_3OH$=10:1) to obtain colorless powders. To a solution of the colorless powders in EtOAc was added a solution of 4N—HCl in EtOAc. The reaction mixture was concentrated, and the residue was powdered and washed with IPE to obtain 3-(5-{5-[3-(trifluoromethyl)-4-(2,2,2-trifluoro-1-methylethoxy)phenyl]-1,2,4-oxadiazol-3-yl}-1H-benzimidazol-2-yl)propanamide hydrochloride as pale yellow powders.

Example 19

To a solution of (4-{5-[3-(trifluoromethyl)-4-(2,2,2-trifluoro-1-methylethoxy)phenyl]-1,2,4-oxadiazol-3-yl}-1H-indol-1-yl)acetic acid (150 mg) a HOBt(65 mg) in DMF (1.5 ml) was added EDCl/HCl (69 mg) at 0° C., followed by stirring at room temperature for 1 hour. After cooling to 0° C. again, 1-pyridin-2-ylmethanamine (39 mg) was added thereto, followed by stirring at room temperature for 15 hours. To the reaction solution was added a saturated aqueous $NaHCO_3$ solution to complete the reaction. It was extracted with EtOAc, the organic layer was washed with saturated brine, dried over anhydrous $MgSO_4$, and then filtered, and the filtrate was concentrated under reduced pressure. The residue was purified by silica gel column chromatography (chloroform:$CH_3OH$=100:0 to 95:5) to obtain N-(pyridin-2-ylmethyl)-2-(4-{5-[3-(trifluoromethyl)-4-(2,2,2-trifluoro-1-methylethoxy)phenyl]-1,2,4-oxadiazol-3-yl}-1H-indol-1-yl)acetamide (157.8 mg) as a white solid. To a solution of N-(pyridin-2-ylmethyl)-2-(4-{5-[3-(trifluoromethyl)-4-(2,2,2-trifluoro-1-methylethoxy)phenyl]-1,2,4-oxadiazol-3-yl}-1H-indol-1-yl)acetamide (120 mg) in methylene chloride (2.4 ml) was added dropwise 10 equivalents of 4M HCl/dioxane, followed by stirring for 1 hour. The reaction mixture was concentrated under reduced pressure, and powdered/washed with IPE. The obtained solid was collected by filtration, and dried to obtain N-(pyridin-2-ylmethyl)-2-(4-{5-[3-(trifluoromethyl)-4-(2,2,2-trifluoro-1-methylethoxy) phenyl]-1,2,4-oxadiazol-3-yl}-1H-indol-1-yl)acetamide hydrochloride (126 mg) as a white solid.

Example 20

To a solution of [4-(5-{3-(trifluoromethyl)-4-[(1S)-2,2,2-trifluoro-1-methylethoxy]phenyl}-1,2,4-oxadiazol-3-yl)-1H-indol-1-yl]acetic acid (100 mg) in DMF (1 ml) was added CDI (39 mg), and after 30 min, methanesulfonamide (23 mg) and 2,3,4,6,7,8,9,10-octahydropyrimide[1,2-a]azepine (37 mg) were added thereto, followed by stirring at room temperature for 15 hours. The reaction mixture was added with water to complete the reaction. It was extracted with EtOAc, the obtained organic layer was washed with saturated brine, dried over anhydrous $MgSO_4$, and then filtered, and the filtrate was concentrated. The residue was purified by silica gel column chromatography (chloroform:$CH_3OH$=100:0 to 90:10) to obtain N-(methylsulfonyl)-2-[4-(5-{3-(trifluoromethyl)-4-[(1S)-2,2,2-trifluoro-1-methylethoxy]phenyl}-1,2,4-oxadiazol-3-yl)-1H-indol-1-yl]acetamide (56.4 mg) as a white solid.

Example 21

$POCl_3$ (158.4 μl) was added dropwise to a DMF solution (4 ml) at 0° C. After warming to room temperature, it was stirred for 0.5 hour. Then, a solution of 4-{5-[3-(trifluoromethyl)-4-(2,2,2-trifluoro-1-methylethoxy)phenyl]-1,2,4-oxadiazol-3-yl}-1H-indole (500.0 mg) in DMF (1 ml) was added thereto at 0° C., followed by stirring at room temperature for 15 hours. After cooling to 0° C., to the reaction solution was added a 1M aqueous NaOH solution for adjustment of its pH to 9 to 10. This solution was stirred at 100° C. for 1 hour. After being left to be cooled, to the reaction solution was added water (30 ml), followed by extraction three times with EtOAc (20 ml). The organic layer was combined, washed with saturated brine, dried over anhydrous $MgSO_4$, and then filtered, and the filtrate was concentrated. The residue was purified by silica gel column chromatography (automatic purifier, n-hexane, EtOAc=90:10 to 70:30) to obtain 4-{5-[3-(trifluoromethyl)-4-(2,2,2-trifluoro-1-methylethoxy)phenyl]-1,2,4-oxadiazol-3-yl}-1H-indole-3-carboaldehyde (456.7 mg) as a white solid.

Example 22

To a mixed solution of 5-[3-(1H-benzimidazol-6-yl)-1,2,4-oxadiazol-5-yl]-2-(2,2,2-trifluoro-1-methylethoxy)benzaldehyde (83 mg), potassium dihydrogen phosphate (421 mg), and 2-methyl-2-butene (0.5 ml) in tBuOH (2 ml) and water (0.5 ml) was added sodium chlorite (187 mg) at room temperature. The mixed reaction solution was stirred at room temperature for 3 hours, followed by dilution with water (10 ml), and extraction with EtOAc (20 ml). The organic layer

Example 23

To a solution of 2-[2-(methylthio)ethyl]-5-{5-[3-(trifluoromethyl)-4-(2,2,2-trifluoro-1-methylethoxy)phenyl]-1,2,4-oxadiazol-3-yl}-1H-benzimidazole (400 mg) in dichloromethane (8.0 ml) was added mCPBA (534 mg), followed by stirring at room temperature for 3 hours. To the reaction mixture was added a $Na_2S_2O_4$ aqueous solution, followed by stirring for 1 hour. The reaction solution was extracted three times with EtOAc, and the organic layer was combined, dried over anhydrous $MgSO_4$, filtered, and then concentrated. The residue was purified by silica gel chromatography (chloroform:$CH_3OH$=10:1) to obtain a yellow oily substance. This was dissolved in EtOAc, and a 4M-HCl/EtOAc solution was added thereto, followed by concentration. The residue was washed with IPE to obtain 2-[2-(methylsulfonyl)ethyl]-5-{5-[3-(trifluoromethyl)-4-(2,2,2-trifluoro-1-methylethoxy)phenyl]-1,2,4-oxadiazol-3-yl}-1H-benzimidazole hydrochloride (146 mg) as pale yellow powders.

Example 24

To a reaction mixture of 2-but-3-en-1-yl-5-{5-[3-(trifluoromethyl)-4-(2,2,2-trifluoro-1-methylethoxy)phenyl]-1,2,4-oxadiazol-3-yl}-1H-benzimidazole (200 mg) in acetone (4 ml) and water (1 ml) were added tetraoxoosmium (51 mg) and 4-methylmorpholine 4-oxide (94 mg), followed by stirring overnight. The reaction mixture was filtered, and to the filtrate was added an aqueous sodium thiosulfate solution, followed by stirring for 1 hour. The solution was extracted with chloroform, and the organic layer was concentrated. The residue was purified by silica gel column chromatography (chloroform-$CH_3OH$), and concentrated, and the obtained colorless powder was added with a solution of HCl in ethanol, and dissolved therein, followed by concentration. The residue was powdered/washed with diisopropyl ether to obtain 4-(5-{5-[3-(trifluoromethyl)-4-(2,2,2-trifluoro-1-methylethoxy)phenyl]-1,2,4-oxadiazol-3-yl}-1H-benzimidazol-2-yl)butane-1,2-diol hydrochloride (102.3 mg).

Example 25

To a solution of 3-(4-{5-[3-(trifluoromethyl)-4-(2,2,2-trifluoro-1-methylethoxy)phenyl]-1,2,4-oxadiazol-3-yl}-2,3-dihydro-1H-indol-1-yl)propanamide (100 mg) in chloroform (1 ml) was added manganese dioxide (67.6 mg), followed by reflux for 15 hours. The reaction solution was left to be cooled to room temperature, and filtered through Celite to remove manganese dioxide. The filtrate was concentrated under reduced pressure. The residue was purified by silica gel column chromatography (chloroform:$CH_3OH$=100:0 to 90:10) to obtain 3-(4-{5-[3-(trifluoromethyl)-4-(2,2,2-trifluoro-1-methylethoxy)phenyl]-1,2,4-oxadiazol-3-yl}-1H-indol-1-yl) propanamide (46.3 mg).

Example 26

To a solution 4-{5-[3-(trifluoromethyl)-4-(2,2,2-trifluoro-1-methylethoxy)phenyl]-1,2,4-oxadiazol-3-yl}-1H-indole (100 mg) in AcOH (3 ml) was added portionwise sodium cyanoborate (29 mg). The reaction mixture was stirred at room temperature for 2 hours. The reaction mixture was diluted with water, alkalified with a 1M aqueous NaOH solution, and extracted with EtOAc. The organic layer was washed with saturated brine, dried over anhydrous $MgSO_4$, and then filtered, the filtrate was concentrated, and the residue was purified by silica gel column chromatography (n-hexane: EtOAc=90:10 to 75:25), and washed with n-hexane to obtain 4-{5-[3-(trifluoromethyl)-4-(2,2,2-trifluoro-1-methylethoxy)phenyl]-1,2,4-oxadiazol-3-yl}indoline (90 mg) as a pale yellow solid.

Example 27

To a solution of 5-[3-(1H-benzimidazol-6-yl)-1,2,4-oxadiazol-5-yl]-2-(2,2,2-trifluoro-1-methylethoxy)benzaldehyde (80 mg) in ethanol (3 ml) was added $NaBH_4$ (9 mg) at 0° C. After stirring at room temperature for 0.5 hour, a saturated $NH_4Cl$ solution (10 ml) was added thereto, followed by extraction with EtOAc (20 ml). The organic layer was washed with saturated brine, dried over anhydrous $MgSO_4$, and then filtered, and the filtrate was concentrated. To a solution of the residue (78 mg) in dioxane was added a 4M HCl/dioxane solution, followed by concentration. The resulting powder was recrystallized with IPA (10 ml) to obtain [5-[3-(1H-benzimidazol-5-yl)-1,2,4-oxadiazol-5-yl]-2-(2,2,2-trifluoro-1-methylethoxy)phenyl]methanol hydrochloride (70 mg) as white powders.

Example 28

A solution of 5-methyl-6-{5-[3-trifluoro)-4-(2,2,2-trifluoro-1-methylethoxy)phenyl]-1,2,4-oxadiazol-3-yl}imidazo[1,2-a]pyridine (120 mg) and NCS in THF/EtOH (1/1) was stirred at 80° C. for overnight. It was concentrated, and the obtained residue was purified by silica gel column chromatography ($CH_3OH$/chloroform 0 to 5%) to obtain 3-chloro-5-methyl-6-{5-[3-(trifluoromethyl)-4-(2,2,2-trifluoro-1-methylethoxy)phenyl]-1,2,4-oxadiazol-3-yl}imidazo[1,2-a]pyridine (45 mg) as a pale yellow solid.

Example 29

To a solution of 5-{5-[3-(trifluoromethyl)-4-(2,2,2-trifluoro-1-methylethoxy)phenyl]-1,2,4-oxadiazol-3-yl}imidazo[1,2-a]pyridine (150 mg) in ethanol was added NCS (67 mg) at room temperature, followed by stirring at 80° C. for 15 hours. To the reaction solution was added water, followed by extraction with EtOAc. The organic layer was washed with saturated brine, dried over anhydrous $MgSO_4$, and then filtered, and the filtrate was concentrated. It was purified by silica gel column chromatography (n-hexane: EtOAc=90:10 to 75:25) to obtain 3-chloro-5-{5-[3-(trifluoromethyl)-4-(2,2,2-trifluoro-1-methylethoxy)phenyl]-1,2,4-oxadiazol-3-yl}imidazo[1,2-a]pyridine (110.4 mg) as a white solid. To a solution of 3-chloro-5-{5-[3-(trifluoromethyl)-4-(2,2,2-trifluoro-1-methylethoxy)phenyl]-1,2,4-oxadiazol-3-yl}imidazo[1,2-a]pyridine (100 mg) in methylene chloride (2 ml) was added dropwise 10 equivalents of 4M HCl/dioxane at room temperature. After stirring at room temperature as it was for 1 hour, it was concentrated under reduced pressure. It was powdered/washed with diisopropyl ether, and then collected by filtration to obtain 3-chloro-5-{5-[3-(trifluoromethyl)-4-(2,2,2-trifluoro-1-methylethoxy)phenyl]-1,2,4-oxadiazol-3-yl}imidazo[1,2-a]pyridine hydrochloride (102.6 mg) as a white solid.

Example 30

1-(2-{[Tertiary-butyldimethylsilyl]oxy}ethyl)-4-{5-[3-(trifluoromethyl)-4-(2,2,2-trifluoro-1-methylethoxy)phewas washed with saturated brine, dried over anhydrous $MgSO_4$, and then filtered, and the filtrate was concentrated. To a solution of the residue in dioxane was added a 4 N HCl-dioxane solution, followed by concentration. The resulting powder was recrystallized with IPA (10 ml) to obtain 5-[3-(1H-benzimidazol-5-yl)-1,2,4-oxadiazol-5-yl]-2-(2,2,2-trifluoro-1-methylethoxy)benzoic acid hydrochloride (80 mg) as white powders.

nyl]-1,2,4-oxadiazol-3-yl}-1H-indole (60 mg) was dissolved in THF (1.2 ml), and TBAF (150 μl) was added thereto at 0° C., followed by stirring at room temperature for 3.0 hours. To the reaction solution was added water (30 ml), followed by extraction three times with EtOAc (20 ml). The organic layer was combined, washed with saturated brine, dried over anhydrous MgSO$_4$, and then filtered, and the filtrate was concentrated. The residue was purified by silica gel column chromatography (automatic purifier, chloroform:CH$_3$OH=100:0 to 90:10) to obtain 2-(4-{5-[3-(trifluoromethyl)-4-(2,2,2-trifluoro-1-methylethoxy)phenyl]-1,2,4-oxadiazol-3-yl}1H-indol-1-yl)ethanol (36.5 mg) as a white solid.

Example 31

To a solution of tertiary-butyl 4-{[4-(5-{3-(trifluoromethyl)-4-[(1S)-2,2,2-trifluoro-1-methylethoxy]phenyl}-1,2,4-oxadiazol-3-yl)-1H-indol-1-yl]acetyl}piperazine-1-carboxylate (70.7 mg) in methylene chloride (1 ml) was added dropwise 10 equivalents of 4M HCl/dioxane, followed by stirring at room temperature for 3 hours. After 5 hours, the reaction solution was concentrated. With addition of diisopropyl ether, a white solid was precipitated. The white solid was washed with IPE to obtain 1-(2-oxo-2-piperazin-1-yl-ethyl)-4-(5-{3-(trifluoromethyl)-4-[(1S)-2,2,2-trifluoro-1-methylethoxy]phenyl}-1,2,4-oxadiazol-3-yl)-1H-indole hydrochloride (58.9 mg) as a pale red solid.

In following tables, the structural formulae of the Example compounds are shown. Ex: Example No.

TABLE 55-continued
| Ex | Structure |
|---|---|
| 12 | 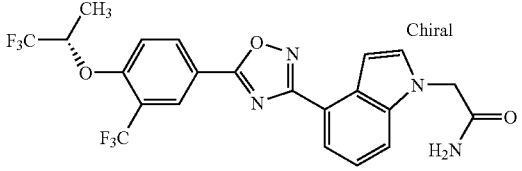 Chiral |
| 13 | 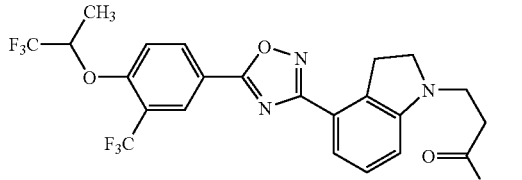 |
| 14 | 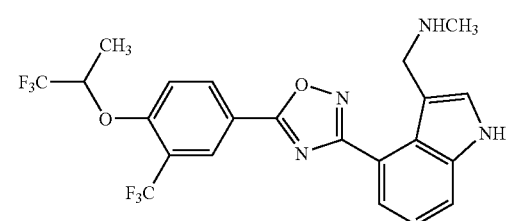 |
| 15 | 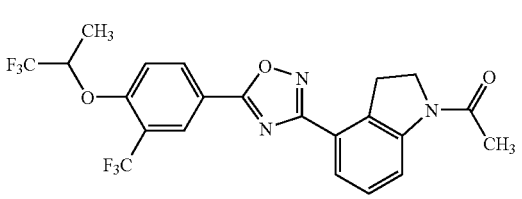 |
TABLE 56
| Ex | Structure |
|---|---|
| 16 | 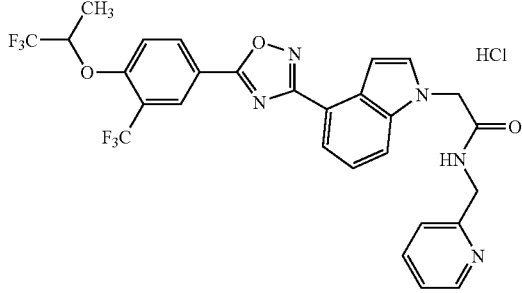 |
| 17 | 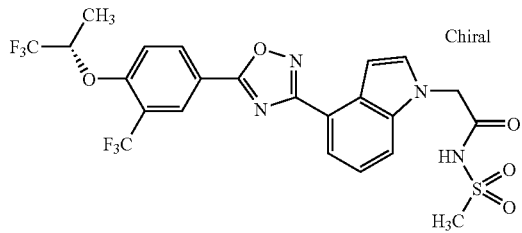 |
| 18 | 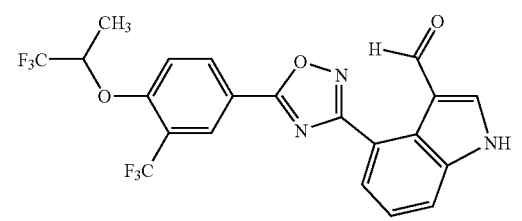 HCl |
TABLE 56-continued
| Ex | Structure |
|---|---|
| 19 | 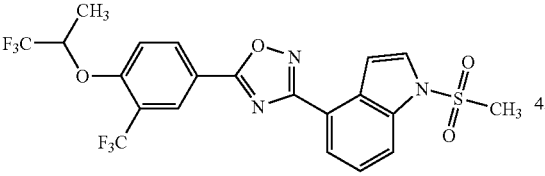 HCl |
| 20 | 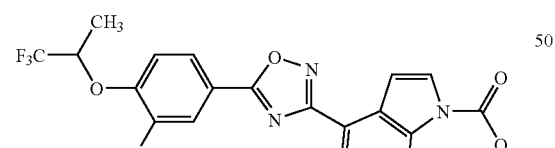 Chiral |
| 21 | 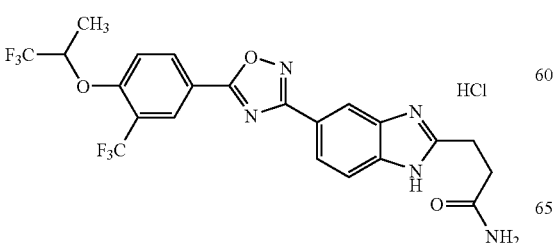 |
| 22 | 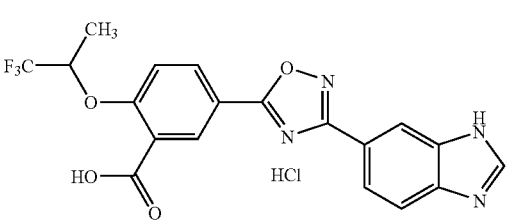 HCl |
| 23 | 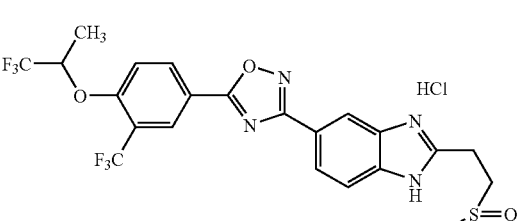 HCl |
| 24 | 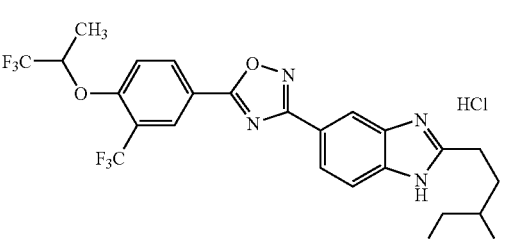 HCl |

TABLE 56-continued

| Ex | Structure |
|---|---|
| 25 | (3-trifluoromethyl-4-(1,1,1-trifluoropropan-2-yloxy)phenyl)-oxadiazolyl-indole-propanamide |
| 26 | (3-trifluoromethyl-4-(1,1,1-trifluoropropan-2-yloxy)phenyl)-oxadiazolyl-indoline |
| 27 | (hydroxymethyl-(1,1,1-trifluoropropan-2-yloxy)phenyl)-oxadiazolyl-benzimidazole HCl |

TABLE 57

| Ex | Structure |
|---|---|
| 28 | (3-trifluoromethyl-4-(1,1,1-trifluoropropan-2-yloxy)phenyl)-oxadiazolyl-methyl-chloro-imidazopyridine |
| 29 | (3-trifluoromethyl-4-(1,1,1-trifluoropropan-2-yloxy)phenyl)-oxadiazolyl-chloro-imidazopyridine HCl |
| 30 | (3-trifluoromethyl-4-(1,1,1-trifluoropropan-2-yloxy)phenyl)-oxadiazolyl-indole-ethanol |

TABLE 57-continued

| Ex | Structure |
|---|---|
| 31 | Chiral (3-trifluoromethyl-4-(1,1,1-trifluoropropan-2-yloxy)phenyl)-oxadiazolyl-indolyl-acetyl-piperazine HCl |
| 32 | (3-trifluoromethyl-4-(1,1,1-trifluoropropan-2-yloxy)phenyl)-oxadiazolyl-imidazopyridine |
| 33 | (3-trifluoromethyl-4-(1,1,1-trifluoropropan-2-yloxy)phenyl)-oxadiazolyl-imidazopyridine HCl |
| 34 | (3-trifluoromethyl-4-(1,1,1-trifluoropropan-2-yloxy)phenyl)-oxadiazolyl-methyl-imidazopyridine |
| 35 | (3-trifluoromethyl-4-(1,1,1-trifluoropropan-2-yloxy)phenyl)-oxadiazolyl-methyl-imidazopyridine HCl |
| 36 | (3-trifluoromethyl-4-(1,1,1-trifluoropropan-2-yloxy)phenyl)-oxadiazolyl-dimethyl-imidazopyridine |
| 37 | (3-trifluoromethyl-4-(1,1,1-trifluoropropan-2-yloxy)phenyl)-oxadiazolyl-methyl-benzimidazole HCl |

TABLE 57-continued
| Ex | Structure |
|---|---|
| 38 | 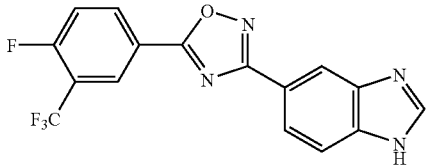 |
| 39 | 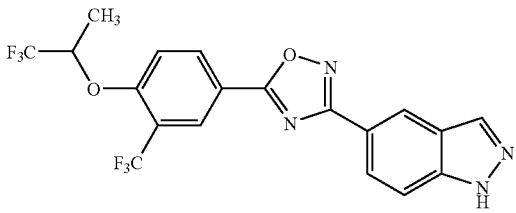 |
| 40 | 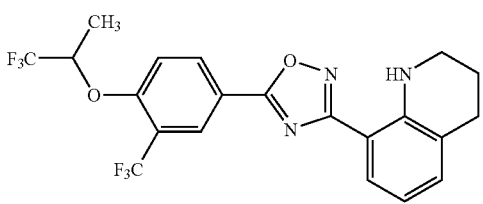 |
| 41 | 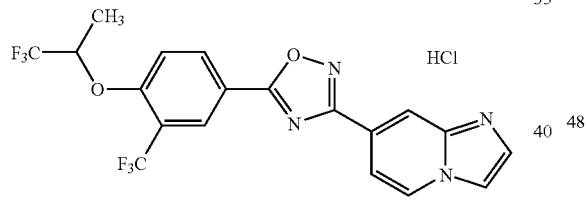 |
TABLE 58
| Ex | Structure |
|---|---|
| 42 | 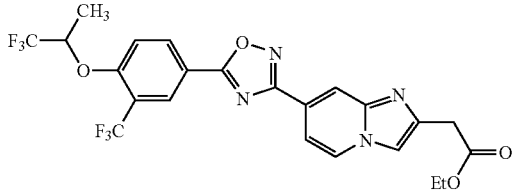 |
| 43 | 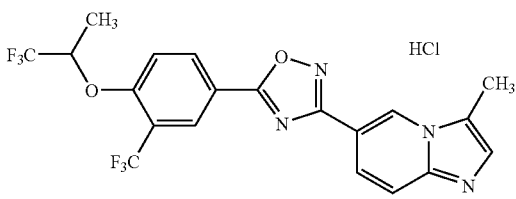 |
TABLE 58-continued
| Ex | Structure |
|---|---|
| 44 | 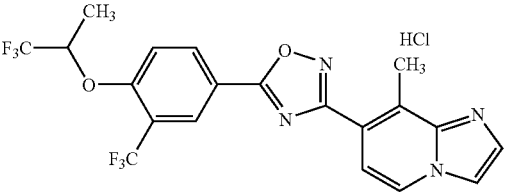 |
| 45 | 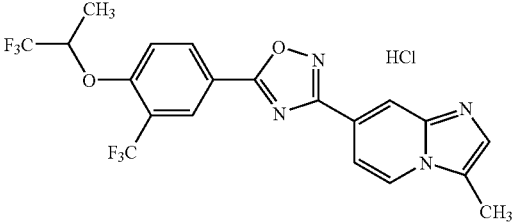 |
| 46 | 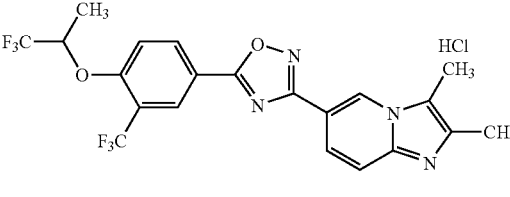 |
| 47 | 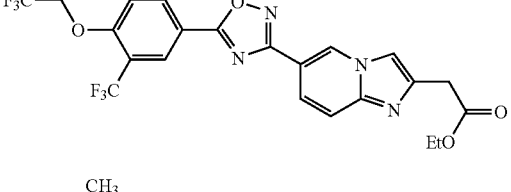 |
| 48 | 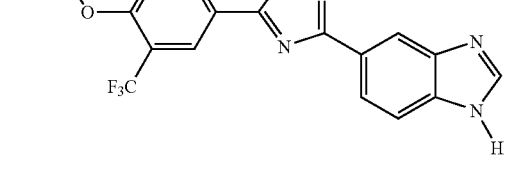 |
| 49 | 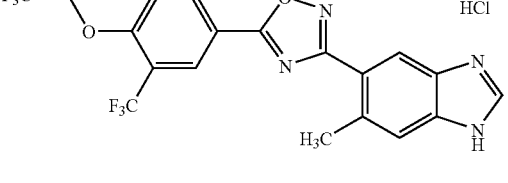 |
| 50 | 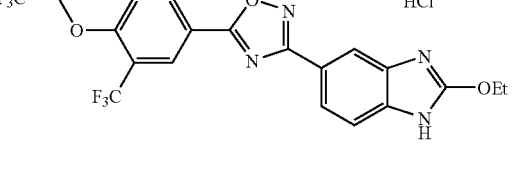 |

TABLE 58-continued
| Ex | Structure |
|---|---|
| 51 | 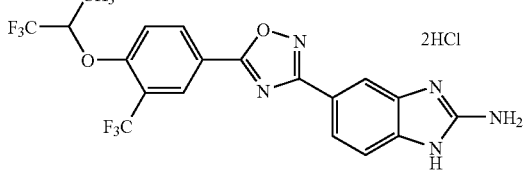 2HCl |
| 52 | 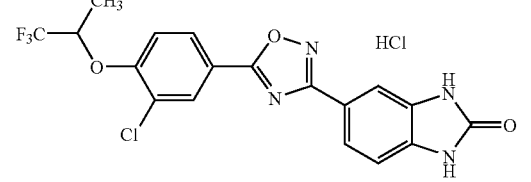 HCl |
| 53 | 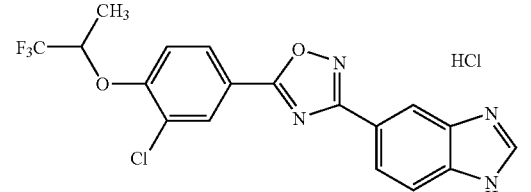 HCl |
| 54 | 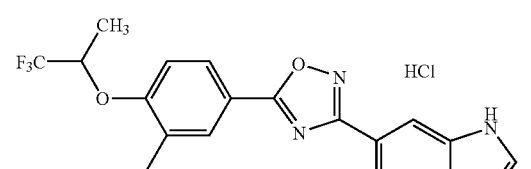 HCl |
| 55 | 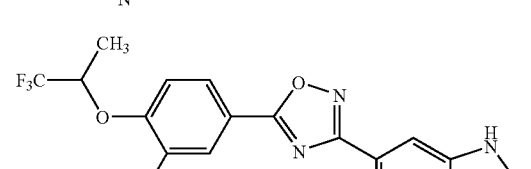 |
TABLE 59
| Ex | Structure |
|---|---|
| 56 | 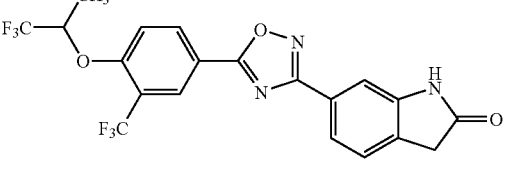 HCl |
| 57 | 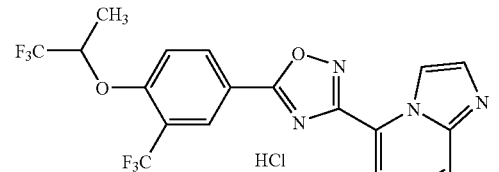 HCl |
TABLE 59-continued
| Ex | Structure |
|---|---|
| 58 | 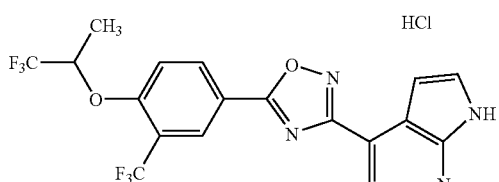 |
| 59 | 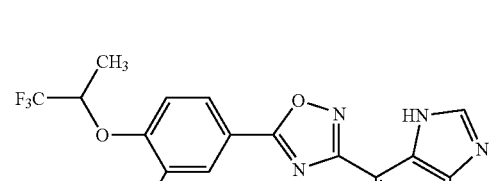 HCl |
| 60 | 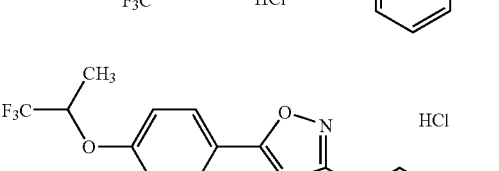 |
| 61 | 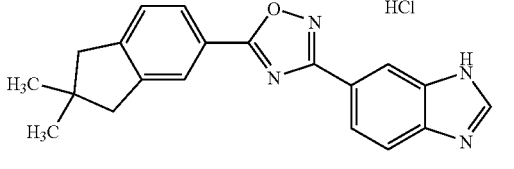 HCl |
| 62 | 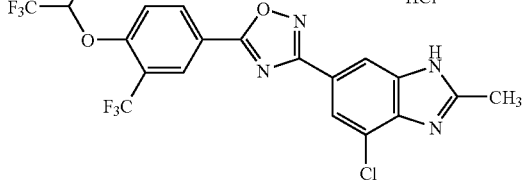 HCl |
| 63 | 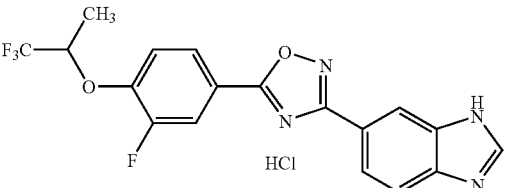 HCl |
| 64 | 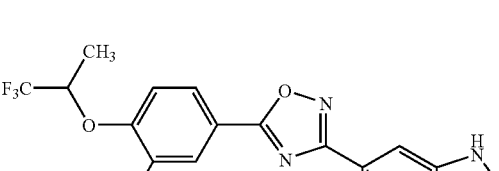 HCl |

TABLE 59-continued

| Ex | Structure |
|---|---|
| 65 | [structure: 4-(1,1,1-trifluoropropan-2-yloxy)-3-(trifluoromethyl)phenyl-1,2,4-oxadiazole linked to 1H-indazol-6-yl] |
| 66 | [structure: same aryl-oxadiazole linked to 1H-benzotriazol-5-yl] |
| 67 | [structure: same aryl-oxadiazole linked to 1H-indol-4-yl] |
| 68 | [structure: same aryl-oxadiazole linked to 4-methyl-1H-benzimidazol-6-yl, HCl] |
| 69 | [structure: 4-(1,1,1-trifluoropropan-2-yloxy)-3-methoxyphenyl oxadiazole linked to 1H-benzimidazol-5-yl, HCl] |
| 70 | [structure: same aryl-oxadiazole linked to 1H-indol-5-yl] |
| 71 | [structure: same aryl-oxadiazole linked to 4-methylquinolin-3-yl, HCl] |

TABLE 60

| Ex | Structure |
|---|---|
| 72 | [structure: aryl-oxadiazole linked to 2-(2-ethoxycarbonylethyl)-1H-benzimidazol-5-yl] |
| 73 | [structure: aryl-oxadiazole linked to 7-methyl-1H-benzimidazol-5-yl, HCl] |
| 74 | [structure: aryl-oxadiazole linked to 1H-pyrrolo[2,3-b]pyridin-6-yl] |
| 75 | [structure: aryl-oxadiazole linked to [1,2,4]triazolo[1,5-a]pyridin-6-yl] |
| 76 | [structure: aryl-oxadiazole linked to 3-amino-1H-indazol-6-yl] |
| 77 | [structure: aryl-oxadiazole linked to 3H-imidazo[4,5-b]pyridin-6-yl, HCl] |
| 78 | [structure: aryl-oxadiazole linked to 1H-pyrrolo[2,3-b]pyridin-6-yl] |

TABLE 60-continued

| Ex | Structure |
|---|---|
| 79 | [structure] |
| 80 | [structure] HCl |
| 81 | [structure] |
| 82 | [structure] |
| 83 | [structure] |
| 84 | [structure] |
| 85 | [structure] |
| 86 | [structure] |

TABLE 60-continued

| Ex | Structure |
|---|---|
| 87 | [structure] HCl |

TABLE 61

| Ex | Structure |
|---|---|
| 88 | [structure] |
| 89 | [structure] Chiral |
| 90 | [structure] Chiral |
| 91 | [structure] |
| 92 | [structure] |
| 93 | [structure] HCl |

TABLE 61-continued

| Ex | Structure |
|---|---|
| 94 | (structure with HCl) |
| 95 | (structure with HCl) |
| 96 | (structure with HCl) |
| 97 | (structure with HCl) |
| 98 | (structure) |
| 99 | (structure) |
| 100 | (structure) |
| 101 | (structure) |
| 102 | (structure) |
| 103 | (structure with HCl) |

TABLE 62

| Ex | Structure |
|---|---|
| 104 | (structure with HCl) |
| 105 | (structure with HCl) |
| 106 | (structure with HCl) |
| 107 | (structure with HCl) |

TABLE 62-continued

| Ex | Structure |
|---|---|
| 108 | 4-benzyloxy-3-trifluoromethylphenyl-5-(1,2,4-oxadiazol-3-yl)-1H-benzimidazole, HCl |
| 109 | 4-hydroxy-3-trifluoromethylphenyl-5-(1,2,4-oxadiazol-3-yl)-1H-benzimidazole, HCl |
| 110 | 4-(2,2-difluoroethoxy)-3-trifluoromethylphenyl-5-(1,2,4-oxadiazol-3-yl)-1H-benzimidazole, HCl |
| 111 | 2-(2-methyl-4-(3-(1H-benzimidazol-5-yl)-1,2,4-oxadiazol-5-yl)phenoxy)propanamide, HCl |
| 112 | 4-(pyridin-3-yloxy)-3-trifluoromethylphenyl-5-(1,2,4-oxadiazol-3-yl)-1H-benzimidazole, 2HCl |
| 113 | 4-(sec-butoxy)-3-trifluoromethylphenyl-5-(1,2,4-oxadiazol-3-yl)-1H-benzimidazole, HCl |
| 114 | 4-(2-methylallyloxy)-3-trifluoromethylphenyl-5-(1,2,4-oxadiazol-3-yl)-1H-benzimidazole, HCl |

TABLE 62-continued

| Ex | Structure |
|---|---|
| 115 | 4-(but-3-en-2-yloxy)-3-trifluoromethylphenyl-5-(1,2,4-oxadiazol-3-yl)-1H-benzimidazole |
| 116 | 4-(3-methylbut-2-enyloxy)-3-trifluoromethylphenyl-5-(1,2,4-oxadiazol-3-yl)-1H-benzimidazole |
| 117 | 4-morpholino-3-trifluoromethylphenyl-5-(1,2,4-oxadiazol-3-yl)-1H-benzimidazole, 2HCl |

TABLE 63

| Ex | Structure |
|---|---|
| 118 | 4-(sec-butylthio)-3-trifluoromethylphenyl-5-(1,2,4-oxadiazol-3-yl)-1H-benzimidazole |
| 119 | 4-((R)-1,1,1-trifluoropropan-2-yloxy)-3-trifluoromethylphenyl-5-(1,2,4-oxadiazol-3-yl)-1H-benzimidazole, HCl |
| 120 | 4-((S)-1,1,1-trifluoropropan-2-yloxy)-3-trifluoromethylphenyl-5-(1,2,4-oxadiazol-3-yl)-1H-benzimidazole, HCl |

TABLE 63-continued

| Ex | Structure |
|---|---|
| 121 | (phenoxy-CF3-phenyl-oxadiazole-benzimidazole) |
| 122 | (F2HCF2CO-CF3-phenyl-oxadiazole-benzimidazole) |
| 123 | (difluoroisopropoxy-CF3-phenyl-oxadiazole-benzimidazole) |
| 124 | (diene-oxy-CF3-phenyl-oxadiazole-benzimidazole, HCl) |
| 125 | (cyclohexyloxy-CF3-phenyl-oxadiazole-indole) |
| 126 | (phenoxy-CF3-phenyl-oxadiazole-indole-CH2C(O)NH2) |
| 127 | (CF3-CH(CH3)-O-CF3-phenyl-oxadiazole-indole-CH2C(O)NH2, Chiral) |

TABLE 63-continued

| Ex | Structure |
|---|---|
| 128 | (F3CCH2O-Cl-phenyl-oxadiazole-indole-CH2C(O)NH2) |
| 129 | (CF3-CH(CH3)-O-CF3-phenyl-oxadiazole-azaindole, HCl) |
| 130 | (F3CCH2O-CF3-phenyl-oxadiazole-azaindole, HCl) |
| 131 | (CHF2CH2O-CF3-phenyl-oxadiazole-azaindole, HCl) |
| 132 | (phenoxy-CF3-phenyl-oxadiazole-azaindole, HCl) |
| 133 | (F3CCH2O-CN-phenyl-oxadiazole-indole-CH2C(O)NH2) |

TABLE 64

| Ex | Structure |
|---|---|
| 134 | (cyclohexenyloxy-CF3-phenyl-oxadiazole-indole-CH2C(O)NH2) |

TABLE 64-continued

| Ex | Structure |
|---|---|
| 135 | (chemical structure) |
| 136 | (chemical structure) |
| 137 | (chemical structure) |
| 138 | (chemical structure) |
| 139 | (chemical structure) |
| 140 | (chemical structure) |
| 141 | (chemical structure) |
| 142 | (chemical structure) |
| 143 | (chemical structure) |
| 144 | (chemical structure) |
| 145 | (chemical structure) |
| 146 | (chemical structure) |
| 147 | (chemical structure) |

TABLE 65

| Ex | Structure |
|---|---|
| 148 | (chemical structure) |
| 149 | (chemical structure) |

TABLE 65-continued

| Ex | Structure |
|---|---|
| 150 | 2-(4-(5-(5-chloro-6-isopropoxypyridin-3-yl)-1,2,4-oxadiazol-3-yl)-1H-indol-1-yl)acetamide |
| 151 | 1-methyl-4-(5-(4-(1,1,1-trifluoropropan-2-yloxy)-3-(trifluoromethyl)phenyl)-1,2,4-oxadiazol-3-yl)-1H-indole |
| 152 | 1-methyl-4-(5-(4-(1,1,1-trifluoropropan-2-yloxy)-3-(trifluoromethyl)phenyl)-1,2,4-oxadiazol-3-yl)-2,3-dihydro-1H-indole |
| 153 | methyl 2-(4-(5-(4-(1,1,1-trifluoropropan-2-yloxy)-3-(trifluoromethyl)phenyl)-1,2,4-oxadiazol-3-yl)-1H-indol-1-yl)acetate |
| 154 | ethyl 2-(5-(5-(4-(1,1,1-trifluoropropan-2-yloxy)-3-(trifluoromethyl)phenyl)-1,2,4-oxadiazol-3-yl)-1H-benzimidazol-1-yl)acetate |
| 155 | 2-(4-(5-(4-(1,1,1-trifluoropropan-2-yloxy)-3-(trifluoromethyl)phenyl)-1,2,4-oxadiazol-3-yl)-1H-benzimidazol-1-yl)acetamide HCl |
| 156 | 2-(7-(5-(4-(1,1,1-trifluoropropan-2-yloxy)-3-(trifluoromethyl)phenyl)-1,2,4-oxadiazol-3-yl)-1H-benzimidazol-1-yl)acetamide |
| 157 | 2-(4-(5-(3-(trifluoromethyl)-4-(trifluoromethoxy)phenyl)-1,2,4-oxadiazol-3-yl)-1H-indol-1-yl)acetamide |
| 158 | 2-(4-(5-(4-(1,3-difluoropropan-2-yloxy)-3-(trifluoromethyl)phenyl)-1,2,4-oxadiazol-3-yl)-1H-indol-1-yl)acetamide |
| 159 | 2-(4-(5-(4-(isopropylamino)-3-(trifluoromethyl)phenyl)-1,2,4-oxadiazol-3-yl)-1H-indol-1-yl)acetamide |
| 160 | 2-(4-(5-(4-(2,2-difluoroethoxy)-3-(trifluoromethyl)phenyl)-1,2,4-oxadiazol-3-yl)-1H-indol-1-yl)acetamide |
| 161 | 2-(4-(5-(3-methyl-4-(1,1,1-trifluoropropan-2-yloxy)phenyl)-1,2,4-oxadiazol-3-yl)-1H-indol-1-yl)acetamide |

TABLE 66

| Ex | Structure |
|---|---|
| 162 | 2-(4-(5-(4-(cyclohexyloxy)-3-(trifluoromethyl)phenyl)-1,2,4-oxadiazol-3-yl)-1H-indol-1-yl)acetamide |
| 163 | 2-(4-(5-(3-cyano-4-(1,1,1-trifluoropropan-2-yloxy)phenyl)-1,2,4-oxadiazol-3-yl)-1H-indol-1-yl)acetamide |

TABLE 66-continued
| Ex | Structure |
|---|---|
| 164 | 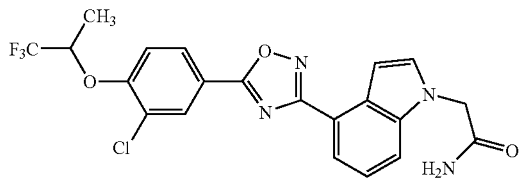 |
| 165 | 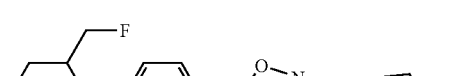 |
| 166 | 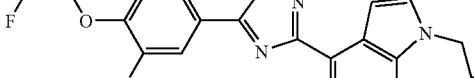 |
| 167 | 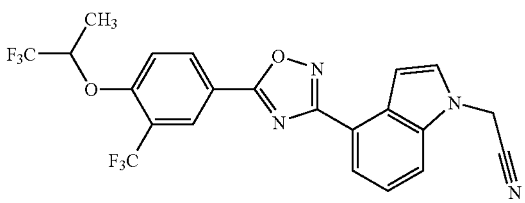 |
| 168 | Chiral 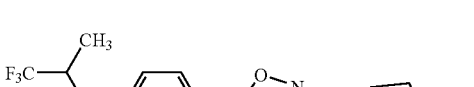 |
| 169 | 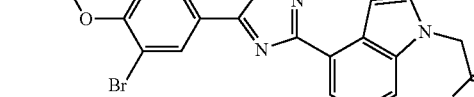 |
| 170 | Chiral  |
| 171 | HCl |
| 172 | 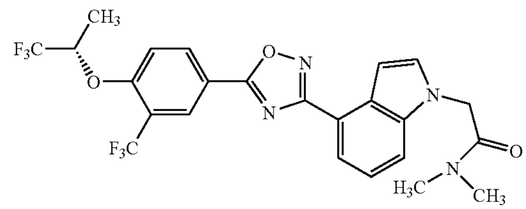 |
| 173 | Chiral |
| 174 | 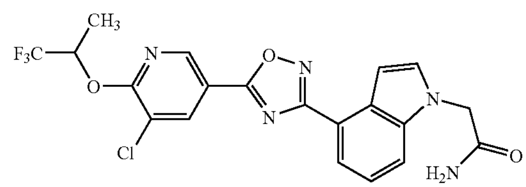 |
| 175 | 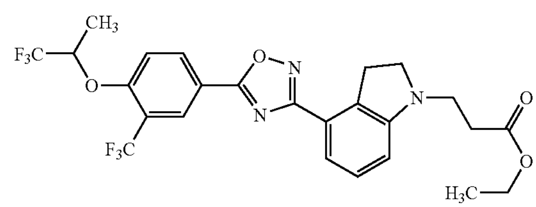 |
TABLE 67
| Ex | Structure |
|---|---|
| 176 | 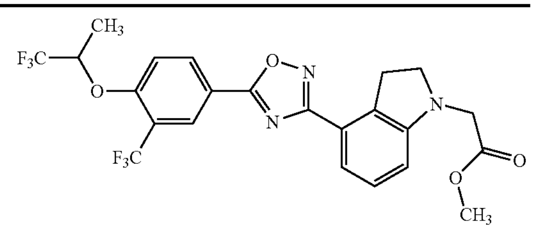 |
| 177 | 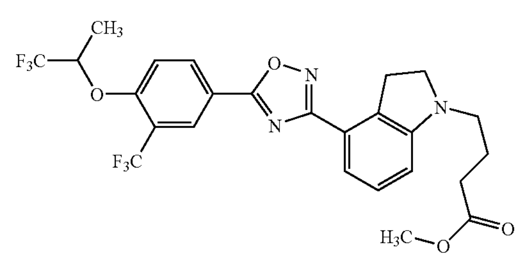 |

TABLE 67-continued

| Ex | Structure |
|---|---|
| 178 | [structure: 4-[3-(trifluoromethyl)-4-(2,2,2-trifluoro-1-methylethoxy)phenyl]-1,2,4-oxadiazol-3-yl-indoline-1-yl-N,N-dimethylacetamide] |
| 179 | [structure: indoline-1-yl-acetamide analog, H₂N-C(=O)-] |
| 180 | [structure: pyrrolopyridine analog, HCl salt, H₂N-C(=O)-] |
| 181 | [structure: indole analog, H₂N-C(=O)-] |
| 182 | [structure: indole with N-C(=O)-CH₂-O-CH₃] |
| 183 | [structure: indoline with N-CH₂-C(=O)-O-CH₃] |
| 184 | [structure: indole with N-C(=O)-CH₃ (acetyl)] |
| 185 | [structure: indoline with N-S(=O)₂-CH₃ (methanesulfonyl)] |
| 186 | [structure: Chiral; indole-N-CH₂-C(=O)-piperazine-N-Boc] |
| 187 | [structure: Chiral; indole-N-CH₂-C(=O)-NH-CH₂CH₂-NH-Boc] |
| 188 | [structure: Chiral; indole-N-CH₂-C(=O)-morpholine] |
| 189 | [structure: Chiral; indole-N-CH₂-C(=O)-NH-CH₂-C(=O)-O-CH₃] |

TABLE 68

| Ex | Structure |
|---|---|
| 190 | 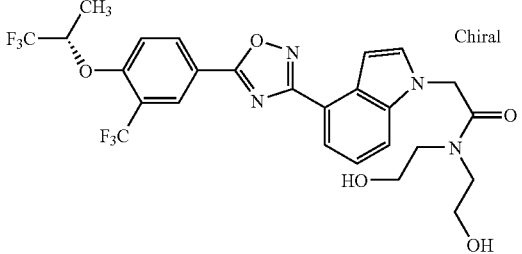 |
| 191 | 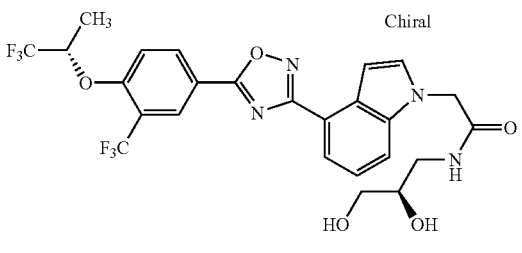 |
| 192 | 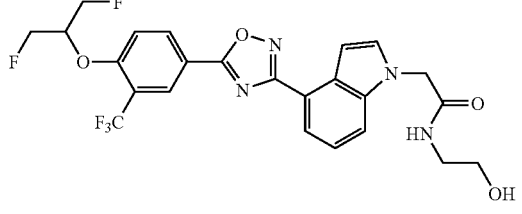 |
| 193 | 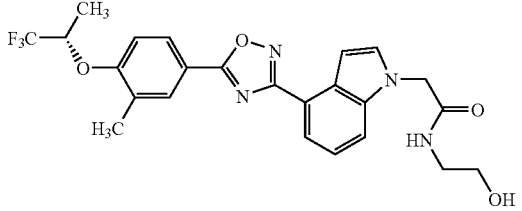 |
| 194 | 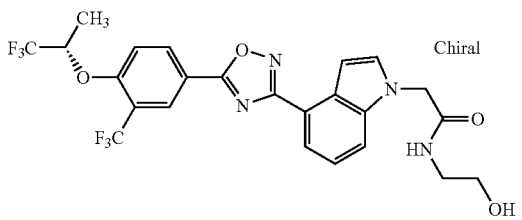 |
| 195 | 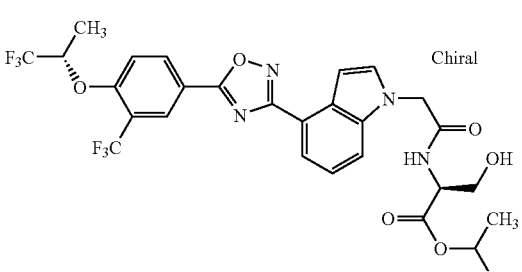 |

TABLE 68-continued

| Ex | Structure |
|---|---|
| 196 | 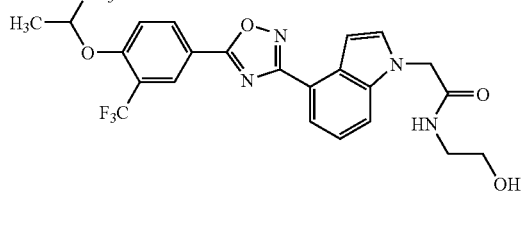 |
| 197 | 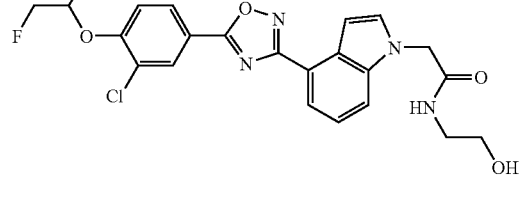 |
| 198 | 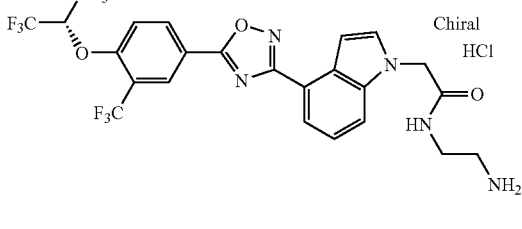 |
| 199 | 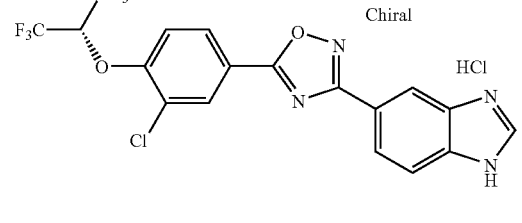 |
| 200 | 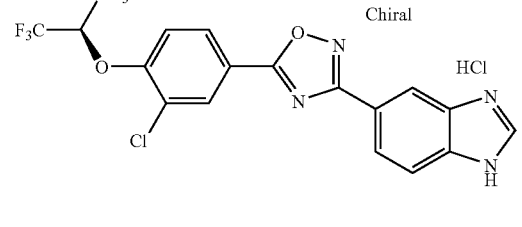 |
| 201 | 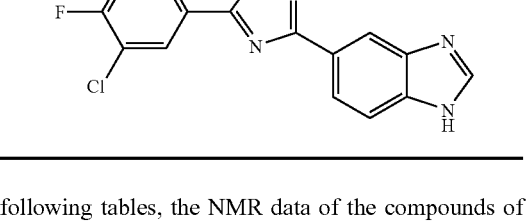 |

In following tables, the NMR data of the compounds of Examples are shown. Tetramethylsilane is used as an internal standard, and unless otherwise specifically mentioned, δ (ppm) of the signals in $^1$H-NMR using DMSO-$d_6$ as a measurement solvent is shown. Ref-Ex represents Example No. (Ex), which can be referred to for the preparation.

TABLE 69

| Ex | Data | MS | Ref-Ex |
|---|---|---|---|
| 1 | 1.52(3H, d), 2.65(3H, s), 5.73(1H, m), 7.60(1H, m), 7.62(1H, d), 7.82(1H, d), 8.11(1H, s), 8.40(1H, d), 8.49(1H, dd), 9.39 (1H, s) | 457 | |
| 2 | 1.53(3H, d), 2.83(3H, s), 3.42(2H, br), 5.75(1H, m), 7.82(1H, d), 7.95(1H, d), 8.21(1H, dd), 8.38-8.43(2H, m), 8.52(1H, dd) | 457 | |
| 3 | 1.72(6H, s), 4.92(2H, s), 7.08(1H, dd), 7.29(1H, brs), 7.35(1H, dd), 7.56(1H, d), 7.63(1H, brs), 7.64(1H, dm), 7.83(1H, d), 7.97(1H, dd), 8.41-8.46(2H, m) | 535 | |
| 4 | 0.37-0.44(2H, m), 0.58-0.64(2H, m), 1.23-1.35(1H, m), 4.17 (2H, d), 7.54(1H, d), 7.92(1H, d), 8.14(1H, dd), 8.35(1H, d), 8.41-8.47(2H, m), 9.07(1H, s) | 401 | |
| 5 | 1.36(6H, d), 4.91(2H, s), 4.95-5.03(1H, m), 7.08(1H, dm) 7.28(1H, brs), 7.34(1H, dd), 7.55(1H, d), 7.58-7.65(3H, m), 7.96(1H, dm), 8.36(1H, d), 8.45(1H, dd) | 467 | |
| 6 | 4.64-4.93(4H, m), 4.91(2H, s), 5.20-5.38(1H, m), 7.09(1H, d), 7.28(1H, bs), 7.34(1H, dd), 7.55(1H, d), 7.57-7.64(3H, m), 7.95(1H, d), 8.18(1H, dd), 8.28(1H, d) | 469 | |
| 7 | 1.50(3H, d), 2.30(3H, s), 4.91(2H, s), 5.42-5.52(1H, m), 7.09 (1H, dd), 7.29(1H, brs), 7.34(1H, dd), 7.45(1H, d), 7.54(1H, d), 7.60-7.65(2H, m), 7.95(1H, dd), 8.06-8.12(2H, m) | 467 | |
| 8 | 1.46(6H, d), 4.70-4.76(1H, m), 4.90(2H, s), 5.27(1H, bs), 5.36(1H, bs), 7.08(1H, d), 7.28(1H, d), 7.41-7.45(3H, m), 8.10-8.13(2H, m), 8.30(1H, d) | 433 | |
| 9 | 1.26(6H, d, J = 6.3 Hz), 3.88-3.98(1H, m), 5.56(1H, d, J = 7.9 Hz), 7.08(1H, brs), 7.13(1H, d, J = 9.6 Hz), 7.29(1H, t, J = 7.8 Hz), 7.56(1H, t, J = 2.7 Hz), 7.66(1H, d, J = 8.1 Hz), 7.91(1H, d, J = 7.6 Hz), 8.18-8.21(2H, m), 11.51(1H, brs) | 409, 387 | |
| 10 | 1.25(6H, d), 4.39-4.47(1H, m), 4.90(2H, s), 7.07-7.12(2H, m), 7.28(1H, br), 7.33(1H, dd), 7.53(1H, d), 7.61-7.63(2H, m), 7.93(1H, d), 8.26(1H, d), 8.84(1H, d) | 433 | |
| 11/1 | (CDCl$_3$)1.62(3H, d), 3.92(3H, s), 4.91(1H, m), 7.21(1H, d), 7.52(1H, d), 7.98(1H, d), 8.16(1H, dd), 8.40(1H, dd), 8.52 (1H, d), 8.64(1H, s) | 457 | |
| 11/2 | (CDCl$_3$)1.63(3H, d), 3.99(3H, s), 4.93(1H, m), 7.23(1H, dd), 7.93(1H, d), 8.06(1H, d), 8.16(1H, d), 8.28(1H, d), 8.41(1H, d), 8.54(1H, d) | Not found | |

TABLE 70

| Ex | Data | MS | Ref-Ex |
|---|---|---|---|
| 12 | 1.53(3H, d), 4.92(2H, s), 5.65-5.79(1H, m), 7.09(1H, d), 7.28 (1H, bs), 7.35(1H, dd), 7.55(1H, d), 7.62(1H, bs), 7.64(1H, d), 7.81(1H, d), 7.97(1H, dd), 8.42(1H, d), 8.52(1H, dd) [α]$^D_{23}$ = +11.20(c = 0.0025 CH$_3$OH) | 521 | |
| 13 | 1.52(3H, d), 2.36(2H, t), 3.27(2H, t), 3.37(2H, t), 3.46(2H, t), 5.64-5.78(1H, m), 6.71(1H, d), 6.86(1H, bs), 7.21(1H, dd), 7.33(1H, d), 7.41(1H, bs), 7.79(1H, d), 8.35(1H, d), 8.46(1H, dd) | 515 | |
| 14 | 1.52(3H, d), 2.09(3H, s), 3.77(2H, s), 5.65-5.78(1H, m), 7.23 (1H, dd), 7.42(1H, d), 7.45(1H, d), 7.62(1H, d), 7.81(1H, d), 8.40(1H, d), 8.51(1H, dd), 11.32(1H, s) | 485 | |
| 15 | 1.52(3H, d), 2.20(3H, s), 3.50(2H, t), 4.21(2H, t), 5.68-5.77 (1H, m), 7.40(1H, t), 7.78(1H, d), 7.80(1H, d), 8.29(1H, d), 8.37 (1H, d), 8.48(1H, dd) | 486 | |
| 16 | (CDCl$_3$)1.63(3H, d), 3.17(3H, s), 4.89-4.94(1H, m), 7.23(1H, d), 7.54(1H, dd), 7.58(1H, d), 7.63(1H, d), 8.13(1H, d), 8.23(1H, d), 8.41(1H, dd), 8.53(1H, d) | 542 | |
| 17 | 1.53(3H, d), 4.05(3H, s), 5.70-5.78(1H, m), 7.38(1H, d), 7.58 (1H, dd), 7.81(1H, d), 7.95(1H, d), 8.12(1H, d), 8.39(1H, d), 8.41(1H, s), 8.53(1H, dd) | Not found | |
| 18 | 1.52(3H, d), 2.81(2H, t), 3.27(2H, t), 3.49(2H, br), 5.74(1H, m), 7.01(1H, s), 7.56(1H, s), 7.82(1H, d), 7.92(1H, d), 8.17(1H, d), 8.39(2H, d), 8.51(1H, dd) | 514 | |
| 19 | 1.53(3H, d), 4.61(2H, d), 5.14(2H, s), 5.67-5.78(1H, m), 7.11(1H, d), 7.36(1H, dd), 7.61(1H, d), 7.65-7.76(3H, m), 7.82 (1H, d), 7.97(1H, dd), 8.27(1H, dd), 8.41(1H, d), 8.52(1H, dd), 8.73(1H, d), 9.04(1H, t) | 590 | |
| 20 | 1.53(3H, d), 3.05(3H, s), 4.97(2H, s), 5.66-5.78(1H, m), 7.08 (1H, d), 7.33(1H, d), 7.55(1H, d), 7.65(1H, d), 7.81(1H, d), 7.96(1H, d), 8.42(1H, d), 8.53(1H, dd), 12.31(1H, bs) | 599 | |
| 21 | 1.52(3H, d), 5.65-5.78(1H, m), 7.43(1H, dd), 7.63(1H, d), 7.78(1H, d), 7.81(1H, d), 8.34(1H, d), 8.38(1H, s), 8.47(1H, dd), 10.06(1H, s), 12.57(1H, bs) | 470 | |

TABLE 70-continued

| Ex | Data | MS | Ref-Ex |
|---|---|---|---|
| 22 | 1.50(3H, d), 5.55(1H, m), 7.64(1H, d), 7.98(1H, d), 8.20(1H, dd), 8.35(1H, dd), 8.46-8.50(2H, m), 9.29(1H, s), 13.31(1H, brs) | 419 | |

TABLE 71

| Ex | Data | MS | Ref-Ex |
|---|---|---|---|
| 23 | 1.53(3H, d), 3.14(3H, s), 3.60(2H, t), 3.83(2H, d), 5.74(1H, m), 7.82(1H, d), 7.93(1H, d), 8.16(1H, d), 8.38-8.44(2H, m), 8.52(1H, dd) | 549 | |
| 24 | 1.52(3H, d), 1.84-1.89(1H, m), 2.12-2.16(1H, m), 3.20-3.60(6H, m), 5.72-5.76(1H, m), 7.82(1H, d), 7.95(1H, d), 8.21(1H, dd), 8.40(2H, s), 8.52(1H, dd) | 531 | |
| 25 | 1.52(3H, d), 2.61(2H, t), 4.49(2H, t), 5.68-5.78(1H, m), 6.91(1H, bs), 7.06(1H, d), 7.36(1H, dd), 7.37(1H, bs), 7.55(1H, d), 7.78-7.83(2H, m), 7.96(1H, d), 8.41(1H, d), 8.52(1H, dd) | 535 | |
| 26 | 1.52(3H, d), 3.30(2H, t), 3.53(2H, t), 5.71(1H, m), 5.83(1H, brs), 6.69(1H, d), 7.12(1H, t), 7.29(1H, d), 7.79(1H, d), 8.35(1H, d), 8.47(1H, dd) | 444 | |
| 27 | 1.49(3H, d), 4.57(1H, d), 4.62(1H, d), 5.50(1H, m), 7.47(1H, d), 7.98(1H, d), 8.13(1H, dd), 8.20(1H, dd), 8.31(1H, m), 8.47(1H, m), 9.29(1H, s) | 405 | |
| 28 | 1.52(3H, d), 3.19(3H, s), 5.71(1H, m), 7.47(1H, d), 7.61(1H, d), 7.66(1H, d), 7.75(1H, s), 7.79(1H, s), 8.37(1H, d), 8.50(1H, dd) | 491 | |
| 29 | 1.52(3H, d), 5.69-5.82(1H, m), 7.49(1H, d), 7.56(1H, dd), 7.83(1H, d), 7.92(1H, d), 8.00(1H, d), 8.38(1H, d), 8.53(1H, dd) | 477 | |
| 30 | 1.53(3H, d), 3.76(2H, t), 4.32(2H, t), 4.93(1H, s), 5.65-5.76(1H, m), 7.07(1H, d), 7.34(1H, t), 7.59(1H, d), 7.79(1H, d), 7.81(1H, d), 7.96(1H, dd), 8.42(1H, s), 8.52(1H, dd) | 508 | |
| 31 | 1.53(3H, d), 3.02-3.30(4H, m), 3.63-3.90(4H, m), 5.37(2H, s), 5.68-5.80(1H, m), 7.11(1H, dd), 7.33(1H, d), 7.47(1H, d), 7.70(1H, d), 7.82(1H, d), 7.96(1H, d), 8.42(1H, d), 8.52(1H, dd), 9.26(1H, bs) | 568 | |
| 32 | 1.52(3H, d), 5.73(1H, m), 7.13(1H, t), 7.72(1H, d), 7.81(1H, d), 8.11(1H, dd), 8.14(1H, d), 8.40(1H, d), 8.51(1H, dd), 8.82(1H, dd) | 443 | 1 |
| 33 | 1.53(3H, d), 5.75(1H, m), 7.84(1H, d), 8.10(1H, d), 8.22(1H, d), 8.38(1H, dd), 8.41(1H, d), 8.50(1H, d), 8.51(1H, dd), 9.76(1H, s) | 443 | 1 |
| 34 | 1.52(3H, d), 3.03(3H, s), 5.73(1H, m), 7.68(1H, d), 7.77(1H, d), 7.79(1H, s), 7.82(1H, s), 8.09(1H, s), 8.38(1H, d), 8.51(1H, dd) | 457 | 1 |

TABLE 72

| Ex | Data | MS | Ref-Ex |
|---|---|---|---|
| 35 | 1.52(3H, d), 2.55(3H, s), 5.74(1H, m), 7.83(1H, d), 7.98(1H, dd), 8.24(1H, s), 8.42(1H, d), 8.46(1H, s), 8.54(1H, dd), 9.00(1H, d) | 457 | 1 |
| 36 | 2.81(3H, d), 2.37(3H, s), 2.47(3H, s), 5.73(1H, m), 7.47(1H, dd), 7.80(1H, d), 8.15(1H, s), 8.37(1H, d), 8.38(1H, d), 8.50(1H, dd) | 470 | 1 |
| 37 | 1.53(3H, d), 2.92(3H, s), 3.46(2H, br), 5.74(1H, m), 7.80(1H, d), 7.82(1H, d), 8.14(1H, d), 8.38-8.40(1H, m), 8.51(1H, dd), 9.37(1H, br) | 457 | 1 |
| 38 | 7.78(1H, d), 7.85(1H, t), 7.96(1H, dd), 8.34(1H, d), 8.38(1H, s), 8.50(1H, d), 8.56-8.62(1H, m) | 349 | 1 |
| 39 | 1.53(3H, d), 5.73(1H, m), 7.74(1H, d), 7.81(1H, d), 8.06(1H, dd), 8.28(1H, d), 8.39(1H, d), 8.49(1H, dd), 8.61(1H, m), 13.42(1H, brs) | 443 | 1 |
| 40 | 1.57(3H, d), 2.27(2H, m), 3.00(2H, t), 4.22(2H, t), 4.85(1H, m), 7.02-7.19(4H, m), 8.48(1H, dd), 8.62(1H, d) | 480 | 1 |
| 41 | 1.53(3H, d), 5.75(1H, m), 7.84(1H, d), 8.00(1H, dd), 8.26(1H, dd), 8.42(1H, d), 8.48(1H, d), 8.54(1H, dd), 8.56(1H, m), 9.05(1H, dd) | 443 | 2 |
| 42 | 1.22(3H, t), 1.52(3H, d), 3.87(2H, s), 4.13(2H, q), 5.74(1H, m), 7.50(1H, dd), 7.82(1H, d), 8.06(1H, s), 8.21(1H, s), 8.40(1H, d), 8.52(1H, dd), 8.72(1H, d) | 529 | 2 |
| 43 | 1.53(3H, d), 2.70(3H, s), 5.75(1H, m), 7.85(1H, d), 8.07(1H, d), 8.14(1H, d), 8.43(1H, dd), 8.45(1H, d), 8.55(1H, dd), 9.27(1H, d) | 457 | 2 |
| 44 | 1.53(3H, d), 2.72(3H, s), 3.49(1H, brs), 5.76(1H, m), 7.74(1H, d), 7.84(1H, d), 8.23(1H, brs), 8.25(1H, brs), 8.46(1H, s), 8.57(1H, dd), 8.94(1H, d) | 457 | 2 |

TABLE 72-continued

| Ex | Data | MS | Ref-Ex |
|---|---|---|---|
| 45 | 1.53(3H, d), 2.64(3H, s), 3.48(1H, brs), 5.76(1H, m), 7.84(1H, d), 8.04(1H, dd), 8.15(1H, s), 8.42(1H, d), 8.55(1H, dd), 8.60(1H, d), 8.92(1H, d) | 457 | 2 |
| 46 | 1.53(3H, d), 1.91(3H, s), 2.64(3H, s), 5.75(1H, m), 7.84(1H, d), 8.06(1H, d), 8.38(1H, dd), 8.45(1H, d), 8.54(1H, d), 9.20(1H, s) | 470 | 2 |
| 47 | 1.21(3H, t), 1.53(3H, d), 3.84(2H, s), 4.12(2H, q), 5.73(1H, m), 7.68(1H, d), 7.76-7.85(2H, m), 8.09(1H, s), 8.40(1H, m), 8.49(1H, dd), 9.46(1H, s) | 529 | 2 |
| 48 | 1.53(3H, d), 3.62(2H, brs), 5.74(1H, m), 7.82(1H, d), 8.02(1H, d), 8.23(1H, dd), 8.40(1H, d), 8.49-8.54(2H, m), 9.45(1H, s) | 443 | 2 |

TABLE 73

| Ex | Data | MS | Ref-Ex |
|---|---|---|---|
| 49 | 1.52(3H, d), 2.76(3H, s), 3.40(2H, brs), 5.74(1H, m), 7.82(1H, d), 7.86(1H, d), 8.40(1H, d), 8.45(1H, s), 8.52(1H, dd), 9.37(1H, s) | 457 | 2 |
| 50 | 1.43(3H, t), 1.52(3H, d), 3.90(2H, br), 4.58(2H, q), 5.73(1H, m), 7.53(1H, d), 7.81(1H, d), 7.89(1H, dd), 8.03(1H, brs), 8.38(1H, d), 8.49(1H, dd) | 487 | 2 |
| 51 | 1.52(3H, d), 3.37(3H, br), 5.73(1H, m), 7.56(1H, d), 7.82(1H, d), 7.99(1H, d), 8.07(1H, m), 8.37(1H, d), 8.49(1H, dd), 8.78(2H, brs) | 458 | 2 |
| 52 | 1.52(3H, d), 5.72(1H, m), 7.10(1H, d), 7.60(1H, d), 7.73(1H, dd), 7.79(1H, d), 8.35(1H, d), 8.47(1H, dd), 10.89(2H, br) | 481 | 2 |
| 53 | 1.53(3H, d), 5.60(1H, m), 7.69(1H, d), 8.01(1H, d), 8.23-8.17(2H, m), 8.29(1H, d), 8.48(1H, m), 9.39(1H, s) | 409 | 2 |
| 54 | 1.56(3H, d), 5.74(1H, m), 7.80(1H, d), 8.03(1H, d), 8.22(1H, dd), 8.49(1H, m), 8.53(1H, dd), 8.64(1H, d), 9.46(1H, s) | 400 | 2 |
| 55 | 1.58(3H, d), 5.71(1H, m), 7.85-7.71(2H, m), 7.96(1H, dd), 8.27-8.42(2H, m), 8.47-8-51(2H, m), 10.39(1H, s), 12.78(1H, d) | 403 | 2 |
| 56 | 1.15(6H, s), 2.81(2H, s), 2.83(2H, s), 7.48(1H, d), 7.98-8.04(3H, m), 8.21(1H, d), 8.48(1H, m), 9.43(1H, s) | 331 | 2 |
| 57 | 1.52(3H, d), 2.74(3H, s), 5.67-5.82(1H, m), 7.81(1H, d), 8.08(1H, d), 8.26(1H, d), 8.38(1H, d), 8.50(1H, dd) | 491 | 2 |
| 58 | 1.52(3H, d), 3.60(2H, s), 5.73(1H, m), 7.43(1H, d), 7.50(1H, m), 7.72(1H, dd), 7.80(1H, d), 8.36(1H, m), 8.48(1H, dd), 10.59(1H, s) | 480 | 2 |
| 59 | 1.53(3H, d), 5.73-5.83(1H, m), 7.87(1H, d), 8.05(1H, dd), 8.26(1H, d), 8.39(1H, d), 8.40(1H, d), 8.47(1H, d), 8.59(1H, dd), 9.00(1H, d) | 443 | 2 |
| 60 | 1.53(3H, d), 5.75(1H, m), 7.05(1H, dd), 7.76(1H, dd), 7.83(1H, d), 7.86(1H, d), 8.42(1H, d), 8.47(1H, d), 8.54(1H, dd), 12.20(1H, br) | 443 | 2 |
| 61 | 1.54(3H, d), 5.70-5.82(1H, m), 7.74(1H, dd), 7.86(1H, d), 8.11(1H, d), 8.29(1H, d), 8.56(1H, d), 8.66(1H, dd), 9.53(1H, s) | 443 | 2 |
| 62 | 1.52(3H, d), 5.67-5.77(1H, m), 6.65(1H, dd), 7.64(1H, d), 7.82(1H, d), 8.40(1H, d), 8.50(1H, dd), 8.68(1H, d), 8.95(1H, d), 12.10(1H, s) | 443 | 2 |
| 63 | 1.53(3H, d), 5.54(1H, m), 7.70(1H, t), 8.02(1H, d), 8.08(1H, dm), 8.11(1H, dd), 8.21(1H, dd), 8.48(1H, m), 9.45(1H, s) | 393 | 2 |

TABLE 74

| Ex | Data | MS | Ref-Ex |
|---|---|---|---|
| 64 | 1.53(3H, d), 5.60(1H, m), 7.65(1H, d), 7.99(1H, d), 8.20(1H, dd), 8.24(1H, dd), 8.42(1H, m), 8.48(1H, m), 9.35(1H, s) | 453, 455 | 2 |
| 65 | 1.53(3H, d), 5.74(1H, m), 7.82(1H, t), 7.83(1H, dd), 7.98(1H, d), 8.22(1H, s), 8.31(1H, s), 8.40(1H, d), 8.52(1H, dd), 13.42(1H, s) | 443 | 2 |
| 66 | 1.53(3H, d), 5.73(1H, m), 7.81(1H, d), 8.10(1H, d), 8.15(1H, dd), 8.39(1H, d), 8.51(1H, dd), 8.66(1H, s), 16.07(1H, brs) | 466 | 2 |
| 67 | 1.53(3H, d), 5.72(1H, m), 7.10(1H, d), 7.31(1H, t), 7.59(1H, d), 7.68(1H, d), 7.80(1H, d), 7.95(1H, d), 8.41(1H, d), 8.51(1H, dd), 11.5(1H, brs) | 464 | 2 |
| 68 | 1.50(3H, d), 2.29(3H, s), 5.48(1H, m), 7.45(1H, d), 8.09-8.01(3H, m), 8.24(1H, dd), 8.49(1H, m), 9.61(1H, s) | 389 | 2 |
| 69 | 1.48(3H, d), 3.96(3H, s), 5.35(1H, m), 7.45(1H, d), 7.76(1H, d), 7.83(1H, dd), 8.03(1H, d), 8.24(1H, dd), 8.50(1H, m), 9.53(1H, s) | 405 | 2 |

TABLE 74-continued

| Ex | Data | MS | Ref-Ex |
|---|---|---|---|
| 70 | 1.53(3H, d), 5.70(1H, m), 6.62(1H, s), 7.48(1H, t), 7.57(1H, d), 7.80(1H, d), 7.83(1H, dd), 8.36-8.39(2H, m), 8.49(1H, dd), 11.47(1H, s) | 464 | 2 |
| 71 | (CDCl₃)1.65(3H, d), 3.39(3H, s), 4.92-5.02(1H, m), 7.28(1H, d), 7.72(0.25H, t), 7.78(0.25H, t), 7.98(0.75H, t), 8.12(0.75H, t), 8.44(1H, d), 8.46(1H, d), 8.52(1H, s), 8.91(1H, d), 9.79(1H, s) | 468 | 2 |
| 72 | 1.17(3H, t), 1.52(3H, d), 2.91(2H, t), 3.09-3.18(2H, m), 4.07(2H, q), 5.72(1H, m), 7.59-7.72(1H, m), 7.80(1H, d), 7.90(1H, dd), 8.13-8.28(1H, m), 8.38(1H, d), 8.50(1H, d), 12.58(1H, s) | 543 | 2 |
| 73 | 1.52(3H, d), 2.72(3H, s), 5.70-5.78(1H, m), 7.82(1H, d), 8.05(1H, s), 8.32(1H, s), 8.38(1H, d), 8.50(1H, dd), 9.61(1H, s) | 457 | 2 |
| 74 | 1.53(3H, d), 5.68-5.80(1H, m), 6.60(1H, d), 7.72(1H, d), 7.81(1H, d), 7.93(1H, d), 8.18(1H, d), 8.40(1H, d), 8.51(1H, dd), 12.10(1H, s) | 465 | 2 |
| 75 | 1.51(3H, d), 5.73(1H, m), 7.82(1H, d), 8.08(1H, d), 8.24(1H, dd), 8.42(1H, d), 8.52(1H, dd), 8.68(1H, s), 9.64(1H, m) | 442 | 2 |
| 76 | 1.53(3H, d), 5.51(2H, brs), 5.72(1H, m), 7.62(1H, dd), 7.80(1H, d), 7.89(1H, d), 8.01(1H, s), 8.39(1H, d), 8.50(1H, dd), 11.73(1H, brs) | 480 | 2 |
| 77 | 1.53(3H, d), 5.67-5.76(1H, m), 7.82(1H, d), 8.41(1H, d), 8.52(1H, dd), 8.69(1H, d), 8.85(1H, s), 9.14(1H, d) | 466 | 2 |

TABLE 75

| Ex | Data | MS | Ref-Ex |
|---|---|---|---|
| 78 | 1.51(3H, d), 5.69(1H, m), 6.55(1H, d), 7.56(1H, d), 7.72-7.75(2H, m), 7.80(1H, d), 8.20(1H, s), 8.38(1H, d), 8.49(1H, dd), 11.47(1H, s) | 464 | 2 |
| 79 | 1.53(3H, d), 5.73(1H, m), 7.81(1H, d), 8.24(1H, d), 8.28(1H, d), 8.39(1H, d), 8.49(1H, dd), 8.98(1H, m), 9.57(1H, s) | 460 | 2 |
| 80 | 1.53(3H, d), 5.70-5.79(1H, m), 7.84(1H, d), 7.91(1H, dd), 8.39(1H, d), 8.41(1H, d), 8.51(1H, dd), 8.55(1H, dd), 8.99(1H, d), 9.01(1H, s), 9.20(1H, dd) | 454 | 2 |
| 81 | 1.64-1.79(4H, m), 1.84-1.96(2H, m), 2.04-2.14(2H, m), 4.92(2H, s), 7.09(1H, d), 7.28(1H, brs), 7.35(1H, dd), 7.56(1H, d), 7.62(1H, brs), 7.65(1H, d), 7.94-7.99(2H, m), 8.40(1H, d), 8.45(1H, dd) | 477 | 2 |
| 82 | 1.50(3H, d, J = 6.3 Hz), 2.30(3H, s), 5.43-5.49(1H, m), 7.08-7.09(1H, m), 7.27-7.31(1H, m), 7.43-7.45(1H, m), 7.56-7.57(1H, m), 7.65-7.67(1H, m), 7.91-7.93(1H, m), 8.06-8.09(2H, m), 11.52(1H, s) | 388 | 2 |
| 83 | 1.51(3H, d, J = 6.3 Hz), 5.55-5.61(1H, m), 7.08-7.09(1H, m), 7.28-7.31(1H, m), 7.57-7.68(3H, m), 7.92-7.94(1H, m), 8.22-8.25(1H, m), 8.42-8.43(1H, m), 11.54(1H, s) | 453 | 2 |
| 84 | 1.52(3H, d, J = 4.7 Hz), 5.68-5.75(1H, m), 7.21-7.28(2H, m), 7.52-7.54(1H, m), 7.79-7.81(1H, m), 8.08-8.49(4H, m), 11.93(1H, s) | 442 | 2 |
| 85 | 1.40(3H, t, J = 6.8 Hz), 2.28(3H, s), 4.18(2H, q, J = 6.8 Hz), 4.09(2H, s), 7.08-7.35(4H, m), 7.53-7.63(3H, m), 7.93-8.07(3H, m) | 399 | 2 |
| 86 | 1.34(6H, m, J = 2.1 Hz), 2.25(3H, s), 4.75-4.81(1H, m), 4.91(2H, s), 7.092-7.093(1H, m), 7.21-7.35(3H, m), 7.53-7.63(3H, m), 7.93-8.05(3H, m) | 391 | 2 |
| 87 | 1.52(3H, d), 5.60-5.72(1H, m), 7.19(1H, t), 7.71(1H, d), 8.03(1H, dd), 8.24(1H, dd), 8.33-8.36(1H, m), 8.41(1H, dd), 8.50-8.52(1H, m), 9.49(1H, s) | 425 | 2 |
| 88 | 1.52(3H, d), 3.79(2H, s), 5.67-5.78(1H, m), 7.05(1H, d), 7.42(1H, t), 7.72(1H, dm), 7.80(1H, d), 8.37-8.40(1H, m), 8.50(1H, dd), 10.65(1H, s) | 456 | 2 |
| 89 | 1.52(3H, d), 5.67-5.78(1H, m), 7.46(1H, d), 7.69(1H, d), 7.80(1H, d), 7.84(1H, dd), 8.36(1H, d), 8.48(1H, dd) | 482 | 2 |

TABLE 76

| Ex | Data | MS | Ref-Ex |
|---|---|---|---|
| 90 | 1.52(3H, d), 5.68-5.78(1H, m), 7.31-7.38(2H, m), 7.79(1H, dd), 7.81(1H, d), 8.39(1H, d), 8.51(1H, dd), 12.00(1H, brs) | 482 | 2 |
| 91 | 0.94(6H, d), 1.96-2.06(1H, m), 2.76(2H, d), 4.92(2H, s), 7.10(1H, dd), 7.29(1H, brs), 7.35(1H, dd), 7.56(1H, d), 7.63(1H, brs), 7.65(1H, dm), 7.81(1H, d), 7.97(1H, dd), 8.41-8.46(2H, m) | 465 | 2 |

TABLE 76-continued

| Ex | Data | MS | Ref-Ex |
|---|---|---|---|
| 92 | 1.53(3H, d), 5.64-5.79(1H, m), 7.09(1H, d), 7.30(1H, dd), 7.58(1H, d), 7.68(1H, d), 7.81(1H, d), 7.94(1H, d), 8.41(1H, d), 8.52(1H, dd), 11.53(1H, bs) | 442 | 2 |
| 93 | 1.53(3H, d), 5.57-5.63(1H, m), 7.04(1H, dd), 7.65(1H, d), 7.73(1H, dd), 7.83(1H, d), 8.26(1H, dd), 8.45-8.46(2H, m), 12.14(1H, s) | 453 | 2 |
| 94 | 1.53(3H, d), 5.57-5.63(1H, m), 7.03(1H, dd), 7.70(1H, d), 7.74(1H, dd), 7.83(1H, d), 8.23(1H, d), 8.32(1H, d), 8.46(1H, d), 12.12(1H, s) | 409 | 2 |
| 95 | 1.50(3H, d), 2.30(3H, s), 5.45-5.51(1H, m), 7.03(1H, dd), 7.46(1H, d), 7.73(1H, dd), 7.82(1H, d), 8.09-8.11(2H, dd), 8.45(1H, d), 12.12(1H, s) | 389 | 2 |
| 96 | 1.56(3H, d), 5.71-5.78(1H, m), 7.06(1H, dd), 7.75(1H, dd), 7.80(1H, d), 7.83(1H, d), 8.47(1H, d), 8.56(1H, dd), 8.69(1H, d), 12.16(1H, s) | 398 | 2 |
| 97 | 1.53(3H, d), 5.71-5.77(1H, m), 7.04(1H, dd), 7.75(1H, dd), 7.83(1H, d), 7.86(1H, d), 8.43(1H, d), 8.47(1H, d), 8.54(1H, dd), 12.19(1H, s) | Not found | 2 |
| 98 | 1.52(3H, d), 2.58(2H, dd), 2.97(2H, dd), 5.00(1H, d), 5.11(1H, d), 5.67-5.78(1H, m), 5.83-5.98(1H, m), 7.61(1H, d), 7.70(1H, d), 7.80(1H, d), 7.90(1H, t), 8.19(1H, d), 8.38(1H, s), 8.50(1H, dd), 12.55(1H, d) | 497 | 2 |
| 99 | 1.57(3H, d), 5.58(1H, m), 7.08(1H, m), 7.29(1H, t), 7.58(1H, m), 7.65-7.72(2H, m), 7.93(1H, d), 8.20(1H, dd), 8.29(1H, d). | 408 | 2 |
| 100 | 1.56(3H, d), 5.72(1H, m), 7.10(1H, m), 7.30(1H, t), 7.58(1H, m), 7.67(1H, d), 7.78(1H, d), 7.93(1H, d), 8.53(1H, dd), 8.64(1H, d). | 421 | 2 |
| 101 | 0.90(6H, d), 2.12(1H, m), 3.82(2H, d), 6.89(1H, dd), 7.07(1H, m), 7.18(1H, d), 7.31(1H, dd), 7.59(1H, dd), 7.67-7.70(1H, m), 7.91(1H, dd), 7.96(1H, d), 11.56(1H, s) | 335 | 2 |

TABLE 77

| Ex | Data | MS | Ref-Ex |
|---|---|---|---|
| 102 | 0.90(6H, d), 2.09-2.15(1H, m), 3.82(2H, d), 4.91(2H, s), 6.90(1H, dd), 7.08(1H, d), 7.19(1H, d), 7.29(1H, br), 7.35(1H, dd), 7.56(1H, d), 7.62(1H, br), 7.65(1H, d), 7.95(2H, dd) | 414 | 2 |
| 103 | 4.82(1H, d), 5.08(2H, d), 5.22(1H, t), 7.64(1H, d), 7.99(1H, d), 8.21(1H, dd), 8.46-8.50(2H, m), 8.53(1H, dd), 9.33(1H, s) | 405 | 4 |
| 104 | 1.35(6H, d), 4.98(1H, m), 7.60(1H, d), 7.99(1H, d), 8.20(1H, dd), 8.34(1H, d), 8.43(1H, dd), 8.48(1H, d), 9.32(1H, s) | 389 | 4 |
| 105 | 1.70(1H, m), 1.87(1H, m), 2.04-2.16(2H, m), 2.45-2.59(2H, m), 5.03(1H, m), 7.40(1H, d), 7.94(1H, d), 8.16(1H, dd), 8.35(1H, d), 8.42(1H, d), 8.45(1H, d), 9.16(1H, s) | 401 | 4 |
| 106 | 4.87-4.92(2H, m), 5.34(1H, dd), 5.46(1H, dd), 6.02-6.12(1H, m), 7.57(1H, d), 7.99(1H, d), 8.21(1H, dd), 8.36(1H, d), 8.44-8.49(2H, m), 9.48(1H, s) | 387 | 4 |
| 107 | 5.16(2H, q), 7.69(1H, d), 8.01(1H, d), 8.23(1H, dd), 8.40(1H, d), 8.50(1H, d), 8.54(1H, dd), 9.49(1H, s) | 429 | 4 |
| 108 | 5.45(2H, s), 7.36-7.51(5H, m), 7.66(1H, d), 8.00(1H, d), 8.22(1H, dd), 8.37(1H, d), 8.47(1H, d), 8.49(1H, d), 9.42(1H, s) | 437 | 4 |
| 109 | 7.32(1H, d), 7.96(1H, d), 8.17(1H, dd), 8.27-8.33(2H, m), 8.45(1H, d), 11.90(1H, s) | 347 | 4 |
| 110 | 4.68(2H, dt), 6.64(1H, tt), 7.65(1H, d), 8.01(1H, d), 8.23(1H, dd), 8.38(1H, d), 8.47-8.52(2H, m), 9.45(1H, s) | 411 | 4 |
| 111 | 1.39(3H, d), 4.29(1H, q), 7.94(1H, d), 8.15(1H, dd), 8.43-8.47(3H, m), 8.51-8.55(1H, m), 8.58-8.62(1H, m), 9.09(1H, brs), 9.71(1H, s) | 418 | 4 |
| 112 | 7.32(1H, d), 7.61(1H, dd), 7.79(1H, ddd), 8.04(1H, d), 8.26(1H, dd), 8.47(1H, dd), 8.52(2H, brs), 8.58(1H, dd), 8.61(1H, d), 9.54(1H, s) | 424 | 4 |
| 113 | 0.96(3H, t), 1.32(3H, d), 1.67-1.76(2H, m), 4.75-4.85(1H, m), 7.59(1H, d), 7.99(1H, d), 8.21(1H, dd), 8.34(1H, d), 8.43(1H, d), 8.49(1H, m), 9.38(1H, s) | 403 | 4 |
| 114 | 1.81(3H, s), 4.80(2H, s), 5.04(1H, s), 5.13(1H, s), 7.56(1H, d), 7.97(1H, d), 8.19(1H, dd), 8.37(1H, d), 8.44-8.48(2H, m), 9.27(1H, s) | 401 | 4 |
| 115 | 1.46(3H, t), 5.23-5.26(1H, m), 5.33-5.40(2H, m), 5.95(1H, dq), 7.56(1H, d), 7.98(1H, d), 8.19(1H, dd), 8.35(1H, d), 8.42(1H, dd), 8.47(1H, s), 9.29(1H, s) | 401 | 4 |

TABLE 78

| Ex | Data | MS | Ref-Ex |
|---|---|---|---|
| 116 | 1.76(3H, s), 1.77(3H, s), 4.89(2H, d), 5.48-5.49(1H, m), 7.57 (1H, d), 8.01(1H, d), 8.22(1H, dd), 8.34(1H, d), 8.45(1H, dd), 8.45(1H, d), 9.44(1H, s) | 415 | 4 |
| 117 | 3.02-4.13(8H, m), 7.73(1H, d), 8.00(1H, d), 8.22(1H, dd), 8.39(1H, d), 8.44(1H, dd), 8.49(1H, m), 9.38(1H, s) | 414 | 4 |
| 118 | 1.00(3H, t), 1.35(3H, d), 1.59-1.78(2H, m), 3.72-3.85(1H, m), 7.96(1H, d), 8.02(1H, d), 8.23(1H, d), 8.36(1H, d), 8.38(1H, s), 8.51(1H, s), 9.48(1H, s) | 419 | 4 |
| 119 | 1.53(3H, d), 5.70-5.80(1H, m), 7.83(1H, d), 8.03(1H, d), 8.25 (1H, dd), 8.40(1H, d), 8.49-8.54(2H, m), 9.50(1H, s). $[\alpha]^D_{25} = +10.2$(c = 0.20 MeOH) | 443 | 4 |
| 120 | 1.53(3H, d), 5.70-5.79(1H, m), 7.82(1H, d), 8.00(1H, d), 8.26 (1H, dd), 8.40(1H, d), 8.49-8.54(2H, m), 9.35(1H, s). $[\alpha]^D_{23} = -9.61$(c = 0.21 MeOH) | 443 | 4 |
| 121 | 7.18(1H, d), 7.23-7.27(2H, m), 7.35(1H, t), 7.51-7.58(2H, m), 7.98(1H, d), 8.18(1H, dd), 8.42-8.53(3H, m), 9.26(1H, s) | 423 | 4 |
| 122 | 4.98(2H, t), 6.59(1H, tt), 7.71(1H, d), 8.00(1H, d), 8.21(1H, dd), 8.40(1H, d), 8.49(1H, d), 8.52(1H, d), 9.33(1H, s) | 461 | 4 |
| 123 | 4.65-4.95(4H, m), 5.30-5.52(1H, m), 7.75(1H, d), 8.02(1H, d), 8.24(1H, dd), 8.38(1H, d), 8.47(1H, dd), 8.51(1H, s), 9.48(1H, s) | 425 | 4 |
| 124 | 1.59(3H, d), 5.04(1H, d), 5.10(1H, d), 5.84(1H, q), 6.51(1H, dd), 7.23(1H, d), 8.00(1H, d), 8.21(1H, dd), 8.42-8.50(3H, m), 9.35(1H, s) | 413 | 5 |
| 125 | 1.06-1.96(10H, m), 4.77-4.85(1H, m), 7.07-7.10(1H, m), 7.30(1H, t, J = 7.7 Hz), 7.56-7.62(2H, m), 7.67(1H, d, J = 8.0 Hz), 7.93(1H, d, J = 7.4 Hz), 8.35(1H, d, J = 2.1 Hz), 8.42(1H, dd, J = 2.1, 8.8 Hz), 11.53(1H, brs) | 466, 450, 428 | 5 |
| 126 | 4.91(2H, s), 7.09(1H, dd), 7.19(1H, d), 7.22-7.27(2H, m), 7.28(1H, brs), 7.32-7.38(2H, m), 7.51-7.57(3H, m), 7.61(1H, brs), 7.64(1H, dm), 7.96(1H, dd), 8.45( | 501 | 5 |
| 127 | 1.53(3H, d), 4.92(2H, s), 5.65-5.79(1H, m), 7.09(1H, d), 7.28 (1H, bs), 7.35(1H, dd), 7.55(1H, d), 7.62(1H, bs), 7.64(1H, d), 7.81(1H, d), 7.97(1H, d), 8.42(1H, dd), 8.52(1H, dd) | 521 | 5 |
| 128 | 4.91(2H, s), 5.08(2H, q), 7.09(1H, dd), 7.28(1H, bs), 7.35(1H, dd), 7.55(1H, d), 7.57(1H, d), 7.61(1H, bs), 7.64(1H, d), 7.95 (1H, d), 8.24(1H, dd), 8.31(1H, d) | 473 | 5 |

TABLE 79

| Ex | Data | MS | Ref-Ex |
|---|---|---|---|
| 129 | 1.53(3H, d), 5.71-5.77(1H, m), 7.03(1H, dd), 7.74(1H, dd), 7.82-7.86(2H, m), 8.43(1H, d), 8.46(1H, d), 8.55(1H, dd), 12.15(1H, s) | Not found | 5 |
| 130 | 5.13-5.20(2H, dd), 7.04(1H, dd), 7.70(1H, d), 7.75(1H, dd), 7.85(1H, d), 8.43(1H, d), 8.46(1H, d), 8.57(1H, dd), 12.15(1H, s) | 429 | 5 |
| 131 | 4.69(2H, ddd), 6.33-6.62(1H, m), 7.04(1H, dd), 7.66(1H, d), 7.75(1H, dd), 7.85(1H, d), 8.41(1H, d), 8.46(1H, dd), 8.53(1H, dd), 12.14(1H, s) | 409 | 5 |
| 132 | 7.03(1H, dd), 7.20(1H, dd), 7.24-7.27(2H, m), 7.34-7.38(1H, m), 7.52-7.57(2H, m), 7.75(1H, dd), 7.84(1H, d), 8.45(1H, d), 8.47(1H, dd), 8.52(1H, d), 12.14(1H, s) | 421 | 5 |
| 133 | 4.92(2H, s), 5.28(2H, dd), 7.11(1H, d), 7.29(1H, br), 7.35(1H, dd), 7.55(1H, d), 7.63-7.68(3H, m), 7.96(1H, d), 8.56(1H, dd), 8.66(1H, d) | 440 | 5 |
| 134 | 1.64-2.16(6H, m), 4.91(2H, s), 5.26(1H, br), 5.90(1H, d), 6.04-6.08(1H, m), 7.08(1H, d), 7.28(1H, br), 7.34(1H, dd), 7.55(1H, d), 7.62-7.68(3H, m), 7.96(1H, d), 8.36(1H, d), 8.44(1H, dd) | 481 | 5 |
| 135 | 4.91(2H, s), 5.07(2H, q), 7.09(1H, dd), 7.28(1H, bs), 7.34(1H, dd), 7.52(1H, d), 7.55(1H, d), 7.62-7.65(2H, m), 7.96(1H, dd), 8.27(1H, dd), 8.44(1H, d) | 495 | 5 |
| 136 | 1.57(3H, d, J = 6.5 Hz), 6.01-6.10(1H, m), 7.09(1H, d, J = 2.7 Hz), 7.30(1H, t, J = 7.8 Hz), 7.58 (1H, brs), 7.68(1H, d, J = 8.1 Hz), 7.93(1H, d, J = 6.6 Hz), 8.71(1H, d, J = 2.0 Hz), 9.00(1H, d, J = 2.0 Hz), 11.55(1H, brs) | 411, 409 | 5 |
| 137 | 4.92(2H, s), 5.24(2H, q), 7.10(1H, dm), 7.29(1H, brs), 7.35(1H, dd), 7.55(1H, d), 7.62(1H, brs), 7.65(1H, dm), 7.96(1H, dm), 8.75(1H, d), 9.02(1H, d) | 474 | 6 |
| 138 | 4.82(2H, ddd), 4.92(2H, s), 6.50(1H, m), 7.10(1H, dd), 7.29 (1H, br), 7.35(1H, dd), 7.56(1H, d), 7.63-7.65(2H, m), 7.96 (1H, dd), 8.71(1H, d), 9.01(1H, d) | 456 | 5 |
| 139 | 5.15(2H, q, J = 8.6 Hz), 7.09(1H, brs), 7.30(1H, d, J = 7.7 Hz), 7.58(1H, brs), 7.66-7.69(2H, m), 7.94(1H, d, J = 6.7 Hz), 8.41 (1H, brs), 8.54(1H, d, J = 8.7 Hz), 11.54(1H, brs) | 450, 428, 426 | 6 |

TABLE 80

| Ex | Data | MS | Ref-Ex |
|---|---|---|---|
| 140 | 4.67(2H, dt, J = 3.4, 14.5 Hz), 6.47(1H, tt, J = 3.3, 54.0 Hz), 7.09 (1H, d, J = 2.8 Hz), 7.30(1H, t, J = 7.8 Hz), 7.58(1H, brs), 7.57-7.69(2H, m), 7.94(1H, d, J = 7.4 Hz), 8.39(1H, d, J = 2.0 Hz), 8.50(1H, dd, J = 2.0, 8.7 Hz), 11.54(1H, brs) | 432, 410 | 6 |
| 141 | 4.67-4.94(4H, m), 5.32-5.49(1H, m), 7.09(1H, brs), 7.30(1H, t, J = 7.7 Hz), 7.58(1H, brs), 7.68(1H, d, J = 8.2 Hz), 7.74(1H, d, J = 8.9 Hz), 7.94(1H, d, J = 7.3 Hz), 8.39(1H, s), 8.47(1H, d, J = 8.8 Hz), 11.54(1H, brs) | 446, 424 | 6 |
| 142 | 4.47-4.93(4H, m), 5.36-5.49(1H, m), 7.03(1H, dd), 7.74-7.77(2H, m), 7.85(1H, d), 8.40(1H, d), 8.46(1H, d), 8.50(1H, dd), 12.13(1H, s) | 423 | 6 |
| 143 | 4.72-4.84(2H, m), 4.85-4.96(2H, m), 4.92(2H, s), 5.75-5.97 (1H, m), 7.10(1H, d), 7.29(1H, bs), 7.35(1H, dd), 7.56(1H, d), 7.61-7.67(2H, m), 7.96(1H, d), 8.69(1H, d), 8.98(1H, d) | 470 | 7 |
| 144 | 1.94-2.00(4H, m), 3.45-3.54(4H, m), 7.17(1H, d), 7.94(1H, d), 8.15(2H, dd), 8.32(1H, d), 8.44(1H, brs), 9.18(1H, s) | 400 | 7 |
| 145 | 1.53(3H, d), 2.15(3H, s), 3.07(2H, t), 3.43(2H, t), 5.74(1H, m), 7.82(1H, d), 7.96(1H, d), 8.19(1H, d), 8.39-8.44(2H, m), 8.52 (1H, dd) | 517 | 7 |
| 146 | 2.32(3H, s), 4.91(2H, s), 4.96(2H, q), 7.09(1H, dd), 7.29(1H, brs), 7.32-7.37(2H, m), 7.54(1H, d), 7.60-7.65(2H, m), 7.95 (1H, dd), 8.09-8.13(2H, m) | 453 | 7 |
| 147 | 1.50(3H, d), 2.30(3H, s), 4.91(2H, s), 5.42-5.52(1H, m), 7.10 (1H, dd), 7.29(1H, brs), 7.34(1H, dd), 7.45(1H, d), 7.54(1H, d), 7.60-7.65(2H, m), 7.95(1H, dd), 8.06-8.11(2H, m) | 467 | 7 |
| 148 | 2.23-2.30(2H, m), 3.24(2H, t), 3.62-3.67(2H, m), 4.91(2H, s), 5.80-5.93(2H, m), 7.09(1H, dd), 7.29(1H, brs), 7.35(1H, dd), 7.55(1H, d), 7.60-7.66(2H, m), 7.69(1H, d), 7.96(1H, dd), 8.38-8.43(2H, m) | 490 | 7 |
| 149 | 1.51(3H, d), 2.30(3H, s), 5.38-5.52(1H, m), 7.09(1H, dd), 7.29 (1H, dd), 7.44(1H, d), 7.56(1H, d), 7.66(1H, d), 7.92(1H, d), 8.05-8.11(2H, m), 11.49(1H, bs) | 410 | 11 |
| 150 | 1.40(6H, d), 4.91(2H, s), 5.43-5.50(1H, m), 7.10(1H, m), 7.28 (1H, bs), 7.35(1H, dd), 7.55(1H, d), 7.61(1H, bs), 7.64(1H, d), 7.95(1H, d), 8.60(1H, d), 8.98(1H, d) | 434 | 8 |

TABLE 81

| Ex | Data | MS | Ref-Ex |
|---|---|---|---|
| 151 | 1.52(3H, d), 3.89(3H, s), 5.72(1H, m), 7.06(1H, d), 7.36(1H, dd), 7.56(1H, d), 7.74(1H, d), 7.80(1H, d), 7.97(1H, d), 8.40 (1H, d), 8.51(1H, dd) | 456 | 11 |
| 152 | 1.51(3H, d), 2.77(3H, s), 3.27(2H, t), 3.39(2H, t), 5.67-5.75 (1H, m), 6.70(1H, d), 7.23(1H, t), 7.35(1H, d), 7.79(1H, d), 8.35 (1H, d), 8.47(1H, dd) | 458 | 11 |
| 153 | 1.53(3H, d), 3.70(3H, s), 5.28(2H, s), 5.67-5.78(1H, m), 7.13 (1H, d), 7.35(1H, dd), 7.58(1H, d), 7.72(1H, d), 7.81(1H, d), 7.97(1H, d), 8.41(1H, d), 8.52(1H, dd) | 514 | 11 |
| 154 | 1.24(3H, t), 1.53(3H, d), 4.20(2H, q), 5.35(2H, s), 5.73(1H, m), 7.76-7.83(2H, m), 8.02(1H, dd), 8.37(1H, s), 8.38-8.42(2H, m), 8.51(1H, m) | 529 | 11 |
| 155 | 1.54(3H, d), 5.31(2H, s), 570-5.81(1H, m), 7.61(1H, bs), 7.78 (1H, dd), 7.85(1H, d), 8.04(1H, bs), 8.12(1H, d), 8.30(1H, d), 8.53(1H, d), 8.65(1H, dd), 9.58(1H, s) | 522 | 12 |
| 156 | 1.52(3H, d), 5.19(2H, s), 5.65-5.72(1H, m), 6.96(1H, bs), 7.36-7.43(2H, m), 7.70(1H, d), 7.81(1H, d), 7.93(1H, d), 8.30 (1H, s), 8.39(1H, d), 8.50(1H, dd) | 522 | 11 |
| 157 | 4.92(2H, s), 5.21-5.19(2H, m), 7.09(1H, d, J = 3.1 Hz), 7.29 (1H, brs), 7.35(1H, t, J = 7.8 Hz), 7.55(1H, d, J = 3.1 Hz), 7.63-7.70(3H, m), 7.97(1H, d, J = 6.6 Hz), 8.42(1H, d, J = 2.0 Hz), 8.55(1H, dd, J = 2.0, 8.8 Hz) | 507, 485 | 12 |
| 158 | 4.66-4.92(4H, m), 4.32(2H, s), 5.32-5.48(1H, m), 7.09(1H, d, J = 3.1 Hz), 7.29(1H, brs), 7.35(1H, t, J = 7.8 Hz), 7.54-7.56(1H, m), 7.62(1H, brs), 7.64(1H, d, J = 8.4 Hz), 7.74(1H, d, J = 9.1 Hz), 7.97(1H, d, J = 7.4 Hz), 8.39(1H, d, J = 2.1 Hz), 8.48(1H, dd, J = 2.1, 8.8 Hz) | 503, 481 | 12 |
| 159 | 1.26(6H, d, J = 6.3 Hz), 3.87-3.99(1H, m), 4.91(2H, s), 5.56 (1H, d, J = 7.8 Hz), 7.08(1H, d, J = 3.0 Hz), 7.13(1H, d, J = 9.4 Hz), 7.28(1H, brs), 7.33(1H, t, J = 7.8 Hz), 7.53(1H, d, J = 3.0 Hz), 7.59-7.64(2H, m), 7.93(1H, d, J = 7.4 Hz), 8.18-8.21(2H, m) | 466, 444 | 12 |

TABLE 81-continued

| Ex | Data | MS | Ref-Ex |
|---|---|---|---|
| 160 | 4.67(2H, dt, J = 3.3, 14.5 Hz), 4.92(2H, s), 6.47(1H, tt, J = 3.3, 54.0 Hz), 7.09(1H, d, J = 3.0 Hz), 7.29(1H, brs), 7.35(1H, d, J = 7.8 Hz), 7.55(1H, d, J = 3.1 Hz), 7.62-7.66(3H, m), 7.99(1H, d, J = 6.9 Hz), 8.39(1H, d, J = 1.9 Hz), 8.51(1H, dd, J = 1.9, 8.8 Hz) | 489, 467 | 12 |

TABLE 82

| Ex | Data | MS | Ref-Ex |
|---|---|---|---|
| 161 | 1.50(3H, d, J = 6.2 Hz), 2.30(3H, s), 4.91(2H, s), 5.43-5.49(1H, m), 7.09-8.09(10H, m) | 445 | 12 |
| 162 | 1.32-1.96(10H, m), 4.77-4.85(1H, m), 4.91(2H, s), 7.08(1H, d, J = 3.1 Hz), 7.28(1H, brs), 7.34(1H, t, J = 7.8 Hz), 7.55(1H, d, J = 3.0 Hz), 7.58-7.65(3H, m), 7.96(1H, d, J = 6.7 Hz), 8.35(1H, d, J = 2.1 Hz), 8.42(1H, dd, J = 2.2, 8.8 Hz) | 507, 483 | 12 |
| 163 | 1.56(3H, d, J = 6.3 Hz), 4.91(2H, s), 5.69-5.70(1H, m), 7.10-7.11(1H, m), 7.29-7.36(2H, m), 7.55-7.65(3H, m), 7.77-7.79(1H, m), 7.94-7.96(1H, m), 8.51-8.54(1H, m), 8.642-8.647(1H, m) | 456 | 12 |
| 164 | 1.53(3H, d, J = 6.3 Hz), 4.91(2H, s), 5.56-5.62(1H, m), 7.08-7.10(1H, m), 7.29-7.36(2H, m), 7.54-7.69(4H, m), 7.94-7.96(1H, m), 8.19-8.22(1H, m), 8.29-8.30(1H, m) | 465 | 12 |
| 165 | 3.70(3H, s), 4.63-4.95(4H, m), 5.28(2H, s), 5.30-5.49(1H, m), 7.12(1H, d), 7.35(1H, dd), 7.58(1H, d), 7.69-7.78(2H, m), 7.97(1H, d), 8.40(1H, d), 8.48(1H, dd) | 518 | 12 |
| 166 | 1.53(1H, d, J = 6.3 Hz), 4.91(1H, s), 5.55-5.62(1H, m), 7.08-7.10(1H, m), 7.29-7.36(2H, m), 7.54-7.65(4H, m), 7.94-7.96(1H, m), 8.23-8.25(1H, m), 8.42-8.43(1H, m) | 509 | 12 |
| 167 | 1.53(3H, d), 5.67(2H, s), 5.70-5.77(1H, m), 7.20(1H, d), 7.48(1H, dd), 7.69(1H, d), 7.82(1H, d), 7.90(1H, d), 8.05(1H, d), 8.42(1H, d), 8.53(1H, dd) | 479 | 12 |
| 168 | 1.50(3H, d), 2.30(3H, s), 3.69(3H, s), 5.27(2H, s), 5.42-5.53(1H, m), 7.13(1H, d), 7.35(1H, dd), 7.45(1H, d), 7.57(1H, d), 7.70(1H, d), 7.95(1H, d), 8.06-8.11(2H, m) | 482 | 12 |
| 169 | 1.53(3H, d), 2.63(3H, d), 4.93(2H, s), 5.70-5.76(1H, m), 7.10(1H, dd), 7.35(1H, dd), 7.56(1H, d), 7.65(1H, d), 7.81(1H, d), 7.97(1H, dd), 8.09-8.20(1H, m), 8.42(1H, d), 8.53(1H, dd) | 535 | 12 |
| 170 | 1.53(3H, d), 3.70(3H, s), 5.28(2H, s), 5.70-5.76(1H, m), 7.13(1H, dd), 7.36(1H, dd), 7.59(1H, d), 7.72(1H, d), 7.82(1H, d), 7.98(1H, dd), 8.42(1H, d), 8.53(1H, dd) | 536 | 12 |
| 171 | 1.53(3H, d), 5.00(2H, s), 5.67-5.80(1H, m), 7.04(1H, d), 7.24(1H, br), 7.68(1H, br), 7.77(1H, d), 7.83(1H, d), 7.88(1H, d), 8.43(1H, dd), 8.46(1H, d), 8.55(1H, m) | 500 | 12 |
| 172 | 1.53(3H, d), 2.87(3H, s), 3.14(3H, s), 5.27(2H, s), 5.68-5.76(1H, m), 7.09(1H, dd), 7.32(1H, dd), 7.48(1H, d), 7.65(1H, d), 7.81(1H, d), 7.95(1H, dd), 8.42(1H, d), 8.52(1H, dd) | 527 | 12 |

TABLE 83

| Ex | Data | MS | Ref-Ex |
|---|---|---|---|
| 173 | 1.57(3H, d, J = 6.5 Hz), 4.92(2H, s), 6.01-6.12(1H, m), 7.10(1H, d, J = 3.0 Hz), 7.29(1H, brs), 7.35(1H, t, J = 7.8 Hz), 7.55(1H, d, J = 3.1 Hz), 7.63(1H, brs), 7.64(1H, d, J = 8.3 Hz), 7.96(1H, d, J = 6.9 Hz), 8.73(1H, d, J = 2.1 Hz), 9.01(1H, d, J = 2.1 Hz) | 417, 415, 395, 393 | 13 |
| 174 | 1.57(3H, d, J = 6.5 Hz), 4.92(2H, s), 6.01-6.12(1H, m), 7.10(1H, d, J = 3.8 Hz), 7.29(1H, brs), 7.35(1H, t, J = 7.9 Hz), 7.55(1H, d, J = 3.2 Hz), 7.63(1H, brs), 7.64(1H, d, J = 8.2 Hz), 7.96(1H, d, J = 6.6 Hz), 8.73(1H, d, J = 2.0 Hz), 9.01(1H, d, J = 2.0 Hz) | 490, 488 | 12 |
| 175 | 1.18(3H, t), 1.52(3H, d), 2.61(2H, t), 3.30(2H, t), 3.40-3.50(4H, m), 4.08(2H, q), 5.65-5.77(1H, m), 6.72(1H, d), 7.22(1H, dd), 7.34(1H, d), 7.79(1H, d), 8.35(1H, d), 8.47(1H, dd) | Not found | 13 |
| 176 | 1.20(3H, t), 1.52(3H, d), 3.34(2H, t), 3.60(2H, t), 4.08-4.19(4H, m), 5.67-5.80(1H, m), 6.66(1H, d), 7.19(1H, dd), 7.35(1H, d), 7.80(1H, d), 8.36(1H, d), 8.47(1H, dd) | 552 | 13 |
| 177 | 1.52(3H, d), 1.78-1.87(2H, m), 2.42(2H, t), 3.14(2H, t), 3.31(2H, t), 3.45(2H, t), 3.59(3H, s), 5.56-5.75(1H, m), 6.68(1H, d), 7.21(1H, dd), 7.32(1H, d), 7.79(1H, d), 8.35(1H, d), 8.47(1H, dd) | 566 | 13 |
| 178 | 1.52(3H, d), 2.83(3H, s), 3.02(3H, s), 3.34(2H, t), 3.58(2H, t), 4.11(2H, s), 5.65-5.76(1H, m), 6.60(1H, d), 7.15(1H, dd), 7.29(1H, d), 7.79(1H, d), 8.36(1H, d), 8.48(1H, dd) | 551 | 13 |

TABLE 83-continued

| Ex | Data | MS | Ref-Ex |
|---|---|---|---|
| 179 | 1.52(3H, d), 3.32(2H, t), 3.58(2H, t), 3.74(2H, s), 5.69-5.78 (1H, m), 6.62(1H, d), 7.14(1H, bs), 7.20(1H, dd), 7.34(1H, d), 7.48(1H, bs), 7.79(1H, d), 8.36(1H, d), 8.47(1H, dd) | 523 | 13 |
| 180 | 1.53(3H, d), 5.00(2H, s), 5.67-5.80(1H, m), 7.04(1H, d), 7.24 (1H, br), 7.68(1H, br), 7.77(1H, d), 7.83(1H, d), 7.88(1H, d), 8.43(1H, dd), 8.46(1H, d), 8.55(1H, m) | 500 | 15 |
| 181 | 1.53(3H, d), 4.92(2H, s), 5.65-5.80(1H, m), 7.09(1H, d), 7.29 (1H, bs), 7.35(1H, dd), 7.55(1H, d), 7.61(1H, bs), 7.64(1H, d), 7.81(1H, d), 7.97(1H, d), 8.42(1H, s), 8.52(1H, dd) | 497 | 13 |
| 182 | 1.53(3H, d), 3.47(3H, s), 4.83(2H, d), 5.70-5.77(1H, m), 7.38 (1H, d), 7.58(1H, dd), 7.82(1H, d), 8.01(1H, d), 8.13(1H, d), 8.41(1H, dd), 8.52(1H, dd), 8.61(1H, d) | 536 | 15 |

TABLE 84

| Ex | Data | MS | Ref-Ex |
|---|---|---|---|
| 183 | 1.52(3H, d), 3.34(2H, d), 3.60(2H, d), 3.65(3H, s), 4.14(2H, s), 5.69-5.80(1H, m), 6.66(1H, d), 7.19(1H, t), 7.35(1H, d), 7.80 (1H, d), 8.36(1H, d), 8.47(1H, dd) | 516 | 16 |
| 184 | 1.53(3H, d), 2.72(3H, s), 5.70-5.79(1H, m), 7.37(1H, d), 7.55 (1H, t), 7.81(1H, d), 8.10(1H, d), 8.12(1H, dd), 8.41(1H, d), 8.52(1H, dd), 8.61(1H, d) | 442 (M-Ac + 2H)+ | 15 |
| 185 | 1.52(3H, d), 3.06(3H, s), 3.50(2H, t), 4.07(2H, t), 5.67-5.80 (1H, m), 7.42-7.55(2H, m), 7.81(1H, d), 7.83(1H, d), 8.38(1H, d), 8.49(1H, dd) | 544 | 19 |
| 186 | 1.43(9H, s), 1.53(3H, d), 3.29-3.66(8H, m), 5.32(2H, s), 5.66-5.78(1H, m), 7.09(1H, d), 7.32(1H, dd), 7.50(1H, d), 7.66(1H, d), 7.82(1H, d), 7.96(1H, d), 8.42(1H, d), 8.53(1H, dd) | Not found | 19 |
| 187 | 1.39(9H, s), 1.53(3H, d), 2.93-3.18(4H, m), 4.92(2H, s), 5.65-5.78(1H, m), 6.85(1H, t), 7.10(1H, d), 7.34(1H, dd), 7.55(1H, d), 7.66(1H, d), 7.81(1H, d), 7.97(1H, d), 8.25(1H, t), 8.42(1H, d), 8.53(1H, dd) | 664 | 19 |
| 188 | 1.53(3H, d), 3.44-3.48(2H, m), 3.58-3.63(4H, m), 3.68-3.72 (2H, m), 5.31(2H, s), 5.70-5.76(1H, m), 7.09(1H, d), 7.33 (1H, dd), 7.50(1H, d), 7.66(1H, d), 7.81(1H, d), 7.96(1H, dd), 8.42(1H, d), 8.53(1H, dd) | 569 | 19 |
| 189 | 1.53(3H, d), 3.63(3H, s), 3.92(2H, d), 5.03(2H, s), 5.70-5.74 (1H, m), 7.10-7.11(1H, m), 7.36(1H, dd), 7.57(1H, d), 7.65 (1H, d), 7.81(1H, d), 7.98(1H, dd), 8.42(1H, d), 8.53(1H, dd), 8.65(1H, t) | 593 | 19 |
| 190 | 1.53(3H, d), 3.38(2H, t), 3.50(2H, dt), 3.60(2H, t), 3.70(2H, dt), 4.69(1H, t), 5.16(1H, t), 5.35(2H, s), 5.69-5.76(1H, m), 7.08 (1H, d), 7.31(1H, dd), 7.48(1H, d), 7.59(1H, d), 7.82(1H, d), 7.95(1H, d), 8.42(1H, d), 8.53(1H, dd) | 609 | 19 |
| 191 | 1.53(3H, d), 2.98-3.05(1H, m), 3.25-3.38(3H, m), 3.48-3.54 (1H, m), 4.55(1H, t), 4.83(1H, d), 4.97(2H, s), 5.70-5.77(1H, m), 7.09(1H, dd), 7.35(1H, dd), 7.56(1H, d), 7.67(1H, d), 7.82 (1H, d), 7.97(1H, dd), 8.17-8.22(1H, m), 8.42(1H, d), 8.53(1H, dd) | 595 | 30 |
| 192 | 3.13-3.22(2H, m), 3.38-3.43(2H, m), 4.64-4.96(5H, m), 4.94 (2H, s), 5.31-5.50(1H, m), 7.09(1H, d), 7.34(1H, dd), 7.56(1H, d), 7.66(1H, d), 7.74(1H, d), 7.96(1H, d), 8.25(1H, t), 8.38(1H, d), 8.48(1H, dd) | 547 | 30 |

TABLE 85

| Ex | Data | MS | Ref-Ex |
|---|---|---|---|
| 193 | 1.50(3H, d), 2.30(3H, s), 3.19(2H, dt), 3.44(2H, dt), 4.74(1H, t), 4.94(2H, s), 5.38-5.54(1H, m), 7.10(1H, d), 7.34(1H, dd), 7.44(1H, d), 7.55(1H, d), 7.65(1H, d), 7.95(1H, d), 8.05-8.12 (2H, m), 8.25(1H, t) | 511 | 30 |
| 194 | 1.53(3H, d), 3.18(2H, dt), 3.42-3.46(2H, m), 4.72-4.76(1H, m), 4.95(2H, s), 5.70-5.76(1H, m), 7.09(1H, d), 7.35(1H, dd), 7.56(1H, d), 7.66(1H, d), 7.81(1H, d), 7.97(1H, d), 8.26(1H, t), 8.42(1H, d), 8.53(1H, dd) | 541 | 30 |
| 195 | 1.17(3H, t), 1.53(3H, d), 3.64-3.69(1H, m), 3.74-3.79(1H, m), 4.09(2H, q), 4.35-4.39(1H, m), 5.05-5.06(2H, m), 5.17(1H, t), 5.70-5.76(1H, m), 7.09(1H, dd), 7.34(1H, dd), 7.57(1H, d), 7.67(1H, d), 7.81(1H, d), 7.97(1H, dd), 8.42(1H, d), 8.53(1H, dd), 8.69(1H, d) | 637 | 30 |
| 196 | 1.36(6H, d), 3.18(2H, dt), 3.44(2H, dt), 4.72(1H, t), 4.94(2H, s), 4.94-5.01(1H, m), 7.09(1H, d), 7.34(1H, dd), 7.55(1H, d), 7.59(1H, d), 7.65(1H, d), 7.96(1H, d), 8.23(1H, t), 8.35(1H, d), 8.44(1H, dd) | 511 | 30 |

TABLE 85-continued

| Ex | Data | MS | Ref-Ex |
|----|------|----|--------|
| 197 | 3.18(2H, dt), 3.44(2H, dt), 4.68-4.73(2H, m), 4.76-4.85(2H, m), 4.88-4.92(1H, m), 4.94(2H, s), 5.21-5.35(1H, m), 7.09 (1H, dd), 7.34(1H, dd), 7.55(1H, d), 7.61(1H, d), 7.65(1H, d), 7.95(1H, dd), 8.18(1H, dd), 8.23(1H, t), 8.27(1H, d) | 513 | 30 |
| 198 | 1.53(3H, d), 2.82-2.96(2H, m), 3.31-3.40(2H, m), 5.00(2H, s), 5.66-5.80(1H, m), 7.11(1H, d), 7.35(1H, dd), 7.59(1H, d), 7.73(1H, d), 7.82(1H, d), 7.97(1H, d), 8.01(2H, bs), 8.42(1H, d), 8.52(1H, dd), 8.54(1H, t) | 542 | 31 |
| 199 | 1.53(3H, d), 5.55-5.67(1H, m), 7.69(1H, d), 8.01(1H, d), 8.18-8.25(2H, m), 8.29(1H, d), 8.48-8.50(1H, m), 9.42(1H, s) $[\alpha]^{D}_{22} = +10.2(c = 0.1\ CH_3OH)$ | 409 | 4 |
| 200 | 1.53(3H, d), 5.55-5.65(1H, m), 7.69(1H, d), 8.00(1H, d), 8.17-8.24(2H, m), 8.29(1H, d), 8.46-8.49(1H, m), 9.35(1H, s) $[\alpha]^{D}_{22} = -9.70(c = 0.1\ CH_3OH)$ | 409 | 4 |
| 201 | 7.70-7.82(2H, m), 7.95(1H, dd), 8.21-8.28(1H, m), 8.33(1H, s), 8.38-8.43(2H, m), 12.8(1H, s) | 315 | 2 |

INDUSTRIAL APPLICABILITY

The compound of the present invention is useful as a medicament, and in particular, for prevention and/or treatment of rejection in the transplantation of an organ, bone marrow, or tissue, an autoimmune disease, or the like, since it has $S1P_1$ agonist activity.

The patents, patent applications and publications cited herein are incorporated by reference.

The invention claimed is:

1. A compound selected from the following, or a pharmaceutically acceptable salt thereof:
   4-{5-[3-(trifluoromethyl)-4-(2,2,2-trifluoro-1-methylethoxy]phenyl)-1,2,4-oxadiazol-3-yl)-1H-pyrrolo[2,3-b]pyridine hydrochloride;
   2-[4-(5-{5-chloro-6-[(1S)-2,2,2-trifluoro-1-methylethoxy]pyridine-3-yl]-1,2,4-oxadiazol-3-yl)-1H-indol-1-yl]acetamide; or
   2-[4-(5-{5-chloro-6-[2-fluoro-1-(fluoromethyl)ethoxy]pyridin-3-yl]-1,2,4-oxadiazol-3-yl)-1H-indol-1-yl)acetamide.

2. A method for treating rejection in transplantation of organ, bone marrow or tissue in human or animal, graft-versus-host disease, rheumatoid arthritis, multiple sclerosis, systemic lupus erythematosus, nephrotic syndrome, encephalomeningitis, myasthenia gravis, pancreatitis, hepatitis, nephritis, diabetes, asthma, atopic dermatitis, inflammatory bowel disease, atherosclerosis, ischemia-reperfusion injury, comprising steps of administering to a patient in need thereof a compound represented by formula (I):

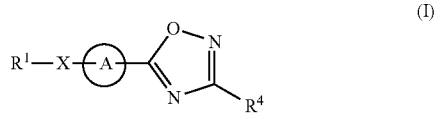
(I)

wherein ring A is

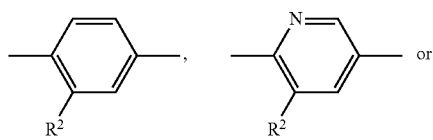 or 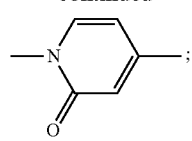

X is a single bond, —$CH_2$—, —$NR^3$—, —O—, —S—, —S(=O)— or —S(=O)$_2$—, $R^1$ is halogen, aryl, heteroaryl, ($C_3$-$C_8$)cycloalkyl, ($C_3$-$C_8$) cycloalkenyl, ($C_3$-$C_8$)heterocycloalkyl, or optionally substituted ($C_1$-$C_6$)alkyl or optionally substituted ($C_2$-$C_8$)alkenyl, wherein the optional substituents are halogen, —$CONH_2$, aryl or ($C_3$-$C_8$)cycloalkyl;

$R^2$ is —CN, —O—($C_1$-$C_6$)alkyl, —C(=O)H, halogen or optionally substituted ($C_1$-$C_6$)alkyl, wherein the optional substituents are halogen or —OH, and when —X— is a single bond, $R^1$ and $R^2$ may in combination form a 5-membered ring optionally substituted with ($C_1$-$C_6$)alkyl groups;

$R^3$ is —H, wherein $R^3$ may form morpholino, 1-pyrrolidinyl or 3,4-dehydropiperidin-1-yl, together with $R^1$ and nitrogen;

$R^4$ is

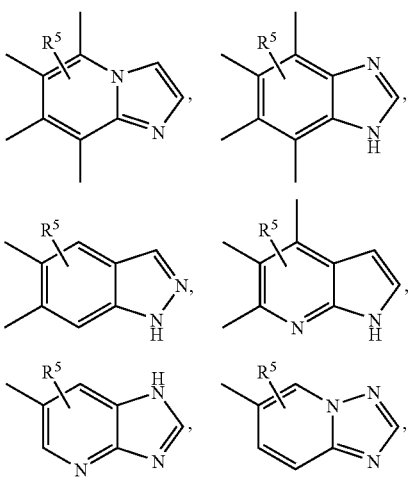

-continued

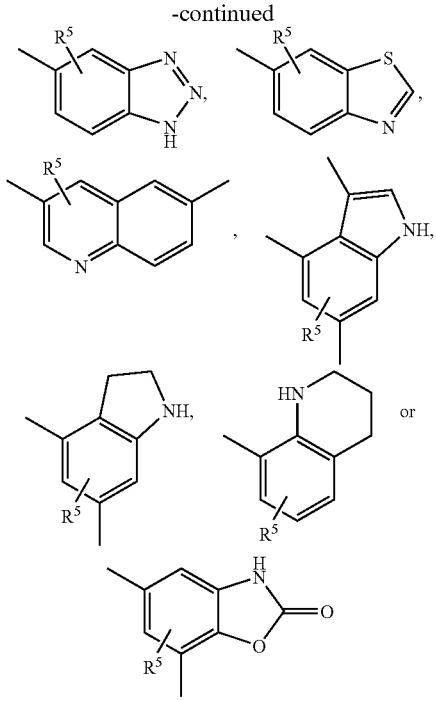

wherein any one of bonds from an $R^4$ ring is bound to the oxadiazole ring;

$R^5$ is —H, $R^O$—$(C_1$-$C_6)$alkyl, $R^O$—$(C_1$-$C_6)$alkyl-O—, $R^O$—$(C_1$-$C_6)$alkyl-C(=O)—, $R^O$—$(C_1$-$C_6)$alkyl-S$(=O)_2$—, $R^O$—O—$(C_1$-$C_6)$alkyl-, $R^O$—C(=O)—$(C_1$-$C_6)$alkyl-, $R^O$—S$(=O)_2$—$(C_1$-$C_6)$alkyl-, $(C_2$-$C_6)$alkenyl-, —C(=O)H, —$OR^X$, —S$(=O)_2R^X$, halogen, =O, —$NR^XR^Y$, or —C(=O)$NR^XR^Y$, wherein $(C_1$-$C_6)$alkyl means $(C_1$-$C_6)$alkyl which may be substituted with at least one group selected from $R^O$;

$R^O$ is —CN, —C(=O)$NR^XR^Y$, —$NHR^x$, —$SR^x$, —S(=O)$_2R^x$ or —$OR^x$; and $R^X$ and $R^Y$ are independently —H, or $(C_1$-$C_6)$alkyl which may be optionally substituted with —OH, —$NH_2$, —NHC(=O)OC(CH$_3$)$_3$ or heteroaryl, wherein —$NR^XR^Y$, —C(=O)$NR^XR^Y$, or —C(=O)$NR^XR^Y$ in $R^5$, $R^X$ and $R^Y$ may form morpholino or piperadino, together with nitrogen, or a pharmaceutically acceptable salt thereof.

3. A method for treating multiple sclerosis, comprising the steps of administering to a patient in need thereof a compound represented by formula (I):

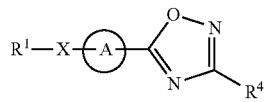

(I)

wherein ring A is

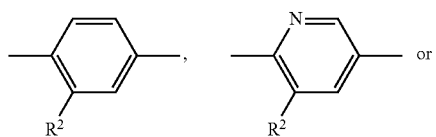

-continued

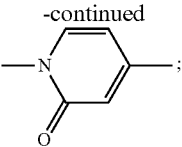

X is a single bond, —$CH_2$—, —$NR^3$—, —O—, —S—, —S(=O)— or —S(=O)$_2$—;

$R^1$ is halogen, aryl, heteroaryl, $(C_3$-$C_8)$cycloalkyl, $(C_3$-$C_8)$cycloalkenyl, $(C_3$-$C_8)$heterocycloalkyl, or optionally substituted $(C_1$-$C_6)$alkyl or optionally substituted $(C_2$-$C_8)$alkenyl, wherein the optional substituents are halogen, —$CONH_2$, aryl or $(C_3$-$C_8)$cycloalkyl;

$R^2$ is —CN, —O—$(C_1$-$C_6)$alkyl, —C(=O)H, halogen or optionally substituted $(C_1$-$C_6)$alkyl, wherein the optional substituents are halogen or —OH, and when —X— is a single bond, $R^1$ and $R^2$ may in combination form a 5-membered ring optionally substituted with $(C_1$-$C_6)$alkyl groups;

$R^3$ is —H, wherein $R^3$ may form morpholino, 1-pyrrolidinyl or 3,4-dehydropiperidin-1-yl, together with $R^1$ and nitrogen;

$R^4$ is

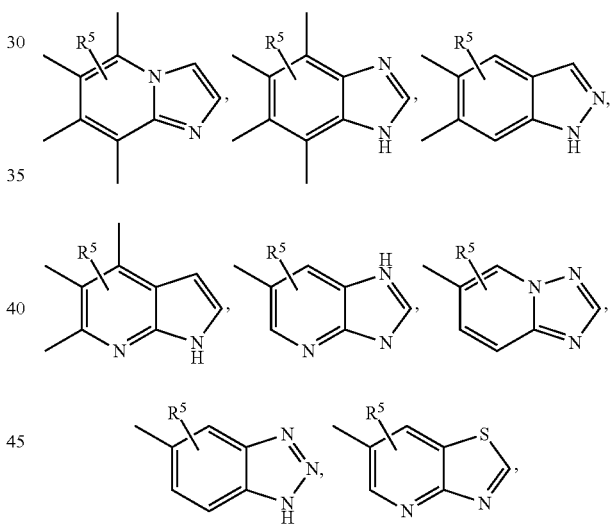

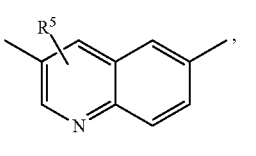

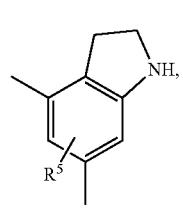

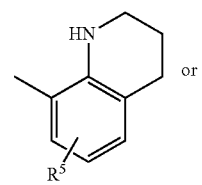

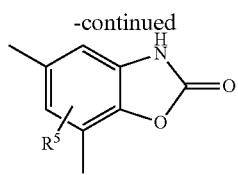

wherein any one of bonds from an R⁴ ring is bound to the oxadiazole ring;

$R^5$ is —H, $R^O$—$(C_1-C_6)$alkyl, $R^O$—$(C_1-C_6)$alkyl-O—, $R^O$—$(C_1-C_6)$alkyl-C(=O)—, $R^O$—$(C_1-C_6)$alkyl-S(=O)_2$—, $R^O$—O—$(C_1-C_6)$alkyl-, $R^O$—C(=O)—$(C_1-C_6)$alkyl-, $R^O$—S(=O)_2$—$(C_1-C_6)$alkyl-, $(C_2-C_6)$alkenyl-, —C(=O)H, —$OR^x$, —$S(=O)_2R^x$, halogen, =O, —$NR^XR^Y$, or —C(=O)$NR^XR^Y$, wherein $(C_1-C_6)$alkyl means $(C_1-C_6)$alkyl which may be substituted with at least one group selected from $R^O$;

$R^O$ is —CN, —C(=O)$NR^XR^Y$, —$NHR^x$, —$SR^x$, —S(=O)_2$R^x$ or —$OR^x$; and $R^X$ and $R^Y$ are independently —H, or $(C_1-C_6)$alkyl which may be optionally substituted with —OH, —NH_2, —NHC(=O)OC(CH_3)_3 or heteroaryl, wherein —$NR^XR^Y$, —C(=O)$NR^XR^Y$, or —C(=O)$NR^XR^Y$ in $R^5$, $R^X$ and $R^Y$ may form morpholino or piperadino, together with nitrogen, or a pharmaceutically acceptable salt thereof.

* * * * *

UNITED STATES PATENT AND TRADEMARK OFFICE
CERTIFICATE OF CORRECTION

PATENT NO. : 7,951,825 B2  
APPLICATION NO. : 12/696327  
DATED : May 31, 2011  
INVENTOR(S) : Hironori Harada et al.

It is certified that error appears in the above-identified patent and that said Letters Patent is hereby corrected as shown below:

ON THE TITLE PAGE [56] REFERENCES CITED :

Foreign Patent Documents,
"WO 01/12627 2/2001       should read  --WO 2001/12627 2/2001
 WO 03/061567 7/2003                    WO 2003/061567 7/2003
 WO 03/105771 12/2003"                  WO 2003/105771 12/2003--.

COLUMN 1:

Line 11, "is" should read --are--;
Line 39, "bind" (first occurrence) should read --binds--; and
Line 55, "transiently-decrease" should read --transient decreases--.

COLUMN 3:

Line 66, "inventors" should read --invention--.

COLUMN 4:

Line 12, "the" (second occurrence) should be deleted;

Lines 40-44, " 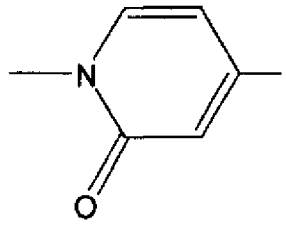 " should read -- 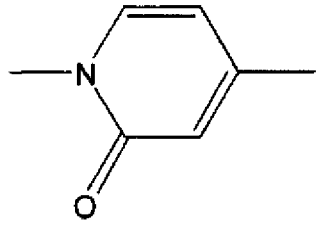 ,--; and

Line 59, "3,4-dehydropipelidin-1-yl," should read --3,4-dihydropiperidin-1-yl,--.

Signed and Sealed this  
Twenty-first Day of February, 2012

David J. Kappos  
*Director of the United States Patent and Trademark Office*

COLUMN 5:

Lines 3-45, "A" (all eleven occurrences) should read --,--.

COLUMN 7:

Line 43, "Further" should read --Further,--; and
Line 63, "one" should read --ones--.

COLUMN 8:

Line 9, "of" should be deleted;
Line 35, "phorphorous" (both occurrences) should read --phosphorus--; and
Line 42, "advantages" should read --advantage--.

COLUMN 9:

Line 33, "mean" should read --means--.

COLUMN 15:

Line 57, "dichloroethane" (first occurrence) should read --dichloromethane,--.

COLUMN 16:

Line 42, "a" should be deleted.

COLUMN 21:

Line 13, "dermiatitis," should read --dermatitis,--;
Line 26, "diseases inendocrine" should read --disease; diseases in endocrine--;
Line 32, "Vascular Injuries," should read --vascular injuries,--;
Line 45, "ophtalmolima," should read --ophthalmolima,--;
Line 46, "Leukopenia," should read --leukopenia,--;
Line 57, "lever" (both occurrences) should read --liver--; and
Line 65, "compound" should read --the compounds--.

COLUMN 22:

Line 2, "but" should read --but are--;
Line 4, "Leflunomide," should read --leflunomide,--;
Line 8, "β-interferone, aspirine," should read --β-interferon, aspirin,--; and
Line 48, "include" should read --includes--.

COLUMN 23:

Line 4, "inhalations" should read --inhalant--.

COLUMN 30:

Line 49, "was" should read --were--.

COLUMN 31:

Line 9, "was" should read --were--.

COLUMN 34:

Line 23, "A" should read --To a--.

COLUMN 35:

Line 7, "MgsO$_4$," should read --MgSO$_4$,--; and
Line 26, "(1:1,20 ml)" should read --(1:1.20 ml)--.

COLUMN 37:

Line 27, "Struture" should read --Structure--.

COLUMN 39:

Line 52, "Pr 21-8" should read --Pr 21-6--.

COLUMN 46:

Line 39, "celite." should read --Celite.--.

COLUMN 47:

Line 23, "celite," should read --Celite,--.

COLUMN 52:

Line 32, "trifluoro-X$^4$" should read --trifluoro-$\lambda^4$--.

COLUMN 64:

Line 1, "as" should be deleted.

COLUMN 65:

Line 13, "(2200," should read --(220 µl),--; and
Line 61, "with" should be deleted.

COLUMN 70:

Line 56, "as it was" should be deleted.

COLUMN 89:

Ex. 122, " 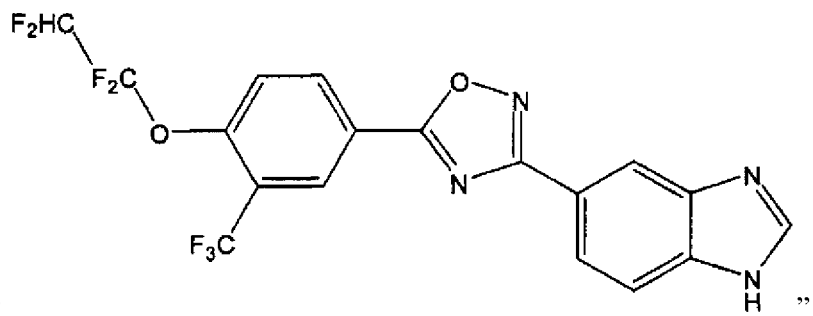 "

should read

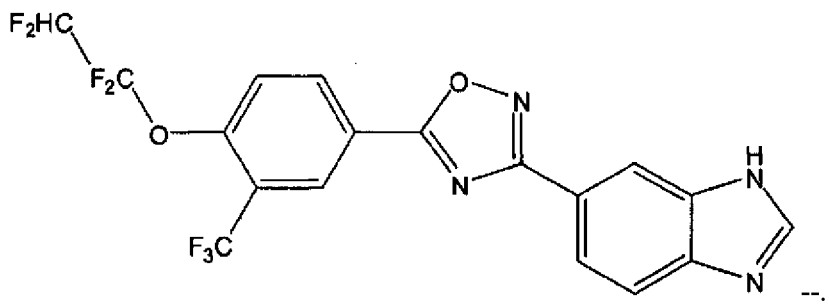

--.

COLUMN 113:

T. 81, Ex. 155, "570-5.81" should read --5.70-5.81--.

COLUMN 119:

Line 34, "ethoxy]phenyl)" should read --ethoxy)phenyl]-- and
   "3-yl) should read --3-yl}--;
Line 37, "3-yl]" should read --3-yl}--;
Line 38, "1-yl)" should read --1-yl]--;
Line 40, "3-yl]" should read --3-yl}-- and "1-yl)" should read --1-yl]--;
Line 44, "multiple sclerosis," should be deleted; and
Line 49, "steps" should read --the steps--.

COLUMN 121:

Line 39, "—S(=O)" should read -- —S(=O)$_2$R$^x$--; and
Line 40, "$_2$R$^x$" should be deleted.

COLUMN 124:

Line 4, "—S(=O)" should read -- —S(=O)$_2$R$^x$--; and
Line 5, "$_2$R$^x$" should be deleted.